United States Patent
Take et al.

(10) Patent No.: US 6,787,543 B2
(45) Date of Patent: Sep. 7, 2004

(54) BENZHYDRYL DERIVATIVES

(75) Inventors: Kazuhiko Take, Osaka (JP); Chiyoshi Kasahara, Osaka (JP); Shinji Shigenaga, Osaka (JP); Hidenori Azami, Osaka (JP); Yoshiteru Eikyu, Osaka (JP); Kazuo Nakai, Osaka (JP); Masataka Morita, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 17 days.

(21) Appl. No.: 10/297,937

(22) PCT Filed: Jun. 25, 2001

(86) PCT No.: PCT/JP01/05424

§ 371 (c)(1),
(2), (4) Date: Dec. 20, 2002

(87) PCT Pub. No.: WO02/00631

PCT Pub. Date: Jan. 3, 2002

(65) Prior Publication Data

US 2003/0176430 A1 Sep. 18, 2003

(51) Int. Cl.$^7$ .................. A61K 31/495; A61K 31/5375; A61P 11/06; C07D 265/30

(52) U.S. Cl. ..................... 514/239.2; 544/105; 544/132; 544/173; 544/350; 544/353; 544/366; 544/374; 544/360; 544/384; 544/389; 544/396

(58) Field of Search ................................ 544/173, 350, 544/396, 366; 514/239.2

(56) References Cited

FOREIGN PATENT DOCUMENTS

| EP | 0 655 442 | 5/1995 |
|---|---|---|
| GB | 2 271 774 | 4/1994 |

*Primary Examiner*—Robert W. Ramsuer
(74) *Attorney, Agent, or Firm*—Oblon, Spivak, McClelland, Maier & Neustadt, P.C.

(57) ABSTRACT

A compound of the formula (I): in which Z, $R^1$, $R^2$, $R^8$, $R^{10}$, $R^{11}$, $R^{12}$, $R^{13}$ and $R^{14}$ are each as defined in the description, or a salt thereof. The object compound of the present invention has pharmacological activities such as Tachykinin antagonism, and is useful for manufacture of a medicament for treating or preventing Tachykinin-mediated diseases.

7 Claims, No Drawings

BENZHYDRYL DERIVATIVES

TECHNICAL FIELD

The present invention relates to new benzhydryl derivatives and a salt thereof.

More particularly, it relates to new benzhydryl derivatives and a salt thereof which have pharmacological activities such as Tachykinin antagonism, especially Substance P antagonism, Neurokinin A antagonism, Neurokinin B antagonism, and the like, to a process for preparation thereof, to a pharmaceutical composition comprising the same, and to a use of the same as a medicament.

Accordingly, one object of the present invention is to provide new and useful benzhydryl derivatives and a salt thereof which have pharmacological activities such as Tachykinin antagonism, especially Substance P antagonism, Neurokinin A antagonism, Neurokinin B antagonism, and the like.

Another object of the present invention is to provide a process for the preparation of said benzhydryl derivatives and a salt thereof.

A further object of the present invention is to provide a pharmaceutical composition comprising, as an active ingredient, said benzhydryl derivatives and a pharmaceutically acceptable salt thereof.

Still further object of the present invention is to provide a use of said benzhydryl derivatives or a pharmaceutically acceptable salt thereof as Tachykinin antagonist, especially Substance P antagonist, Neurokinin A antagonist or Neurokinin B antagonist, useful for treating or preventing Tachykinin-mediated diseases, for example, respiratory diseases such as asthma, bronchitis, rhinitis, couph, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

DISCLOSURE OF INVENTION

The object compound of the present invention can be represented by the following general formula (I):

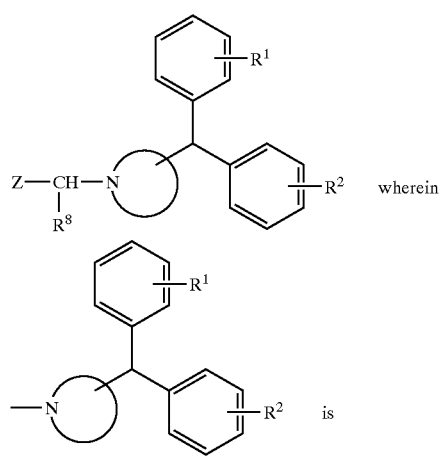

wherein

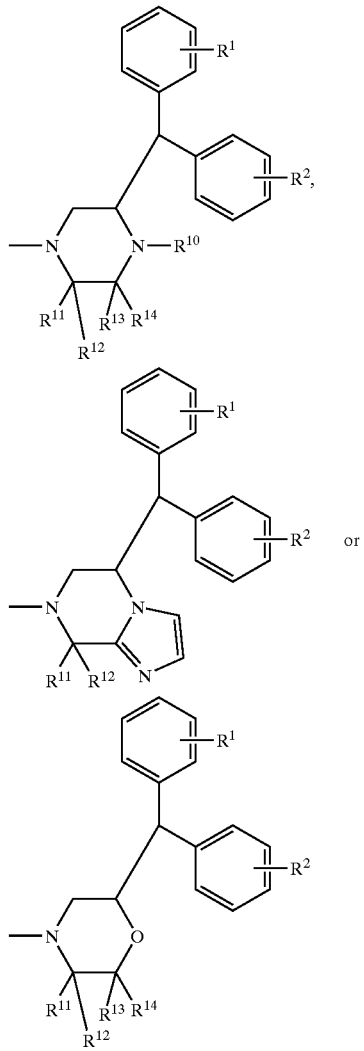

is in which $R^1$ and $R^2$ are independently hydrogen, halogen, lower alkoxy, lower alkyl or mono(or di or tri)halo(lower)alkyl, $R^{10}$ is hydrogen or lower alkyl optionally substituted with lower alkoxy, carbamoyl or phenyl, $R^{11}$, $R^{12}$, $R^{13}$ and $R^{14}$ are independently hydrogen, lower alkoxycarbonyl or lower alkyl optionally substituted with hydroxy or lower alkoxy, and $R^{10}$ and $R^{14}$ optionally forming —$(CH_2)_i$—$CHR^{15}$—$(CH_2)_j$—, —$(CH_2)_i$—$NR^{16}$—$(CH_2)_j$—, —$(CH_2)_i$—O—$CH_2$—CO— or —$(CH_2)_i$—O—$(CH_2)_j$—, wherein i and j are independently 1 or 2, $R^{15}$ is hydrogen, halogen, lower alkyl, hydroxy, lower alkoxy, amino, lower alkylamino or di(lower)alkylamino and $R^{16}$ is hydrogen, lower alkyl, lower alkanoyl, lower alkoxycarbonyl, benzyloxycarbonyl, lower alkylsulfonyl or mono(or di or tri)halo(lower)alkylsulfonyl, or $R^{12}$ and $R^{13}$ optionally forming —$(CH_2)_i$—$CHR^{15}$—$(CH_2)_j$—, wherein i, j and $R^{15}$ are defined as above, or $R^{13}$ and $R^{14}$ optionally forming oxo or two to five methylenes, Z is

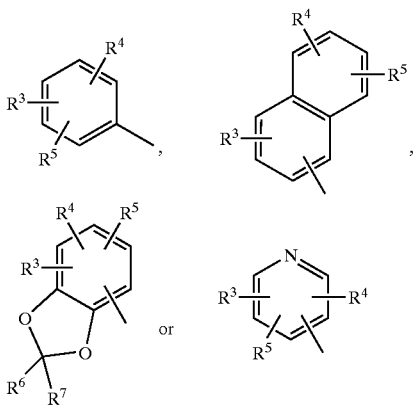

in which $R^3$, $R^4$ and $R^5$ are independently hydrogen; halogen; lower alkyl; mono(or di or tri)halo(lower)alkyl; cyano; lower alkoxycarbonyl; lower alkylthio; lower alkylsulfonyl; hydroxy; lower alkoxy optionally substituted with lower alkoxy, lower alkoxycarbonyl, carbamoyl, cyano, phenyl or one, two or three halogen(s); lower alkenyloxy; cyclo(lower)alkyloxy; nitro; lower alkylamino; di(lower)alkylamino; or imidazolyl, pyrazolyl, thienyl, thiazolyl, furyl, tetrazolyl, pyridyl or phenyl, each of which may have a substituent selected from a group which consists of lower alkyl, mono(or di or tri)halo(lower)alkyl, lower alkylsulfonyl, lower alkylsulfinyl, lower alkylthio, lower alkylamino and di(lower)alkylamino, and $R^6$ and $R^7$ are independently hydrogen or halogen, and $R^8$ is hydrogen or lower alkyl.

It is to be noted that the object compound (I) may include one or more stereoisomers due to asymmetric carbon atom(s) and double bond, and all of such isomers and a mixture thereof are included within the scope of the present invention It is further to be noted that isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

According to the present invention, the object compound (I) or a salt thereof can be prepared by processes which are illustrated in the following schemes.

Process 1

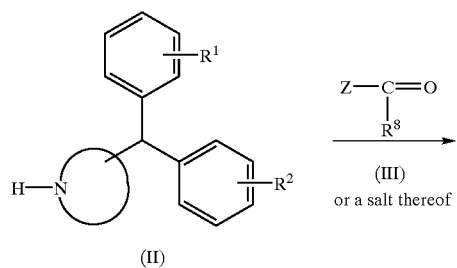

(II)
or its reactive derivative
at the imino group
or a salt thereof

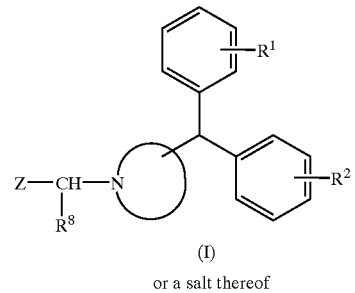

(I)
or a salt thereof

Process 2

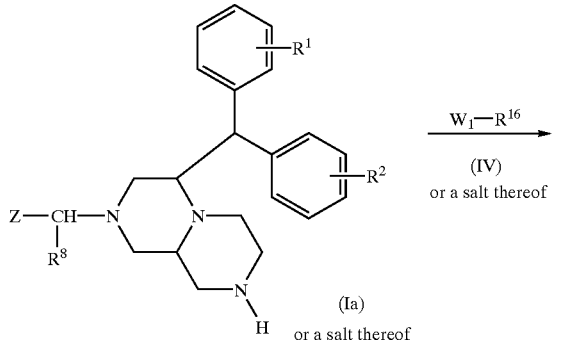

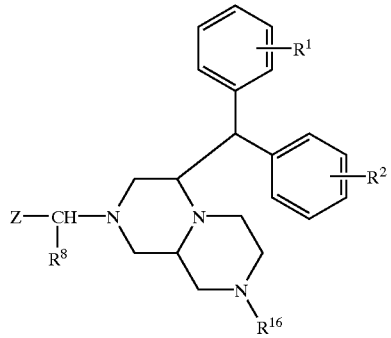

(Ib)
or a salt thereof wherein

Z, $R^1$, $R^2$, $R^8$ and $R^{16}$ are each as defined above, and $W_1$ is a leaving group.

As to the starting compounds (II) and (III), some of them are novel and can be prepared by the procedures described in the Preparations and Examples mentioned later or similar manners thereto.

Suitable salts of the starting and object compounds are conventional non-toxic and pharmaceutically acceptable salt and include an acid addition salt such as an organic acid salt (e.g. acetate, trifluoroacetate, fumarate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention intends to include within the scope thereof are explained in detail as follows.

The term "lower" is intended to mean 1 to 6, preferably 1 to 4, carbon atom(s), unless otherwise indicated.

Suitable "halogen" and "halogen" moiety in the terms "mono(or di or tri)halo(lower)alkyl", "mono(or di or tri)halo($C_1$–$C_4$)alkyl", etc. may include fluorine, chlorine, bromine and iodine.

Suitable "lower alkyl" and "lower alkyl" moiety in the terms "mono(or di or tri)halo(lower)alkyl", "lower alkylamino", etc. may include straight or branched one having 1 to 6 carbon atom(s), such as methyl, ethyl, propyl, isopropyl, butyl, isobutyl, pentyl, hexyl and the like, in which the preferred one is $C_1$–$C_4$ alkyl and the most preferred one is methyl, ethyl or isopropyl.

Suitable "mono(or di or tri)halo(lower)alkyl" and "mono(or di or tri)halo(lower)alkyl" moiety in the term "mono(or di or tri)halo(lower)alkylsulfonyl" may include chloromethyl, dichloromethyl, trichloromethyl, bromomethyl, dibromomethyl, tribromomethyl, fluoromethyl, difluoromethyl, trifluoromethyl, 1 or 2-chloroethyl, 1 or 2-bromoethyl, 1 or 2-fluoroethyl, 1,1-difluoroethyl, 2,2-difluoroethyl and the like.

Suitable "cyclo(lower)alkyl" and "cyclo(lower)alkyl" moiety in the term "cyclo(lower)alkyloxy" may include cyclopropyl, cyclobutyl, cyclopentyl, cyclohexyl and the like.

Suitable "lower alkenyl" moiety in the term "lower alkenyloxy" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)-butenyl, and the like, in which more preferable example may be $C_2$–$C_4$ alkenyl.

Suitable "lower alkoxy" and "lower alkoxy" moiety in the terms "lower alkoxycarbonyl", etc. may include methoxy, ethoxy, propoxy, isopropoxy, butoxy, isobutoxy, t-butoxy, pentyloxy, t-pentyloxy, hexyloxy and the like, in which the preferred one is $C_1$–$C_4$ alkoxy and the most preferred one is methoxy.

Suitable "lower alkanoyl" may include formyl, acetyl, propanoyl, butanoyl, 2-methylpropanoyl, pentanoyl, 2,2-dimethylpropanoyl, hexanoyl and the like.

Suitable "leaving group" may include lower alkoxy (e.g. methoxy, ethoxy, propoxy, isopropoxy, butoxy, isobutoxy, t-butoxy, pentoxy, etc.), aryloxy (e.g., phenoxy, naphthoxy, etc.), an acid residue or the like.

Suitable "acid residue" may be halogen (e.g., chlorine, bromine, iodine, etc.), sulfonyloxy (e.g., methanesulfonyloxy, phenylsulfonyloxy, mesitylenesulfonyloxy, toluenesulfonyloxy, etc.) or the like.

Preferred embodiments of the object compound (I) are as follows:

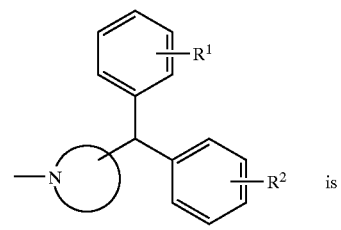

is

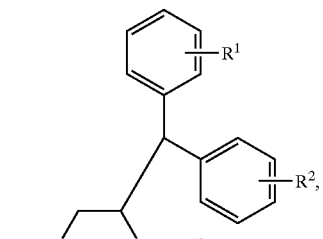

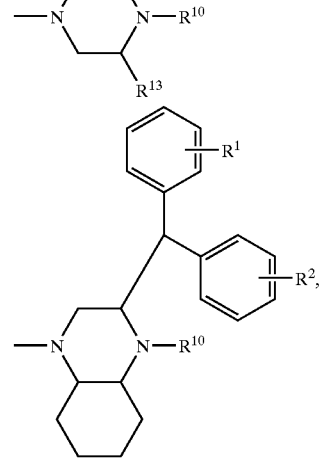

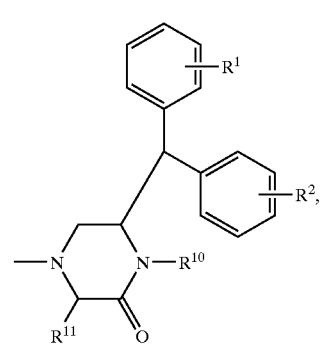

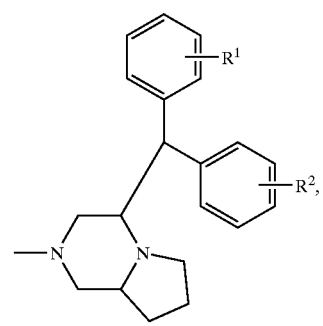

-continued

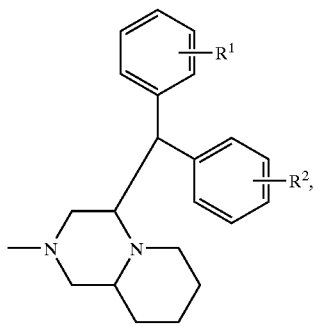

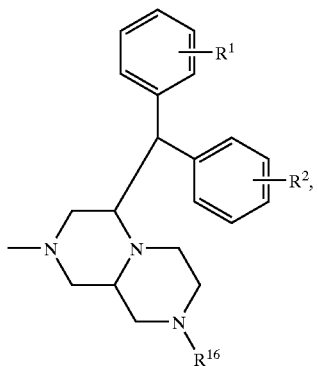

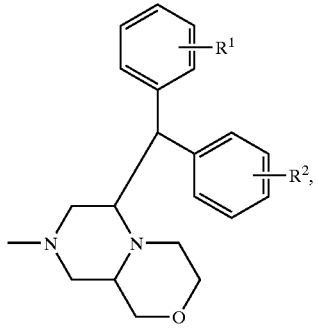

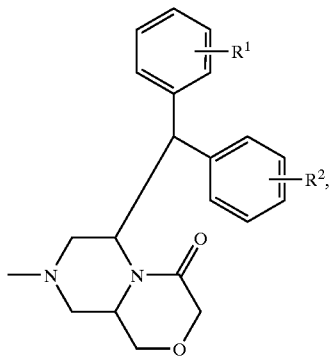

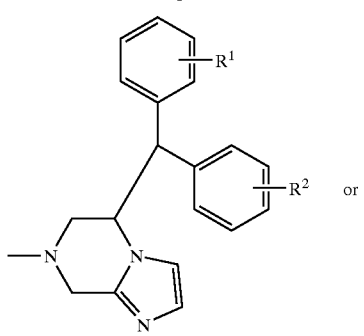

-continued

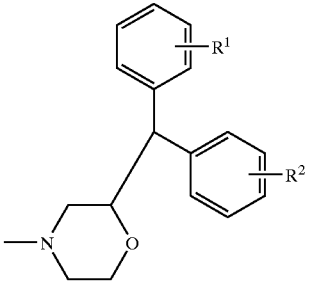

in which $R^1$ and $R^2$ are independently hydrogen, $C_1$–$C_4$ alkoxy, $C_1$–$C_4$ alkyl or mono(or di or tri)halo($C_1$–$C_4$)alkyl, $R^{10}$ is hydrogen or $C_1$–$C_4$ alkyl (more preferably methyl) optionally substituted with $C_1$–$C_4$ alkoxy, carbamoyl or phenyl, $R^{11}$ and $R^{13}$ are independently hydrogen, $C_1$–$C_4$ alkoxycarbonyl (more preferably methylcarbonyl) or $C_1$–$C_4$ alkyl optionally substituted with hydroxy or $C_1$–$C_4$ alkoxy (more preferably hydroxymethyl), $R^{16}$ is hydrogen, $C_1$–$C_4$ alkyl (more preferably methyl), $C_1$–$C_4$ alkanoyl (more preferably acetyl), $C_1$–$C_4$ alkoxycarbonyl (more preferably methoxycarbonyl), benzyloxycarbonyl, $C_1$–$C_4$ alkylsulfonyl or mono(or di or tri)halo($C_1$–$C_4$)alkylsulfonyl, Z is

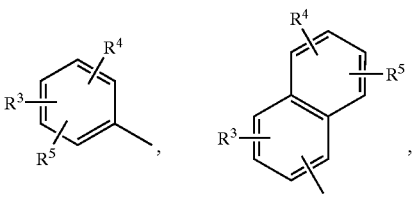

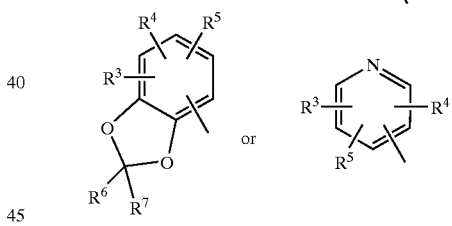

in which $R^3$, $R^4$ and $R^5$ are independently hydrogen; halogen (more preferably fluorine, chlorine or bromine); $C_1$–$C_4$ alkyl (more preferably methyl); mono(or di or tri)halo($C_1$–$C_4$) alkyl (more preferably trifluoromethyl); cyano; $C_1$–$C_4$ alkoxycarbonyl (more preferably methoxycarbonyl); $C_1$–$C_4$ alkylthio (more preferably methylthio); $C_1$–$C_4$ alkylsulfonyl (more preferably mesyl); hydroxy; $C_1$–$C_4$ alkoxy (more preferably methoxy, ethoxy, propoxy or isopropoxy) optionally substituted with $C_1$–$C_4$ alkoxy (more preferably methoxy), $C_1$–$C_4$ alkoxycarbonyl (more preferably methoxycarbonyl), carbamoyl, cyano, phenyl or one, two or three halogen(s) (more preferably fluorine); $C_2$–$C_4$ alkenyloxy (more preferably 2-propenyloxy); cyclo($C_3$–$C_6$) alkyloxy (more preferably cyclopentyloxy); nitro; $C_1$–$C_4$ alkylamino (more preferably methylamino); di($C_1$–$C_4$) alkylamino (more preferably dimethylamino); or imidazolyl, pyrazolyl, thienyl, thiazolyl, furyl, tetrazolyl, pyridyl or phenyl, each of which may have a substituent selected from a group which consists of $C_1$–$C_4$ alkyl (more preferably methyl), mono(or di or tri)halo($C_1$–$C_4$)alkyl (more preferably trifluoromethyl), $C_1$–$C_4$ alkylsulfonyl (more preferably methylsulfonyl), $C_1$–$C_4$ alkylsulfinyl (more preferably methylsulfinyl), $C_1$–$C_4$ alkylthio (more preferably methylthio), $C_1$–$C_4$ alkylamino (more preferably methylamino) and di($C_1$–$C_4$)alkylamino (more preferably dimethylamino), and $R^6$ and $R^7$ are independently hydrogen or halogen, and $R^8$ is hydrogen or $C_1$–$C_4$ alkyl.

More preferred embodiments of the object compound (I) are as follows:

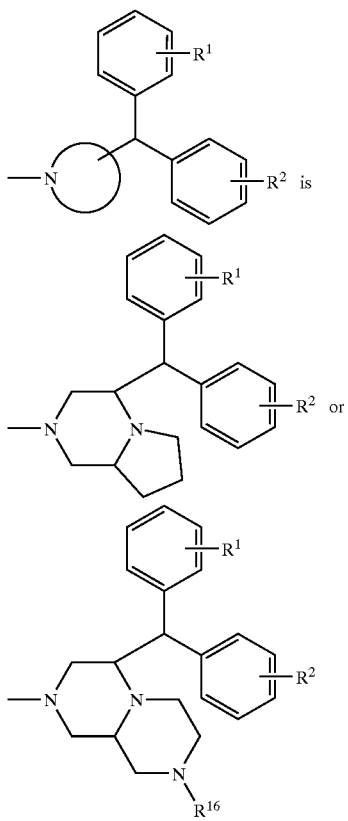

in which $R^1$ and $R^2$ are independently hydrogen, $C_1$–$C_4$ alkoxy, $C_1$–$C_4$ alkyl or mono(or di or tri)halo($C_1$–$C_4$)alkyl, and $R^{16}$ is hydrogen, $C_1$–$C_4$ alkyl (more preferably methyl), $C_1$–$C_4$ alkanoyl (more preferably acetyl), $C_1$–$C_4$ alkoxycarbonyl (more preferably methoxycarbonyl), benzyloxycarbonyl, $C_1$–$C_4$ alkylsulfonyl or mono(or di or tri)halo($C_1$–$C_4$)alkylsulfonyl,

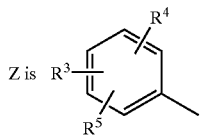

in which $R^3$ is hydrogen, $R^4$ is $C_1$–$C_4$ alkoxy (more preferably methoxy), and $R^5$ is imidazolyl, pyrazolyl, thienyl, thiazolyl, furyl, tetrazolyl, pyridyl or phenyl, each of which may have a substituent selected from a group which consists of $C_1$–$C_4$ alkyl (more preferably methyl), mono(or di or tri)halo($C_1$–$C_4$)alkyl (more preferably trifluoromethyl), $C_1$–$C_4$ alkylsulfonyl (more preferably methylsulfonyl), $C_1$–$C_4$ alkylsulfinyl (more preferably methylsulfinyl), $C_1$–$C_4$ alkylthio (more preferably methylthio), $C_1$–$C_4$ alkylamino (more preferably methylamino) and di($C_1$–$C_4$)alkylamino (more preferably dimethylamino), and $R^8$ is hydrogen or $C_1$–$C_4$ alkyl.

The Processes 1 and 2 for preparing the object compound (I) of the present invention are explained in detail in the following.

Process 1

The object compound (I) or a salt thereof can be prepared by reacting the compound (II) or its reactive derivative at the imino group or a salt thereof with the compound (III) or a salt thereof.

Suitable reactive derivative at the imino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide, bis(trimethylsilyl)urea or the like; a derivative formed by reaction of the compound (II) with phosphorus trichloride or phosgene and the like.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction, or the mixture thereof.

The reaction may also be carried out in the presence of a reductive regent such as hydrides (e.g. hydrogen iodide, hydrogen sulfide, lithium aluminum hydride, sodium borohydride, sodium cyanoborohydride, sodium triacetoxyborohydride, etc.), or the like.

The reaction temperature is not critical, and the reaction is usually carried out under cooling to heating.

Process 2

The object compound (Ib) or a salt thereof can be prepared by reacting the compound (Ia) or a salt thereof with the compound (IV) or a salt thereof.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction may also be carried out in the presence of an inorganic or organic base such as alkali metal carbonate (e.g. potassium carbonate, etc.), alkali metal bicarbonate, tri(lower)alkylamine, pyridine, N-(lower)alkyl-morpholine, N,N-di(lower)alkylethylamine (e.g. N,N-diisopropylethylamine, etc.), N,N-di(lower)alkylbenzylamine, or the like.

The reaction temperature is not critical, and the reaction is usually carried out under cooling to heating.

The object compound (I) and a pharmaceutically acceptable salt thereof have pharmacological activities such as Tachykinin antagonism, especially Substance P antagonism, Neurokinin A antagonism or Neurokinin B antagonism, and therefore are useful for treating or preventing Tachykinin-mediated diseases, particularly Substance P-mediated diseases, for example, respiratory diseases such as asthma, bronchitis (e.g. chronic bronchitis, acute bronchitis and diffuse panbronchiolitis, etc.), rhinitis, couph, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, cluster headache, toothache, cancerous pain, back pain, neuralgia, etc.); and the like.

Further, it is expected that the object compound (I) and a pharmaceutically acceptable salt thereof of the present invention are useful for treating or preventing ophthalmic diseases such as glaucoma, uveitis, and the like;

gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, Raynaud's disease, and the like;

epilepsy; spastic paralysis; pollakiuria; cystitis; bladder detrusor hyperreflexia; urinary incontinence; Parkinson diseases; dimentia; AIDS related dementia; Alzheimer's diseases; Down's syndrome; Huntington's chorea; carcinoid syndrome; disorders related to immune enhancement or suppression; disorders caused by Helicobacter pylori or another spiral urease-positive gram-negative bacterium; sunburn; angiogenesis or diseases caused by angiogenesis; and the like.

It is furthermore expected that the object compound (I) and a pharmaceutically acceptable salt thereof of the present invention are useful for treating or preventing chronic obstructive pulmonary diseases, particularly chronic pulmonary emphysema; iritis; proliferative vitreoretinopathy; psoriasis; inflammatory intestinal diseases, particularly Crohn's diseases; hepatitis; superficial pain on congelation, burn, herpes zoster or diabetic neuropathy; telalgia attended to hyperlipidemia; postoperative neuroma, particularly of mastectomy; vulvar vestibulitis; hemodialysis-associated itching; lichen planus; laryngopharyngitis; bronchiectasis; coniosis; whooping cough; pulmonary tuberculosis; cystic fibrosis; emesis (e.g., nausea, retching, vomiting, acute emesis, delayed emesis, anticipatory emesis, past operative nausea and vomiting (PONV), acute and/or delayed emesis induced by drugs such as cancer chemotherapeutic agents, etc.); mental diseases, particularly anxiety disorders, stress-related disorders, affective disorders, psychological development disorders and schizophrenia; demyelinating diseases such as multiple sclerosis and amyotrophic lateral sclerosis; attenuation of morphine withdrawal; oedema, such as oedema caused by thermal injury; small cell carcinomas, particularly small cell lung cancer (SCLC); hypersensitivity disorders such as poison ivy; fibrosing and collagen diseases such as scleroderma and eosinophilic fascioliasis; reflex sympathetic dystrophy such as shoulder/hand syndrome; addiction disorders such as alcoholism; stress related somatic disorders; rheumatic diseases such as fibrositis; aggressive behaviour, optionally taking an antipsychotic agent together; mania or hypomania, optionally taking an antipsychotic agent together; symptoms associated with Premenstrual Syndrome (PMS) (PMS is also now referred to as Late Luteal Phase Syndrome (LLS); psychosomatic disoredrs; psychoimmunologic disoredrs; attetion deficit disoredrs (ADD) with or without hyperactivity; and the like.

Furthermore, the object compound (I) and a pharmaceutically acceptable salt thereof of the present invention are Central Nervous System (CNS) penetrant.

For therapeutic purpose, the compound (I) and a pharmaceutically acceptable salt thereof of the present invention can be used in a form of pharmaceutical preparation containing one of said compound, as an active ingredient, in admixture with a pharmaceutically acceptable carrier such as an organic or inorganic solid or liquid excipient suitable for oral, parenteral, external including topical, enternal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating Tachykinin-mediated diseases such as asthma and the like. In general, amounts between 0.1 mg/body and about 1,000 mg/body may be administered per day.

In order to show the utility of the object compound (I) and a pharmaceutically acceptable salt thereof, the pharmacological test data of some representative compounds of the present invention is shown in the following.

Emesis in the Dog

[I] Test Method

Individually housed adult female dogs (8 to 15 kg) were given an i.v. injection of a solution containing a test compound. 5 Min later the emetic responses (retching and vomiting) were induced by administration of subcutaneous apomorphine (0.1 mg/0.5 ml/kg) and observed for the next 60 min. The timing and number of retches and vomits observed were recorded for each animal. An individual animal was tested with at least 10 days between experiments.

[II] Test Result

The following Test Compound showed 90% inhibition rate of emesis in the dog at the dose of 1.0 mg/kg.

Test compound: The object compound of the Example 28

The following Preparations and Examples are given for the purpose of illustrating this invention.

Preparation 1

Lithium bis(trimethylsilyl)amide (1.0M in tetrahydrofuran) (77 ml) was added portionwise to a stirred solution of 1,4-dibenzyl-2,5-piperazinedione (20.6 g) in a mixture of tetrahydrofuran (400 ml) and N,N-dimethylformamide (200 ml) at 0° C. The whole was stirred at 5° C. for 1 hour and thereto a solution of bromodiphenylmethane (19 g) in tetrahydrofuran (100 ml) was added at −78° C. and the mixture was stirred for 2 hours at the same temperature. After being stirred at 5° C. for 2 hours, the mixture was poured into ice-water and extracted with ethyl acetate. The extract was washed with 1N hydrochloric acid and brine, dried over sodium sulfate and concentrated under reduced pressure. The residue was triturated with a mixed solvent of ethyl acetate and isopropyl alcohol, and the resulting solid was collected by filtration to give 1,4-dibenzyl-3-benzhydryl-2,5-piperazinedione (10.55 g) as a colorless powder.

NMR (DMSO-$d_6$, $\delta$): 3.27 (1H, d, J=13.0 Hz), 3.71 (1H, d, J=17.4 Hz), 3.84 (1H, d, J=17.4 Hz), 4.23 (1H, d, J=14.6 Hz), 4.49–4.81 (4H, m), 7.03–7.54 (20H, m)

MASS (APCI): 461 (M+H)$^+$

Preparation 2

The following compound was obtained according to a similar manner to that of Example 4.

4-tert-Butoxycarbonyl-2-benzhydryl-1-methylpiperazine

NMR (DMSO-$d_6$, δ): 1.10–1.45 (9H, m), 1.21 (3H, s), 2.40–3.50 (6H, m), 4.05–4.25 (1H, m), 7.10–7.43 (10H, m)

MASS (APCI): 367 (M+H)$^+$

Preparation 3

4N Hydrogen chloride in 1,4-dioxane (44 ml) was added to a solution of 4-tert-butoxycarbonyl-2-benzhydryl-1-methylpiperazine (6.5 g) in ethanol (33 ml) under ice-cooling over 30 minutes. The mixture was stirred at room temperature for 4 hours and evaporated under reduced pressure. The residue was triturated with diisopropyl ether and the resulting solid was collected by filtration to give 2-benzhydrylpiperazine dihydrochloride (6.02 g) as a powder.

NMR (DMSO-$d_6$, δ): 2.50–3.95 (6H, m), 3.56 (3H, s), 4.30–5.50 (2H, m), 7.21–7.57 (11H, m)

MASS (APCI): 267 (M+H)$^+$ (free)

Preparation 4

A solution of 1,4-dibenzyl-3-benzhydryl-2,5-piperazinedione dihydrochloride (840 mg) in methanol (10 ml) was hydrogenated over 10% palladium-carbon (50% wet, 84 mg) at room temperature under atmospheric pressure for 5 hours. After removal of the catalyst by filtration, the filtrate was evaporated under reduced pressure to give an oil, which was treated with 4N hydrogen chloride in ethyl acetate solution to give 2-benzhydrylpiperazine dihydrochloride (525 mg) as a colorless powder.

NMR (DMSO-$d_6$, δ): 3.12–3.89 (8H, m), 4.39 (1H, d, J=11.1 Hz), 4.59 (1H, m), 7.26–7.49 (10H, m)

MASS (APCI): 253 (M+H)$^+$ (free)

Preparation 5

The following compounds were obtained according to a similar manner to that of Preparation 4.

(1) 6-Benzhydrylpiperazine-2-one

NMR (DMSO-$d_6$, δ): 2.43–2.75 (3H, m), 3.19 (2H, s), 4.14 (2H, m), 6.43 (1H, br s), 7.14–7.45 (10H, m)

MASS (APCI): 267 (M+H)$^+$ (2) 5-Benzhydryl-5,6,7,8-tetrahydroimidazo[1,2-a]pyrazine dihydrochloride MASS (APCT): 290 (M+H)$^+$ (free)

(3) (2S)-2-Benzhydrylpiperazine dihydrochloride

NMR (DMSO-$d_6$, δ): 3.12–3.89 (8H, m), 4.39 (1H, d, J=11.1 Hz), 4.59 (1H, m), 7.26–7.49 (10H, m)

MASS (APCI): 253 (M+H)$^+$ (free)

(4) (2S)-2-Benzhydryl-1-methylpiperazine dihydrochloride

NMR (DMSO-$d_6$, δ): 2.66–4.89 (12H, m), 7.21–7.56 (10H, m)

MASS (APCI): 267 (M+H)$^+$ (free)

(5) (2R)-2-Benzhydryl-1-methylpiperazine dihydrochloride

NMR (DMSO-$d_6$, δ): 2.66–4.89 (12H, m), 7.21–7.56 (10H, m)

MASS (APCI): 267 (M+H)$^+$ (free)

(6) (2R)-2-Benzhydrylpiperazine dihydrochloride

NMR (DMSO-$d_6$, δ): 3.12–3.89 (8H, m), 4.39 (1H, d, J=11.1 Hz), 4.59 (1H, m), 7.26–7.49 (10H, m)

MASS (APCI): 253 (M+H)$^+$ (free)

Preparation 6

Di-tert-butyl carbonate (996 mg) was added to a mixture of 2-benzhydrylpiperazine dihydrochloride (1.65 g) and N,N-diisopropylethylamine (3.5 ml) in N,N-dimethylformamide (17 ml) under ice-cooling. After being stirred at same temperature for 2 hours, the mixture was poured into ice-water and extracted with ethyl acetate. The extract was washed with brine, dried over sodium sulfate and evaporated under reduced pressure to give a crude oil. The oil was purified by column chromatography on silica gel using a mixed solvent of dichloromethane and methanol (50:1) to give 1-tert-butoxycarbonyl-3-benzhydrylpiperazine (1.26 g) as a colorless powder.

NMR (CDCl$_3$, δ): 1.39 (9H, s), 2.63–2.95 (4H, m), 3.34 (1H, m), 3.74–3.95 (3H, m), 7.17–7.39 (10H, m)

MASS (APCI): 353 (M+H)$^+$

Preparation 7

A solution of 2-benzhydryloxirane (631 mg) in isopropyl alcohol (4 ml) was added portionwise to a stirred solution of 2-aminoethyl hydrogensulfate (2.12 g) in a mixture of 20% sodium hydroxide solution (3 ml) at 50° C. The whole was stirred at 100° C. for 6 hours and thereto 40% sodium hydroxide solution (6 ml) was added at 100° C. After being stirred for 18 hours at the same temperature, the mixture was partitioned between ethyl acetate and 2N sodium hydroxide. The organic layer was separated, washed with brine, dried over sodium sulfate and evaporated under reduced pressure. The resulting residue was purified by column chromatography on silica gel using a mixed solvent of dichloromethane and methanol (20:1) to give 2-benzhydrylmorpholine (102 mg) as a colorless powder.

NMR (CDCl$_3$, δ): 2.50–2.92 (4H, m), 3.63 (1H, m), 3.84 (1H, m), 3.92 (1H, d, J=9.6 Hz), 4.20 (1H, ddd, J=9.6, 9.6, 2.5 Hz), 7.14–7.37 (10H, m)

MASS (APCI): 254 (M+H)$^+$

Preparation 8

Lithium aluminum hydride (114 mg) was added by small portions to an ice-cooled solution of 1-benzhydryl-2-(N-methoxymethylamino)-2-oxoethylcarbamic acid tert-butyl ester (1.15 g) in tetrahydrofuran (10 ml) below 5° C. under nitrogen atmosphere. After the mixture was stirred at the same temperature for 1 hour, 2N sodium hydroxide (0.5 ml) was added to the mixture. After the mixture was stirred for 30 minutes, the insoluble materials were removed by filtration and washed with tetrahydrofuran. The filtrate and the washing were combined, and evaporated under reduced pressure. The residue was dissolved into dichloromethane (15 ml), and N-benzylglycine ethyl ester (609 mg) was added to the solution. To the resulting solution sodium triacetoxyborohydride (1.27 g) was added portionwise under stirring and the whole was stirred at 5° C.~room temperature overnight. The mixture was partitioned between ethyl acetate and 2N sodium hydroxide. The organic layer was separated, washed with brine, dried over sodium sulfate and evaporated under reduced pressure to give N-benzyl-N-[2-(tert-butoxycarbonylamino)-3,3-diphenylpropyl]glycine ethyl ester (1.51 g) as a colorless oil.

MASS (APCI): 503 (M+H)$^+$

Preparation 9

The following compound was obtained according to a similar manner to that of Preparation 8.

N-(2-tert-Butoxycarbonylamino-3,3-diphenylpropyl)-N-[2-methoxy-5-(trifluoromethoxy)benzyl]glycine methyl ester NMR (CDCl$_3$, δ): 1.32 (9H, s), 2.66 (1H, dd, J=14.5, 6.4 Hz), 2.87 (1H, dd, J=13.7, 4.2 Hz), 3.30 (1H, d, J=4.9 Hz), 3.61 (3H, s), 3.77 (3H, s), 3.82 (2H, m), 4.16 (1H, d, J=8.3 Hz), 4.61 (1H, m), 4.86 (1H, m), 6.81 (1H, d, J=8.9 Hz), 7.08–7.31 (13H, m)

MASS (APCI): 603 (M+H)$^+$

Preparation 10

The following compounds were obtained according to a similar manner to that of Preparation 8 followed by a similar manner to that of Preparation 13.

(1) 6-Benzhydryl-3-methylpiperazin-2-one hydrochloride

NMR (DMSO-d$_6$, δ): 1.39 (3H, m), 2.91 (1H, m), 3.14 (1H, m), 3.52–4.46 (3H, m), 4.70 (1H, m), 7.14–7.53 (10H, m)

MASS (APCI): 281 (M+H)$^+$ (free)

(2) 6-Benzhydryl-3,3-dimethylpiperazin-2-one

NMR (CDCl$_3$, δ): 1.35 (3H, s), 1.37 (3H, s), 2.74–2.95 (2H, m), 3.83 (1H, d, J=10.7 Hz), 4.24 (1H, m), 5.57 (1H, s), 7.17–7.35 (10H, m)

MASS (APCI): 295 (M+H)$^+$

Preparation 1

1-[3-(Dimethylamino)propyl]-3-ethylcarbodiimide hydrochloride (1.15 g) was added over 5 minutes to a mixture of N-(2-methoxybenzyl)glycine methyl ester hydrochloride (1.72 g), N-(tert-butoxycarbonyl)-3,3-diphenyl-L-alanine (1.71 g), 1-hydroxybenzotriazole (0.81 g) and N,N-diisopropylethylamine (1.22 ml) in dichloromethane (40 ml). After being stirred for 3 hours at room temperature, the resulting mixture was extracted with ethyl acetate. The extract was washed with brine, dried over sodium sulfate and evaporated under reduced pressure. The residue was purified by column chromatography on silica gel using a mixed solvent of hexane and ethyl acetate (4:1) to give N-[(2S)-2-(tert-butoxycarbonylamino)-3,3-diphenylpropionyl]-N-(2-methoxybenzyl)glycine methyl ester (2.34 g) as a colorless powder.

NMR (CDCl$_3$, δ): 1.29 (9H, s), 3.62–3.77 (6H, m), 3.89 (1H, m), 4.13 (1H, m), 4.51 (2H, m), 4.86–5.07 (1H, m), 5.30–5.68 (1H, m), 6.44–7.38 (15H, m)

MASS (APCI): 555 (M+Na)$^+$

Preparation 12

The following compound was obtained according to a similar manner to that of Preparation 11.

N-Benzyl-N-[(2R)-2-tert-butoxycarbonylamino-3,3-diphenylpropionyl]glycine ethyl ester NMR (CDCl$_3$, δ): 1.15–1.47 (12H, m), 3.61–4.25 (4H, m), 4.48–4.76 (2H, m), 4.99–5.17 (1H, m), 5.36–5.61 (1H, m), 6.61–7.43 (15H, m)

MASS (APCI): 417 (M+H)$^+$

Preparation 13

4N Hydrogen chloride in ethyl acetate solution (10 ml) was added to a solution of N-[(2S)-2-(tert-butoxycarbonylamino)-3,3-diphenylpropionyl]-N-(2-methoxybenzyl)glycine methyl ester (1.34 g) in ethyl acetate (5 ml) at room temperature. After being stirred for 2 hours, the reaction mixture was concentrated under reduced pressure. The resulting residue was dissolved into isopropyl alcohol (8 ml) and the solution was stirred for 3 hours under reflux. After being cooled with ice, the residue was triturated with diisopropyl ether (50 ml) and the resulting solid was collected by filtration to give (3S)-3-benzhydryl-1-(2-methoxybenzyl)piperazine-2,5-dione (785 mg) as a colorless powder.

NMR (DMSO-d$_6$, δ): 3.01 (1H, d, J=17.4 Hz), 3.50 (1H, d, J=17.4 Hz), 3.75 (3H, s), 4.24 (1H, d, J=15.0 Hz), 4.38 (1H, d, J=15.0 Hz), 4.53 (1H, d, J=5.4 Hz), 4.73 (1H, d, J=5.4 Hz), 6.85–7.33 (14H, m), 8.39 (1H, m)

MASS (APCI): 423 (M+Na)$^+$

Preparation 14

The following compound was obtained according to a similar manner to that of Preparation 13.

(3R)-3-Benzhydryl-1-benzylpiperazine-2,5-dione

NMR (DMSO-d$_6$, δ): 2.98 (1H, d, J=17.2 Hz), 3.47 (1H, d, J=17.2 Hz), 4.16 (1H, d, J=14.5 Hz), 4.54 (1H, d, J=5.4 Hz), 4.57 (1H, d, J=14.5 Hz), 4.76 (1H, dd, J=5.4, 5.4 Hz), 7.07–7.41 (15H, m), 8.40 (1H, m)

MASS (APCI): 371 (M+H)$^+$

Preparation 15

Sodium triacetoxyborohydride (5.6 g) was added portionwise to a mixture of glycine methyl ester hydrochloride (1.63 g), N,N-diisopropylethylamine (2.27 ml) and 2-methoxy-5-(trifluoromethoxy)benzaldehyde (3.8 g) in a mixture of dichloromethane (30 ml) and acetic acid (3 drops) at 0° C. and the whole was stirred at 5° C.~room temperature overnight. The mixture was partitioned between ethyl acetate and 2N sodium hydroxide. The organic layer was separated, washed with brine, dried over sodium sulfate and evaporated under reduced pressure. The resulting residue was purified by column chromatography on silica gel using a mixed solvent of hexane and ethyl acetate (2:1). The fractions containing the objective compound were collected and evaporated under reduced pressure and treated with 4N hydrogen chloride in ethyl acetate solution to give N-[2-methoxy-5-(trifluoromethoxy)benzyl]glycine methyl ester hydrochloride (2.76 g) as a colorless powder.

NMR (DMSO-d$_6$, δ): 3.73 (3H, s), 3.86 (3H, s), 3.92 (2H, s), 4.10 (2H, s), 7.17 (1H, d, J=9.1 Hz), 7.42 (1H, dd, J=9.1, 2.6 Hz), 7.56 (1H, d, J=2.6 Hz), 9.68 (2H, br s)

MASS (APCI): 294 (M+H)$^+$ (free)

Preparation 16

A mixture of (2S)-2-(4-methylphenylsulfonyloxymethyl) pyrrolidine-1-carboxylic acid benzyl ester (26.2 g), 2-methoxybenzylamine (44 ml) and N,N-diisopropylethylamine (17.6 ml) in 1,3-dimethyl-2-imidazolidinone (393 ml) was stirred at 93° C. for 7 hours. The mixture was poured into ice-water and extracted with ethyl acetate. The extract was washed with brine, dried over magnesium sulfate and evaporated under reduced pressure. The residue was purified by column chromatography on silica gel using a mixed solvent of dichloromethane and methanol (20:1). The fractions containing the objective compound were collected and evaporated under reduced pressure to give a syrup of (2S)-2-[(2-methoxybenzylamino) methyl]pyrrolidine-1-carboxylic acid benzyl ester (15.7 g).

NMR (CDCl$_3$, δ): 1.83–2.10 (6H, m), 2.57 (1H, m), 2.81 (1H, m), 3.27–3.66 (2H, m), 3.70–4.18 (5H, m), 5.10 (2H, s), 6.82–7.78 (9H, m)

MASS (APCI): 355 (M+H)$^+$

Preparation 17

3-Bromo-1,1-diphenyl-2-propanone (12.7 g) and N,N-diisopropylethylamine (15.7 ml) were added successively to a solution of (2S)-2-[(2-methoxybenzylamino)methyl] pyrrolidine-1-carboxylic acid benzyl ester (15.6 g) in tetrahydrofuran (156 ml) at 0° C. After being stirred at room temperature for 2 hours, the mixture was poured into ice-water (100 ml) and extracted with ethyl acetate (100 ml×2). The extract was washed with brine, dried over magnesium sulfate and evaporated under reduced pressure. The residue was purified by column chromatography on silica gel using a mixed solvent of hexane and ethyl acetate (3:1). The fractions containing the objective compound were collected and evaporated under reduced pressure to give a colorless syrup of (2S)-2-[[N-(2-oxo-3,3-diphenylpropyl)-N-(2-methoxybenzyl)amino]methyl]pyrrolidine-1-carboxylic acid benzyl ester (1.51 g).

NMR (CDCl$_3$, δ): 1.30–2.00 (3H, m), 2.23–2.70 (2H, m), 3.11–3.93 (8H, m), 3.74 (3H, s), 5.06 (2H, m), 5.36 (1H, m), 6.82–7.31 (19H, m)

MASS (APCI): 563 (M+H)$^+$

Preparation 18

(2S)-2-[[N-(2-Oxo-3,3-diphenylpropyl)-(2-methoxybenzyl)amino]methyl]pyrrolidine-1-carboxylic acid benzyl ester (492 mg) was dissolved in a mixture of methanol (7.4 ml) and 1N hydrochloric acid (0.5 ml), and the solution was hydrogenated over 10% palladium—charcoal (50% wet) (0.15 g) at room temperature under atmospheric pressure for 15 hours. After removal of the catalyst by filtration, the filtrate was evaporated under reduced pressure. The residue was partitioned between aqueous saturated sodium hydrogen carbonate and ethyl acetate. The organic layer was washed with brine, dried over magnesium sulfate and evaporated under reduced pressure. The residue was purified by column chromatography on silica gel using a mixed solvent of dichloromethane and methanol (4:1). The fractions containing the objective compound were collected and evaporated under reduced pressure and the resulting residue was treated with 4N hydrogen chloride in ethyl acetate to give (8aS)-4-benzhydryloctahydropyrrolo[1,2-a]pyrazine dihydrochloride (221.2 mg) as a colorless solid.

NMR (CDCl$_3$, δ): 1.29–1.37 (1H, m), 1.50–1.63 (2H, m), 1.74–1.84 (3H, m), 2.38 (1H, ddd, J=2.2, 9.5, 16.7 Hz), 2.43 (1H, dd, J=11.0, 11.0 Hz), 2.50 (1H, dd, J=11.6, 11.0 Hz), 2.66 (1H, dd, J=12.2 Hz), 2.73 (1H, dd, J=8.0, 8.5 Hz), 3.12 (1H, dd, J=11.6, 1.8 Hz), 3.33 (1H, ddd, J=8.7, 2.1, 11.0 Hz), 4.06 (1H, d, J=8.7 Hz), 7.12–7.43 (10H, m)

MASS (APCI): 293 (M+H)$^+$

Preparation 19

Di-tert-butyl carbonate (3.24 g) was added to a mixture of (8aS)-4-benzhydryloctahydropyrrolo[1,2-a]pyridine dihydrochloride (3.62 g) and triethylamine (3.45 ml) in dichloromethane (100 ml) under ice-cooling. After being stirred at the same temperature for 3 hours, the reaction mixture was washed with water and brine successively, dried over magnesium sulfate and evaporated under reduced pressure. The residue was purified by column chromatography on silica gel using a mixed solvent of hexane and ethyl acetate (20:1). The earlier eluting fractions were collected and evaporated under reduced pressure to give brownish oil of (4S,8aS)-2-tert-butoxycarbonyl-4-benzhydryloctahydropyrrolo[1,2-a]pyridine (0.05 g).

NMR (CDCl$_3$, δ): 1.38 (9H, s), 1.00–2.20 (5H, m), 2.80–3.00 (3H, m), 3.87 (1H, d, J=11.0 Hz), 4.15 (1H, dd, J=2.4, 12.8 Hz), 4.75 (1H, d, J=10.4 Hz), 4.70–4.90 (1H, m), 5.09 (1H, dd, J=2.9, 11.2 Hz), 7.05–7.40 (10H, m)

MASS (APCI): 393 (M+H)$^+$, 337

The later eluting fractions were collected and evaporated under reduced pressure to give brownish oil of (4R,8aS)-2-tert-butoxycarbonyl-4-benzhydryloctahydropyrrolo[1,2-a]pyrazine (1.5 g).

NMR (CDCl$_3$, δ): 1.38 (9H, s), 1.00–1.95 (5H, m), 2.15–2.20 (1H, m), 3.37–2.55 (2H,. m), 2.70–2.75 (1H, m), 3.10–3.20 (1H, m), 3.70–3.85 (1H, m), 4.00–4.20 (1H, m), 4.05 (1H, d, J=8.4 Hz), 7.05–7.40 (10H, m)

MASS (APCI): 393 (M+H)$^+$, 337

Preparation 20

The following compound was obtained according to a similar manner to that of Preparation 3.

(4R,8aS)-4-Benzhydryloctahydropyrrolo[1,2-a]pyridine dihydrochloride

NMR (DMSO-d$_6$, δ): 1.50–5.00 (14H, m), 7.21–7.57 (10H, m), 9.50–10.20 (2H, m)

MASS (APCI): 393 (M+H)$^+$ (free)

Preparation 21

The following compound was obtained according to a similar manner to that of Example 16.

Methyl [2-formyl-4-[5-(trifluoromethyl)-1H-tetrazol-1-yl]phenoxy]acetate

NMR (CDCl$_3$, δ): 3.87 (3H, s), 4.91 (2H, s), 7.10 (1H, d, J=9.0 Hz), 7.66 (1H, dd, J=2.8, 9.0 Hz), 8.01 (1H, d, J=2.8 Hz), 10.58 (1H, s)

MASS (APIES negative): 329 (M−H)$^+$

Preparation 22

Propyl bromide (1 ml) was added to a mixture of 2-hydroxy-6-methoxybenzaldehyde (0.45 g), potassium carbonate (0.83 g) and a small amount of potassium iodide in a mixed solvent of N,N-dimethylformamide (10 ml) and acetone (5 ml). After being stirred for 5 hours at 100° C., the mixture was poured into ice-water (20 ml) and extracted with ethyl acetate. The extract was washed with brine (10 ml), dried over magnesium sulfate and evaporated under reduced pressure. The residue was purified by column chromatography on silica gel using a mixed solvent of hexane and ethyl acetate (4:1). The fractions containing the objective compound were collected and evaporated under reduced pressure to give colorless oil of 2-methoxy-6-propoxybenzaldehyde (0.3 g).

NMR (CDCl$_3$, δ): 1.05 (3H, t, J=7.4 Hz), 1.83 (2H, sext, J=7.4 Hz), 3.89 (3H, s), 4.00 (2H, t, J=6.5 Hz), 6.55 (2H, d, J=8.5 Hz), 7.38 (1H, t, J=8.5 Hz), 10.75 (1H, s)

MASS (APCI): 195 (M+H)$^+$

Preparation 23

The following compounds were obtained according to a similar manner to that of Preparation 22.

(1) 2-Methoxy-6-(2,2,2-trifluoroethoxy)benzaldehyde

NMR (CDCl$_3$, δ): 3.91 (3H, s), 4.41 (2H, q, J=8.0 Hz), 6.56 (1H, d, J=8.2 Hz), 6.72 (1H, d, J=8.3 Hz), 7.47 (1H, t, J=8.4 Hz), 10.51 (1H, s)

MASS (APCI): 235(M+H)$^+$ (2) 2-Ethoxy-6-methoxybenzaldehyde

NMR (CDCl$_3$, δ): 1.43 (3H, t, J=7.6 Hz), 4 12 (2H, q, J=7.6 Hz), 3.89 (3H, s), 6.53 (2H, d, J=8.5 Hz), 7.38 (1H, t, J=8.5 Hz), 10.53 (1H, s)

MASS (APCI): 181 (M+H)$^+$

Preparation 24

Thionyl chloride (0.58 ml) was added dropwise to a solution of L-pipecolinic acid (450 mg) in methanol at room temperature. The reaction mixture was stirred at 55° C. for 2 hours. The whole mixture was evaporated under reduced pressure to give (2S)-piperidine-2-carboxylic acid methyl ester hydrochloride as a colorless oil.

NMR (DMSO-d$_6$, δ): 1.55–1.75 (4H, m), 2.04–2.10 (1H, m), 2.49–2.51 (1H, m), 2.91 (1H, m), 3.20–3.27 (1H, m), 3.77 (3H, s), 4.08 (1H, m), 9.20–9.50 (2H, m)

MASS (APCI): 144 (M+H)$^+$ (free)

Preparation 25

(2S)-Piperidine-2-carboxylic acid methyl ester hydrochloride (625 mg) was dissolved in dichloromethane. Then N,N-diisopropylethylamine (0.91 ml) and benzaldehyde (0.53 ml) were added to the solution at 0° C. After the whole was stirred for 30 minutes at the same temperature, sodium triacetoxyborohydride (1.48 g) was added. The reaction mixture was allowed to room temperature and stirred for 3 hours. The mixture was poured into aqueous saturated sodium hydrogen carbonate solution and extracted with ethyl acetate. The extract was dried over magnesium sulfate and evaporated under reduced pressure to give (2S)-1-benzylpiperidine-2-carboxylic acid methyl ester (795 mg).

NMR (DMSO-d$_6$, δ): 1.26–1.86 (6H, m), 2.04–2.20 (1H, m), 2.88–2.99 (1H, m), 3.16 (1H, dd, J=4.9, 7.3 Hz), 3.40 (1H, d, J=13.3 Hz), 3.74 (3H, s), 3.78 (1H, d, J=13.3 Hz), 7.22–7.38 (5H, m)

MASS (APCI): 234 (M+H)$^+$

Preparation 26

Lithium aluminum hydride was added to an ice-cooled solution of (2S)-1-benzylpiperidine-2-carboxylic acid methyl ester (178 mg) in tetrahydrofuran (2.7 ml) under nitrogen atmosphere. The mixture was stirred for 2 hours below 5° C. The reaction was quenched by a sequential addition of water (0.12 ml), 15% aqueous sodium hydroxide (0.12 ml) and water (0.36 ml) successively, and the whole was stirred at room temperature for 1 hour. The insoluble materials were removed by filtration. The filtrate was dried over sodium sulfate and evaporated under reduced pressure to give (2S)-1-benzyl-2-(hydroxymethyl)piperidine as a colorless oil.

NMR (CDCl$_3$, δ): 1.25–1.72 (6H, m), 1.97–2.19 (2H, m), 2.43–2.49 (1H, m), 2.82–2.90 (1H, m), 3.32 (1H, d, J=13.4 Hz), 3.51 (1H, dd, J=3.9, 10.8 Hz), 3.87 (1H, dd, J=4.2, 10.8 Hz), 4.06 (1H, d, J=13.4 Hz), 7.20–7.38 (5H, m)

MASS (APCI): 206 (M+H)$^+$

Preparation 27

A solution of dimethyl sulfoxide (0.219 ml) in dichloromethane (1.1 ml) was added dropwise to a solution of oxalyl chloride (0.133 ml) in dichloromethane (2.7 ml) under cooling below −60° C. with dry ice-acetone. After 5 minutes, the mixture was allowed to −10° C., and a solution of (2S)-1-benzyl-2-(hydroxymethyl)piperidine (156.5 mg) in dichloromethane (1.6 ml) was added to the mixture. The whole mixture was then cooled below −60° C. and was stirred for 20 minutes at the same temperature. After addition of triethylamine (0.64 ml) followed by stirring at room temperature, the reaction mixture was poured into water and extracted with 1,2-dichloroethane. The extract was dried over magnesium sulfate and evaporated under reduced pressure to give a syrup. Benzylamine (0.33 ml) was added to the solution of the syrup obtained above procedure in 1,2-dichloroethane (2.5 ml) with ice-cooling. After the whole was stirred for 30 minutes at the same temperature, sodium triacetoxyborohydride (0.323 g) was added to this mixture. The reaction mixture was allowed to room temperature and was stirred for 3 hours. The mixture was poured into aqueous saturated sodium hydrogen carbonate solution and extracted with dichloromethane. The extract was dried over magnesium sulfate and evaporated under reduced pressure. The resulting residue was purified by silica gel chromatography using a mixture of dichloromethane and methanol (20:1) as an eluent to give N-benzyl-[(2S)-1-benzylpiperidin-2-ylmethyl]amine (168.5 mg).

NMR (CDCl$_3$, δ): 1.26–1.49 (3H, m), 1.56–1.67 (3H, m), 2.03 (1H, s), 2.04–2.14 (1H, m), 2.42–2.50 (1H, m), 2.66–2.86 (3H, m), 3.25 (1H, d, J=13.6 Hz), 3.73 (2H, s), 3.92 (1H, d, J=13.6 Hz), 7.19–7.38 (20H, m)

MASS (APCI): 295 (M+H)$^+$

Preparation 28

The following compound was obtained according to a similar manner to that of Preparation 17.

3-[N-[((2S)-1-Benzylpiperidin-2-yl)methyl]-N-benzylamino]-1,1-diphenylpropan-2-one NMR (CDCl$_3$, δ): 1.22–1.85 (5H, m), 2.34 (1H, m), 2.61 (2H, m), 2.88–2.95 (1H, m), 3.22 (1H, m), 3.41 (2H, s), 3.66 (2H, s), 4.03 (1H, d, J=15.0 Hz), 4.43 (1H, d, J=5.70 Hz), 5.27 (1H, s), 7.16–7.34 (20H, m)

MASS (APCI): 503 (M+H)$^+$

Preparation 29

The following compound was obtained according to a similar manner to that of Preparation 25.

(2R)-2-(Benzyloxycarbonylamino)-3-(2-methoxybenzylamino)propionic acid methyl ester NMR (CDCl$_3$, δ): 2.90 (1H, dd, J=4.7, 12.5 Hz), 3.01 (1H, dd, J=4.8, 12.5 Hz), 3.73–3.89 (9H, m), 4.40 (1H, m), 5.82 (1H, br), 6.83–7.55 (9H, m)

MASS (APCI): 373 (M+H)$^+$

Preparation 30

The following compounds were obtained according to a similar manner to that of Preparation 17.

(1) (2R)-2-(Benzyloxycarbonylamino)-3-[N-(2-methoxybenzyl)-N-(2-oxo-3,3-diphenylpropyl)amino]propionic acid methyl ester NMR (CDCl$_3$, δ): 3.08 (2H, d, J=5.6 Hz), 3.42 (2H, s), 3.60 (2H, s), 3.70 (3H, s), 3.75 (3H, s), 3.77 (1H, m), 4.26 (1H, m), 5.00 (1H, s), 5.12 (1H, s), 6.41 (1H, d, J=7.0 Hz), 6.72–7.34 (19H, m)

MASS (ESI): 581(M+H)$^+$, 603 (M+Na)$^+$ (2) 3-[N-Benzyl-N-[(4-benzylmorpholin-3-yl)methyl]amino]-1,1-diphenylpropan-2-one IR (Neat): 1724 cm$^{-1}$ NMR (CDCl$_3$, δ): 2.05–2.17 (1H, m), 2.40–2.70 (3H, m), 2.98 (1H, dd, J=3.6, 13.2 Hz), 3.13 (1H, d, J=13.4 Hz), 3.51 (2H, s), 3.67 (2H, s), 3.41–3.65 (1H, m), 3.86 (1H, dd, J=3.0, 11.2 Hz), 4.04 (1H, d, J=13.4 Hz), 5.10 (1H, s), 7.14–7.34 (20H, m)

MASS (APCI): 504 (M+H)$^+$

Preparation 31

1-[3-(Dimethylamino)propyl]-3-ethylcarbodiimido hydrochloride (5.74 g) was added to a solution of (3S)-4-benzyl-5-oxomorpholine-3-carboxylic acid (10.0 g), benzylamine (4.65 ml), 1-hydroxybenzotriazole (5.74 g) and triethylamine (8.89 ml) in dichloromethane (100 ml) under ice-cooling. After being stirred for 15 hours at room temperature, the reaction mixture was washed with aqueous sodium carbonate, 1N hydrochloric acid and brine successively, dried over magnesium sulfate, and evaporated under reduced pressure. The residue was purified by column chromatography on silica gel using a mixed solvent of toluene and ethyl acetate (4:1). The fractions containing the objective compound were collected and evaporated under reduced pressure to give colorless oil of N-benzyl((3S)-4-benzyl-5-oxomorpholin-3-yl)amide (11.6 g).

NMR (CDCl$_3$, δ): 3.72 (1H, dd, J=3.9, 12.0 Hz), 3.79 (1H, d, J=14.6 Hz), 3.70–3.85 (1H, m), 4.18 (2H, q, J=17.0 Hz), 4.27–4.35 (1H, m), 4.37 (1H, dd, J=5.6, 14.8 Hz), 4.56 (1H, dd, J=5.6, 14.8 Hz), 5.46 (1H, d, J=14.6 Hz), 6.80–6.90 (1H, m), 7.20–7.50 (10H, m)

MASS (APCI): 325 (M+H)$^+$

Preparation 32

Lithium aluminum hydride (4.7 g) was added by small portions to a solution of N-benzyl((3S)-4-benzyl-5-oxomorpholin-3-yl)amide (8.0 g) in tetrahydrofuran (50 ml) under nitrogen atmosphere, and the whole was stirred at 70° C. for 15 hours. After being cooled with ice, 2N sodium hydroxide (2 ml) was added to the mixture under nitrogen atmosphere. The resulting precipitates were filtered off and washed with tetrahydrofuran, and the filtrate and the washings were combined and evaporated under reduced pressure to give a crude oil. The oil was purified by column chromatography on silica gel using a mixed solvent of dichloromethane and methanol (9:1). The fractions containing the objective compound were collected, evaporated under reduced pressure to give an oil of N-benzyl[(4-benzylmorpholin-3-yl)methyl]amine (2.4 g).

NMR (CDCl$_3$, δ): 2.18–2.29 (1H, m), 2.50–2.92 (4H, m), 3.17 (1H, d, J=13.4 Hz), 3.51–3.86 (7H, m), 3.99 (1H, d, J=13.4 Hz), 7.21–7.31 (10H, m)

MASS (APCI): 297 (M+H)$^+$

Preparation 33

The following compound was obtained according to a similar manner to that of Preparation 18.

(6R,9aR)-6-Benzhydryl-8-tert-butoxycarbonyloctahydropyrazino[2,1-c][1,4]oxazine

IR (Nujol): 3400, 1715, 1605, 1530, 1500, 1450, 1240, 1200, 1120 cm$^{-1}$

NMR (CDCl$_3$, δ): 1.33 (9H, s), 2.00–3.72 (12H, m), 4.18 (1H, d, J=7.4 Hz), 7.16–7.31 (10H, m)

MASS (APCI): 409 (M+H)$^+$

Preparation 34

1-[3-(Dimethylamino)propyl]-3-ethylcarbodiimide hydrochloride (2.11 g) was added over 5 minutes to a mixture of N,O-dimethylhydroxylamine hydrochloride (1.17 g), (2S)-piperazine-1,2,4-tricarboxylic acid 4-benzyl ester 1-tert-butyl ester (3.64 g), 1-hydroxybenzotriazole (1.49 g) and N,N-diisopropylethylamine (2.1 ml) in dichloromethane (40 ml). After being stirred for 18 hours at room temperature, the resulting mixture was extracted with ethyl acetate. The extract was washed with brine, dried over sodium sulfate and evaporated under reduced pressure. The residue was purified by column chromatography on silica gel using a mixed solvent of hexane and ethyl acetate (3:1) to give 2-(N-methoxy-N-methylcarbamoyl)piperazine-1,4-dicarboxylic acid 4-benzyl ester 1-tert-butyl ester (3.61 g) as a colorless powder.

NMR (CDCl$_3$, δ): 1.45 (9H, s), 2.90–3.20 (5H, m), 3.60–4.20 (6H, m), 4.41 (1H, m), 4.90 (1H, m), 5.06 (1H, d, J=12.4 Hz), 5.16 (1H, d, J=12.4 Hz), 7.33 (5H, m)

MASS (APCI): 308 (M−Boc+H)$^+$

Preparation 35

Lithium aluminum hydride (38 mg) was added by small portions to an ice-cooled solution of 2-(N-methoxy-N-methylcarbamoyl)piperazine-1,4-dicarboxylic acid 4-benzyl ester 1-tert-butyl ester (407 mg) in tetrahydrofuran (5 ml) below 5° C. under nitrogen atmosphere. After the mixture was stirred at the same temperature for 2.5 hours, 2N sodium hydroxide (0.2 ml) was added to the mixture. After the mixture was stirred for 30 minutes, the insoluble materials were removed by filtration and washed with tetrahydrofuran. The filtrate and the washing were combined, and evaporated under reduced pressure to give a residue. Sodium triacetoxyborohydride (424 mg) was added portionwise to a stirred mixture of the residue obtained in the above procedure and 2-methoxybenzylamine (151 mg) in dichloromethane (4 ml). After being stirred at room temperature for 4 hours, 3-bromo-1,1-diphenyl-2-propanone (347 mg) in N,N-dimethylformamide (5 ml) and N,N-diisopropylethylamine (0.35 ml) were added successively to the reaction mixture at 5° C. The whole mixture was stirred at room temperature for 36 hours and then poured into ice-water, and extracted with ethyl acetate. The extract was washed with brine, dried over magnesium sulfate and evaporated under reduced pressure. The residue was purified by column chromatography on silica gel using a mixed solvent of hexane and ethyl acetate (4:1) to give (2R)-2-[[N-(2-methoxybenzyl)-N-(2-oxo-3,3-diphenylpropyl)amino]methyl]piperazine-1,4-dicarboxylic acid 4-benzyl ester 1-tert-butyl ester (170 mg) as a colorless powder.

NMR (CDCl$_3$, δ): 1.41–1.57 (9H, m), 2.70–3.00 (5H m), 3.25–4.35 (11H, m), 4.95–5.15 (3H, m), 6.70–7.29 (19H, m)

Preparation 36

To a solution of (1RS,2RS)-1,2-cyclohexanediamine (114 mg) in N,N-dimethylformamide (4 ml) were added 3-bromo-1,1-diphenyl-2-propanone (289 mg) and sodium triacetoxyborohydride (268 mg) successively and the mixture was stirred at ambient temperature for 5 hours. The reaction mixture was diluted with water (20 ml) and extracted with ethyl acetate three times. After the combined extract was washed with water, the organic phase was extracted with 1N hydrochloric acid. The aqueous phase was adjusted to pH 9–10 with sodium hydroxide under ice-cooling and then extracted with ethyl acetate three times. The combined extract was washed with water and brine successively, dried over magnesium sulfate, and concentrated in vacuo. The residue was dissolved in tetrahydrofuran (5 ml) and to the solution were added triethylamine (404 mg) and di-tert-butyl dicarbonate (436 mg) successively. After the mixture was stirred at ambient temperature for 3 hours, the volatile materials were removed under reduced pressure. The residue was purified by silica gel column chromatography eluted with a mixture of ethyl acetate and hexane (1:3) to give 161 mg of tert-butyl (3RS,4aSR,8aSR)-3-benzhydryloctahydroquinoxaline-1-carboxylate as a mixture with some impurities. Purification of this product by preparative thin layer chromatography (40% ethyl acetate in hexane) gave tert-butyl (3RS,4aSR,8aSR)-3-benzhydryloctahydroquinoxaline-1-carboxylate (42.3 mg).

NMR (CDCl$_3$, δ): 1.12–1.90 (8H, m), 1.36 (9H, s), 2.34 (1H, br d, J=12.8 Hz), 2.57–2.67 (1H, m), 2.80–2.95 (2H, m), 3.57–3.83 (3H, m), 7.16–7.38 (10H, m)

MASS (APCI): 407 (M+H)$^+$

Preparation 37

Tert-Butyl (3RS,4aSR,8aSR)-3-benzhydryloctahydroquinoxaline-1-carboxylate (42 mg) was dissolved in 4N ethyl acetate solution of hydrogen chloride (4 ml) and the mixture was stirred at ambient temperature for 3 hours. The volatile materials were removed under reduced pressure to give (2RS,4aSR,8aSR)-2-benzhydryldecahydroquinoxaline dihydrochloride (28 mg).

NMR (CDCl$_3$, δ) 1.20–2.15 (8H, m), 3.39–3.66 (8H, m), 4.88 (1H, d, J=11.2 Hz), 7.26–7.59 (10H, m)

MASS (APCI): 307 (M+H)$^+$ (free)

Preparation 38

The following compound was obtained according to a similar manner to that of Preparation 36.

Tert-Butyl (3RS,4aSR,8aRS)-3-benzhydryloctahydroquinoxaline-1-carboxylate

NMR (CDCl$_3$, δ): 1.11–2.12 (9H, m), 1.34 (9H, s), 3.13–3.28 (2H, m), 3.36–3.81 (2H, m), 4.02–4.14 (1H, m), 4.49 (1H, d, J=11.5 Hz), 7.06–7.40 (10H, m)

MASS (APCI): 407 (M+H)$^+$

Preparation 39

Tert-Butyl (3RS,4aSR,8aRS)-3-benzhydryloctahydroquinoxaline-1-carboxylate (100 mg) was dissolved in hydrogen chloride (5 ml, 4N solution in ethyl acetate) and the mixture was stirred at ambient temperature for 3 hours. The volatile materials were removed under reduced pressure to give (2RS,4aRS,8aSR)-2-benzhydryldecahydroquinoxaline dihydrochloride, which was dissolved in water and washed with ethyl acetate. The aqueous phase was adjusted to pH 9–10 and extracted with ethyl acetate three times. The combined extract was washed with brine, dried over magnesium sulfate, and concentrated in vacuo to give (2RS,4aRS,8aSR)-2-benzhydryldecahydroquinoxaline (88 mg).

NMR (CDCl$_3$, δ): 1.19–1.83 (9H, m), 2.19–2.36 (1H, m), 2.51 (1H, dd, J=11.4 and 9.4 Hz), 2.73–2.87 (2H, m), 3.07 (1H,. d, J=2.9 Hz), 3.63–3.82 (2H, m), 7.10–7.42 (10H, m)

MASS (APCI): 307 (M+H)$^+$

Preparation 40

The following compound was obtained according to a similar manner to that of Example 14 from 3-formyl-4-methoxyphenylboronic acid.

2-Methoxy-5-(4-pyridyl)benzaldehyde

NMR (CDCl$_3$, δ): 4.00 (3H, s), 7.12 (1H, m), 7.45–7.53 (2H, m), 7.85 (1H, dd, J=2.5, 8.7 Hz), 8.14 (1H, m), 8.64–8.97 (2H, m), 10.52 (1H, s)

MASS (APCI): 214 (M+H)$^+$

Preparation 41

The following compounds were obtained according to a similar manner to that of Preparation 22 from each corresponding hydroxybenzaldehyde.

(1) 2-Ethoxy-4,6-dimethoxybenzaldehyde

NMR (CDCl$_3$, δ): 1.46 (3H, t, J=7.0 Hz), 3.86 (3H, s), 3.88 (3H, s), 4.09 (2H, q, J=7.0 Hz), 6.07 (2H, s), 10.38 (1H, s)

MASS (APCI): 211 (M+H)$^+$ (2) 2-Isopropoxy-4,6-dimethoxybenzaldehyde

NMR (CDCl$_3$, δ): 1.38 (6H, d, J=6.1 Hz), 3.86 (3H, s), 3.88 (3H, s), 4.59 (1H, m), 6.06 (1H, d, J=2.1 Hz), 6.08 (1H, d, J=2.1 Hz), 10.36 (1H, s)

MASS (ESI): 247 (M+Na)$^+$ (3) 5-(1H-Imidazol-1-yl)-2-methoxybenzaldehyde

NMR (CDCl$_3$, δ): 4.00 (3H, s), 7.06–7.85 (6H, m), 10.50 (1H, s)

MASS (APCI): 203 (M+H)$^+$

Preparation 42

The following compound was obtained according to a similar manner to that of Preparation 27.

Benzyl (2S)-2-[(benzylamino)methyl]-1-pyrrolidinecarboxylate

IR (neat, FT—IR): 3410, 2765, 1695, 1420, 1355 cm$^{-1}$

NMR (DMSO-d$_6$, δ): 1.69–2.12 (4H, m), 3.20 (2H, br s), 4.04–4.26 (3H, m), 5.01–5.16 (2H, m), 7.26–7.53 (10H, m)

MASS (APCI): 325 (M+H)$^+$

Preparation 43

The following compound was obtained according to a similar manner to that of Preparation 17.

Benzyl (2S)-2-[[benzyl[3,3-bis(4-fluorophenyl)-2-oxopropyl]amino]methyl]-1-pyrrolidinecarboxylate IR (neat, FT-IR): 1700, 1415, 1335 cm$^{-1}$ NMR (CDCl$_3$, δ): 1.48–5.30 (16H, m), 6.91–7.33 (18H, m)

MASS (APCI): 569 (M+H)$^+$

Preparation 44

The following compound was obtained according to a similar manner to that of Preparation 18.

(4R,8aS)-4-[Bis(4-fluorophenyl)methyl]-octahydropyrrolo[1,2-a]pyrazine

Preparation 45

The following compound was obtained according to a similar manner to that of Preparation 34.

Benzyl (2S)-2-(N-methoxy-N-methylcarbamoyl)-1-pyrrolidinecarboxylate

NMR (CDCl$_3$, δ): 1.82–2.26 (4H, m), 3.10–3.22 (3H, m), 3.49–3.72 (2H, m), 3.41–3.80 (3H, m), 4.63–4.81 (1H, m), 5.00–5.23 (2H, m), 7.27–7.38 (5H, m)

MASS (APCI): 293 (M+H)$^+$

Preparation 46

Methyl magnesium bromide in tetrahydrofuran (1M, 36.9 ml) was added into a solution of benzyl (2S)-2-(N-methoxy-N-methylcarbamoyl)-1-pyrrolidinecarboxylate (3.6 g) in tetrahydrofuran (36 ml) under ice-cooling. After being stirred for 2 hours at the same temperature, the reaction mixture was poured into saturated aqueous ammonium chloride, and extracted with ethyl acetate. The extract was washed with brine, dried over magnesium sulfate and evaporated under reduced pressure. The resulting residue was purified by silica gel column chromatography with a mixture of hexane and ethyl acetate (1:1) as an eluent to give benzyl (2S)-2-acetyl-1-pyrrolidinecarboxylate (0.81 g).

NMR (CDCl$_3$, δ): 1.71–2.27 (7H, m), 3.51–3.63 (2H, m), 4.28–4.45 (1H, ddd, J=4.6, 8.4, 13 Hz), 5.02–5.21 (2H, m), 7.26–7.36 (5H, m)

MASS (APCI): 248 (M+H)$^+$

Preparation 47

The following compound was obtained according to a similar manner for Preparation 25 from benzyl (2S)-2-acetyl-1-pyrrolidinecarboxylate.

Benzyl (2S)-2-[1-(benzylamino)ethyl]-1-pyrrolidinecarboxylate

NMR (CDCl$_3$, δ): 1.01–2.04 (8H, m), 2.99–4.45 (6H, m), 5.10 (2H, br), 7.21–7.32 (10H, m)

MASS (APCI): 339 (M+H)$^+$

Preparation 48

The following compound was obtained according to a similar manner to that of Preparation 17 from benzyl (2S)-2-[1-(benzylamino)ethyl]-1-pyrrolidinecarboxylate.

Benzyl (2S)-2-[1-[N-benzyl-N-(2-oxo-3,3-diphenylpropyl)amino]ethyl]-1-pyrrolidinecarboxylate NMR (CDCl$_3$, δ): 0.81–5.24 (23H, m), 7.13–7.79 (15H, m)

MASS (APCI): 547 (M+H)$^+$

Preparation 49

Benzyl (2S)-2-[1-[N-benzyl-N-(2-oxo-3,3-diphenylpropyl)amino]ethyl]-1-pyrrolidinecarboxylate was dissolved in a mixture of methanol (4 ml), tetrahydrofuran (0.5 ml) and 1N-hydrochloric acid (0.41 ml). The solution was hydrogenated over 10% palladium-charcoal (50% wet) at room temperature under 3 atom pressure for 5 hours. After removal of the catalyst by filtration, the filtrate was evaporated under reduced pressure. The residue was partitioned between aqueous saturated sodium hydrogen carbonate and ethyl acetate. The organic layer was washed with brine, dried over magnesium sulfate and evaporated under reduced pressure. The residue was purified by silica gel column chromatography with a mixture of dichloromethane and methanol (6:1) as an eluent. The earlier and later fractions were separately collected and evaporated under reduced pressure separately to give each colorless oil, which were used for next steps separately.

The later eluting fractions of (1R or 1S,4R,8aS)-4-benzhydryl-1-methyloctahydropyrrolo[1,2-a]pyrazine NMR (CDCl$_3$, δ): 1.04–4.10 (16H, m), 6.90–7.42 (10H, m)

MASS (APCI): 307 (M+H)$^+$

The earlier eluting fractions of (1S or 1R,4R,8aS)-4-benzhydryl-1-methyloctahydropyrrolo[1,2-a]pyrazine NMR (CDCl$_3$, δ): 1.04–2.82 (12H, m), 3.44–4.17 (4H, m), 6.90–7.42 (10H, m)

MASS (APCI): 307 (M+H)$^+$

Preparation 50

The following compound was obtained according to a similar manner to that of Preparation 27.

Benzyl (2S,4R)-2-[(benzylamino)methyl]-4-[[tert-butyl(dimethyl)silyl]oxy]-1-pyrrolidinecarboxylate IR (Neat): 1702, 1422, 1504 cm$^{-1}$ NMR (CDCl$_3$, δ): 0.89 (9H, s), 0.13 (6H, s), 1.90–2.00 (2H, m), 2.70–2.85 (2H, m), 3.40–3.50 (2H, m), 3.70–3.85 (2H, m), 4.11 (1H, br s), 4.35–4.45 (1H, m), 5.05–5.20 (2H, m), 7.16–7.35 (10H, m)

MASS (APCI): 455 (M+H)$^+$ (free)

Preparation 51

The following compound was obtained according to a similar manner to that of Preparation 17.

Benzyl (2S,4R)-2-[[N-benzyl-N-(2-oxo-3,3-diphenylpropyl)amino]methyl]-4-[[tert-butyl(dimethyl)silyl]oxy]-1-pyrrolidinecarboxylate NMR (CDCl$_3$, δ) 0.13 (6H, s), 0.82 (9H, s), 1.60–4.20 (12H, m), 5.00–5.20 (3H, m), 7.16–7.35 (20H, m)

MASS (APCI): 685 (M+Na), 663 (M+H)$^+$, 505, 455, 415, 356

Preparation 52

A solution of (2S,4R)-2-[[N-benzyl-N-(2-oxo-3,3-diphenylpropyl)amino]methyl]-4-[(tert-butyldimethylsilyl)oxy]-1-pyrrolidinecarboxylate (4.82 g) and acetic acid (0.87 g) in methanol (100 ml) was hydrogenated over 10% palladium-charcoal (50% wet, 1.0 g) at room temperature under 2–3 atoms for 15 hours. After removal of the catalyst by filtration, the filtrate was evaporated under reduced pressure to give bis(acetic acid) salt of (7R,8aS)-4-benzhydryl-7-[(tert-butyldimethylsilyl)oxy]octahydropyrrolo[1,2-a]pyrazine (4.05 g) as a syrup.

IR (KBr): 3400, 1648, 1504 cm$^{-1}$

NMR (CDCl$_3$, δ): −0.20−−0.11 (6H, m), 0.74–0.81 (9H, m), 2.03 (6H, s), 1.60–1.80 (2H, m), 2.00–4.70 (10H, m), 7.16–7.35 (10H, m)

MASS (APCI): 423 (M+H)$^+$ (free)

Preparation 53

Di-tert-butyl dicarbonate (4.4 g) was added to an ice-cooled mixture of bis(acetic acid) salt of (7R,8aS)-4-benzhydryl-7-[(tert-butyldimethylsilyl)oxy]octahydropyrrolo[1,2-a]pyrazine (7.6 g) and triethylamine (4.9 ml) in dichloromethane (200 ml). After being stirred at the same temperature for 3 hours the reaction mixture was washed with water and brine successively, dried over magnesium sulfate and evaporated under reduced pressure. The residue was purified by column chromatography on silica gel using a mixed solvent of hexane and ethyl acetate (4:1). The eluting fractions were collected and evaporated under reduced pressure to give colorless oil of tert-butyl (7R,8aS)-4-benzhydryl-7-[(tert-butyldimethylsilyl)oxy]hexahydropyrrolo[1,2-a]pyrazine-2(1H)-carboxylate (6.9 g). This compound (6.88 g) was dissolved into 1M tetrabutylammonium floride in tetrahydrofuran (65 ml). After being stirred for 3 hours at room temperature the reaction mixture was poured into water, the whole was extracted with ethyl acetate. The extract was washed with brine, dried over magnesium sulfate and evaporated under reduced pressure. The syrup was purified by column chromatography on silica gel using a mixed solvent of hexane and ethyl acetate (4:1). The later eluting fractions were collected and evaporated under reduced pressure to give colorless oil of tert-butyl (4R,7R,8aS)-4-benzhydryl-7-hydroxyhexahydropyrrolo[1,2-a]pyrazine-2(1H)-carboxylate (1.3 g).

IR (neat): 1695, 1504 cm$^{-1}$

NMR (CDCl$_3$, δ): 1.43 (9H, s), 1.31–1.74 (3H, m), 2.20–2.75 (3H, m), 1.93 (1H, dd, J=4.2 and 9.9 Hz), 3.08 (1H, dd, J=6.1 and 9.9 Hz), 3.30–3.40 (1H, m), 3.60–3.70 (1H, m), 3.78 (1H, br s), 3.94 (1H, d, J=9.0 Hz), 4.15–4.19 (1H, m), 7.13–7.45 (10H, m)

MASS (APCI): 409 (M+H)$^+$ (free)

The earlier eluting fractions were collected and evaporated under reduced pressure to give colorless oil of tert-butyl (4S,7R,8aS)-4-benzhydryl-7-hydroxyhexahydropyrrolo[1,2-a]pyrazine-2(1H)-carboxylate (1.5 g).

NMR (CDCl$_3$, δ) 1.32 (9H, s), 1.50–2.00 (3H, m), 2.40–2.55 (2H, m), 3.00–3.10 (2H, m), 3.40–4.05 (5H, m), 4.30 (1H, d, J=11.2 Hz), 7.15–7.45 (10H, m)

MASS (APCI): 409 (M+H)$^+$ (free)

Preparation 54

Methyl iodide (23 μl) was added to an ice-cooled mixture of tert-butyl (4S,7R,8aS)-4-benzhydryl-7-hydroxyhexahydropyrrolo[1,2-a]pyrazine-2(1H)-carboxylate (155 mg) and cetyltrimethylammonium bromide (15 mg) and finely powdered sodium hydroxide (76 mg) in dichloromethane (2 ml), and the whole was stirred for 5 hours. Additional methyl iodide (23 μl) was added to the mixture and the mixture was further stirred overnight. The resulting mixture was poured into water and extracted with dichloromethane. The organic layer was separated, dried over magnesium sulfate, concentrated under reduced pressure. The syrup was purified by column chromatography on silica gel using a mixed solvent of hexane and ethyl acetate (4:1). The fractions containing the objective compound were collected to give tert-butyl (4S,7R,8aS)-4-benzhydryl-7-methoxyhexahydropyrrolo[1,2-a]pyrazine-2(1H)-carboxylate (56 mg) as a syrup.

IR (neat): 3400, 1691, 1504 cm$^{-1}$

MASS (APCI): 423 (M+H)$^+$

Preparation 55

The following compound was obtained according to a similar manners to that of Preparations 54 and 37.

(4R,7R,8aS)-4-Benzhydryl-7-methoxyoctahydropyrrolo[1,2-a]pyrazine dihydrochloride

MASS (APCI): 323 (M+H)$^+$

Preparation 56

Methanesulfonyl chloride (0.18 ml) was added dropwise to an ice-cooled solution of tert-butyl (4R,7R,8aS)-4-benzhydryl-7-hydroxyhexahydropyrrolo[1,2-a]pyrazine-2(1H)-carboxylate (0.78 g) and triethylamine (0.53 ml) in dichlorometane. After being stirred for 3 hours at the same temperature the mixture was washed with aqueous saturated sodium hydrogen carbonate, dried over magnesium sulfate and concentrated under reduced pressure. The syrup obtained by above procedure and sodium azide (126 mg) was dissolved into dimethylsulfoxide (5 ml). The whole was stirred at 75° C. for 15 hours. The mixture was poured into water and extracted with ethyl acetate. The extract was washed with brine, dried over magnesium sulfate and concentrated under reduced pressure. The syrup was purified by column chromatography on silica gel using a mixed solvent of hexane and ethyl acetate (30:1). The fractions containing the objective compound were collected to give (4R,7S,8aS)-4-benzhydryl-2-(tert-butoxycarbonyl)octahydropyrrolo[1,2-a]pyrazine-7-azide (0.70 mg).

NMR (CDCl$_3$, δ): 1.30–1.40 (2H, m), 1.38 (9H, s), 1.98–2.06 (1H, m), 2.15–2.27 (2H, m), 2.31–2.65 (2H, m), 2.78 (1H, d, J=8.6 Hz), 3.00–3.20 (1H, m), 3.63–3.72 (2H, m), 4.04 (1H, d, J=8.7 Hz), 7.13–7.43 (10H, m)

MASS (APCI): 434 (M+H)$^+$ (free)

Preparation 57

10% Palladium-charcoal (50% wet, 40 mg) and 0.1N hydrochloric acid (0.1 ml) were added into a solution of tert-butyl (4R,7R,8aS)-7-azido-4-benzhydrylhexahydropyrrolo[1,2-a]pyrazine-2(1H)-carboxylate (200 mg) in methanol (2.5 ml) at room temperature. The mixture was hydrogenated at room temperature under atmospheric pressure for 4 hours. The palladium was filtered and washed with methanol. The filtrate and washings were combined and concentrated in vacuo. The resulting residue was partitioned between aqueous sodium hydrogen carbonate and ethyl acetate. The organic layer was separated, dried over magnesium sulfate and evaporated under reduced pressure. The resulting residue was purified by silica gel column chromatography with a mixture of dichloromethane and methanol (15:1) as an eluent. The fractions containing the objective compound were collected to give tert-butyl (4R,7R,8aS)-7-amino-4-benzhydrylhexahydropyrrolo[1,2-a]pyrazine-2(1H)-carboxylate (193 mg).

NMR (CDCl$_3$, δ): 1.22–1.65 (15H, m), 2.30–2.51 (3H, m), 3.00–3.40 (2H, m), 3.68–4.10 (3H, m), 7.13–7.42 (10H, m)

MASS (APCI): 408 (M+H)$^+$

Preparation 58

The following compound was obtained according to a similar manner to that of Preparation 57.

Tert-Butyl (4R,7S,8aS)-7-amino-4-benzhydrylhexahydropyrrolo[1,2-a]pyrazine-2(1H)-carboxylate IR (KBr): 3300–3100, 1697 cm$^{-1}$ NMR (CDCl$_3$, δ): 1.00–1.10 (1H, m), 1.38(9H, s), 1.80–3.80 (10H, m), 4.07 (1H, d, J=8.0 Hz), 7.13–7.40 (10H, m)

MASS (APCI): 408 (M+H)$^+$

Preparation 59

Sodium triacetoxyborohydride (241 mg) was added to an ice-cooled solution of tert-butyl (4R,7S,8aS)-7-amino-4-benzhydrylhexahydropyrrolo[1,2-a]pyrazine-2(1H)-carboxylate (0.23 g) and aqueous 30% formaldehyde (0.17 ml) in dichloromethane (10 ml). After being stirred for 15 hours at room temperature the mixture was washed with aqueous saturated sodium hydrogen carbonate, dried over magnesium sulfate and concentrated under reduced pressure. The syrup was purified by column chromatography on silica gel using a mixed solvent of dichloromethane and methanol (40:1). The fractions containing the objective compound were collected to give tert-butyl (4R,7S,8aS)-4-benzhydryl-7-(dimethylamino)hexahydropyrrolo[1,2-a]pyrazine-2(1H)-carboxylate (210 mg).

NMR (CDCl$_3$, δ): 1.20–1.40 (1H, m), 1.37 (9H, s), 1.90–4.20 (10H, m), 2.06 (6H, s), 4.06 (1H, d, J=8.0 Hz), 7.13–7.41 (10H, m)

MASS (APCI): 436 (M+H)$^+$

Preparation 60

The following compound was obtained according to a similar manner to that of Preparation 3.

N-[(4R,7S,8aS)-4-Benzhydryloctahydropyrrolo[1,2-a]pyrazin]-7-N,N-dimethylamine trihydrochloride IR (KBr): 3400, 1648, 1504 cm$^{-1}$ NMR (DMSO-d$_6$, δ): 1.50–4.10 (15H, m), 4.26 (1H, d, J=9.0 Hz), 7.20–7.43 (10H, m), 9.20–9.60 (3H, m), 10.91 (1H, br s)

MASS (APCI): 336 (M+H)$^+$ (free)

Preparation 61

A solution of benzyl chloroformate (58 μl) in dichloromethane (0.5 ml) was added dropwise to an ice-cooled solution of tert-butyl (4R,7S,8aS)-7-amino-4-benzhydrylhexahydropyrrolo[1,2-a]pyrazine-2(1H)-carboxylate and triethylamine (96 μl) in dichloromethane (2 ml), and the whole was stirred for 2 hours at the same temperature. The mixture was poured into water and extracted with dichloromethane. The organic layer was separated, dried over magnesium sulfate and concentrated under reduced pressure. The syrup was purified by column chromatography on silica gel using a mixed solvent of hexane and ethyl acetate (4:1). The fractions containing the objective compound were collected to give tert-butyl (4R,7S,8aS)-4-benzhydryl-7-[(benzyloxycarbonyl)amino]hexahydropyrrolo[1,2-a]pyrazine-2(1H)-carboxylate (190 mg) as a syrup.

NMR (CDCl$_3$, δ): 1.00–1.20 (1H, m), 1.37 (9H, s), 2.00–2.70 (6H, m), 3.00–3.10 (1H, m), 3.70–4.20 (3H, m), 4.02 (1H, d, J=8.0 Hz), 4.98 (1H, d, J=8.6 Hz), 5.06 (2H, s), 7.13–7.40 (15H, m)

MASS (APCI): 542 (M+H)$^+$

Preparation 62

The following compound was obtained according to a similar manner to that of preparation 3.

Benzyl (4R,7S,8aS)-4-benzhydryloctahydropyrrolo[1,2-a]pyrazin-7-ylcarbamate dihydrochloride NMR (CDCl$_3$, δ): 1.40–5.10 (15H, m), 4.60 (2H, s), 7.16–7.80 (13H, m), 8.21 (1H, br s)

MASS (APCI): 442 (M+H)$^+$ (free)

Preparation 63

(Dimethylamino)sulfur trifluoride (0.068 ml) was added dropwise to a solution of tert-butyl (4R,7R,8aS)-4-benzhydryl-7-hydroxyhexahydropyrrolo[1,2-a]pyrazine-2(1H)-carboxylate (115 mg) in dichloromethane (2 ml) under cooling with dry ice-acetone. The mixture was stirred for 20 minutes at the same temperature (−50° C.), followed by room temperature for 2 hours. The mixture was poured into ice-water and the dichloromethane layer was separated, dried over magnesium sulfate, and evaporated under reduced pressure. The syrup was purified by column chromatography on silica gel using a mixed solvent of hexane and ethyl acetate (2:1). The fractions containing the objective compound were collected and evaporated under reduced pressure. The resulting syrup was treated with 4N hydrogen chloride in ethyl acetate (2 ml) and evaporated under reduced pressure to give (4R,7S,8aS)-4-benzhydryl-7-fluorooctahydropyrrolo[1,2-a]pyrazine dihydrochloride (75 mg).

MASS (APCI): 311 (M+H)$^+$, 333 (M+Na) (free)

Preparation 64

Triphenylphosphine (860 mg), acetic acid (159 mg) and diisopropyl azodicarboxylate were added successively into a solution of tert-butyl (4R,7R,8aS)-4-benzhydryl-7-hydroxyhexahydropyrrolo[1,2-a]pyrazine-2(1H)-carboxylate (670 mg) in tetrahydrofuran (10 ml) at room temperature. After being stirred for 1 hour at room temperature, the reaction mixture was poured into aqueous saturated sodium hydrogen carbonate. The whole was extracted with ethyl acetate. The extract was washed with brine, dried over magnesium sulfate and evaporated under reduced pressure. The resulting residue was purified by silica gel column chromatography with a mixture of hexane and ethyl acetate (2:1–3:2) as an eluent to give tert-butyl (4R,7S,8aS)-7-acetoxy-4-benzhydrylhexahydropyrrolo[1,2-a]pyrazine-2(1H)-carboxylate.

NMR (CDCl$_3$, δ): 1.30–1.43 (11H, m), 2.01–2.04 (3H, m), 2.08–2.79 (6H, m), 3.12 (1H, m), 3.77–4.10 (2H, m), 4.89–5.01 (1H, m), 6.71–7.42 (10H, m)

MASS (APCI): 451 (M+H)$^+$

Preparation 65

Sodium methoxide in methanol (5M, 27 μl) was added into a solution of tert-butyl (4R,7S,8aS)-7-acetoxy-4-benzhydrylhexahydropyrrolo[1,2-a]pyrazine-2(1H)-carboxylate (628 mg) in methanol (10 ml) at room temperature. After being stirred for 1 hour at the same temperature, the reaction mixture was poured into water (10 ml). The whole was extracted with ethyl acetate. The extract was washed with brine, dried over magnesium sulfate and evaporated under reduced pressure. The resulting residue was purified by silica gel column chromatography with a mixture of hexane and ethyl acetate (1:1) as an eluent to give tert-butyl (4R,7S,8aS)-4-benzhydryl-7-hydroxyhexahydropyrrolo[1,2-a]pyrazine-2(1H)-carboxylate (521 mg).

NMR (CDCl$_3$, δ): 1.20–1.38 (11H, m), 1.80–1.98 (2H, m), 2.14–2.33 (2H, m), 2.43–2.74 (3H, m), 3.10 (1H, br), 3.73 (1H, br), 4.04–4.09 (2H, m), 7.14–7.41 (10H, m)

MASS (APCI): 409 (M+H)$^+$

Preparation 66

Sodium hydride (60% in mineral oil, 14.9 mg) was added into a solution of tert-butyl (4R,7S,8aS)-4-benzhydryl-7-hydroxyhexahydropyrrolo[1,2-a]pyrazine-2(1H)-carboxylate (126.8 mg) in N,N-dimethylformamide (1.5 ml) under ice-cooling. After being stirred for 0.5 hour at the same temperature, methyl iodide was added to the reaction mixture. And this mixture was stirred for 12 hours at room temperature. Then the reaction mixture was poured into water (10 ml). The aqueous layer was extracted with ethyl acetate. The combined extracts were washed with brine, dried over magnesium sulfate and evaporated under reduced pressure. The resulting residue was purified by silica gel column chromatography with a mixture of hexane and ethyl acetate (1:2) as an eluent to give tert-butyl (4R,7S,8aS)-4-benzhydryl-7-methoxyhexahydropyrrolo[1,2-a]pyrazine-2 (1H)-carboxylate (100.5 mg).

NMR (CDCl$_3$, δ): 1.38 (11H, br), 1.80–1.88 (1H, m), 2.04–2.80 (5H, m), 3.14 (3H, s), 3.63–4.18 (4H, m), 7.14–7.45 (10H, m)

MASS (APCI): 423 (M+H)$^+$

Preparation 67

The following compound was obtained according to a similar manner to that of Preparation 63 from tert-butyl (4R,7S,8aS)-4-benzhydryl-7-hydroxyhexahydropyrrolo[1,2-a]pyrazine-2(1H)-carboxylate.

Tert-Butyl (4R,7R,8aS)-4-benzhydryl-7-fluorohexahydropyrrolo[1,2-a]pyrazine-2 (1H)-carboxylate NMR (CDCl$_3$, δ): 1.22–2.58 (15H, m), 3.12–4.18 (2H, m), 3.79–4.18 (3H, m), 4.84–5.14 (1H, m), 7.15–7.42 (10H, m)

MASS (APCI): 411 (M+H)$^+$

Preparation 68

The following compound was obtained according to a similar manner to that of Preparation 3.

(4S,7R,8aS)-4-Benzhydryl-7-methoxyoctahydropyrrolo[1,2-a]pyrazine dihydrochloride MASS (APCI): 323 (M+H)$^+$ (free)

Preparation 69

The following compound was obtained according to a similar manner to that of Preparation 46 from tert-butyl (2S,3S)-3-hydroxy-2-(N-methoxy-N-methylcarbamoyl)-1-pyrrolidinecarboxylate.

Tert-Butyl (2S,3S)-2-formyl-3-hydroxy-1-pyrrolidinecarboxylate

NMR (CDCl$_3$, δ): 1.47 (9H, s), 1.89–2.04 (1H, m), 3.43–4.48 (6H, m), 9.68 (1H, d)

MASS (ESI): 238 (M+Na)

Preparation 70

The following compound was obtained according to a similar manner to that of Preparation 25 from tert-butyl (2S,3S)-2-formyl-3-hydroxy-1-pyrrolidinecarboxylate.

Tert-Butyl (2R,3S)-3-hydroxy-2-[[(2-methoxybenzyl)amino]ethyl]-1-pyrrolidinecarboxylate NMR (CDCl$_3$, δ): 1.47 (9H, m), 1.70–2.20 (5H, m), 2.99–4.52 (5H, m), 3.85 (3H, m), 6.85–6.95 (2H, m), 7.20–7.31 (4H, m)

MASS (APCI): 337 (M+1)

Preparation 71

The following compound was obtained according to a similar manner to that of Preparation 17 from tert-butyl (2R,3S)-3-hydroxy-2-[[(2-methoxybenzyl)amino]methyl]-1-pyrrolidinecarboxylate.

Tert-Butyl (2R,3S)-3-hydroxy-2-[N-(2-methoxybenzyl)-N-(2-oxo-3,3-diphenylpropyl)amino]methyl]-1-pyrrolidinecarboxylate NMR (CDCl$_3$, δ): 1.41 (9H, m), 1.67–1.80 (3H, m), 2.63–4.18 (9H, m), 5.19 (1H, s), 6.87 (2H, m), 6.84–7.30 (16H, m)

MASS (APCI): 545 (M+1)

Preparation 72

To a solution of (4R,9aR)-8-acetyl-4-benzhydryl-2-(2-methoxybenzyl)octahydro-2H-pyrazino[1,2-a]pyrazine (5.9 g) in dichloroethane (60 ml) was added 1-chloroethyl chloroformate (2.3 ml) at room temperature, and the reaction mixture was heated at 70° C. for 30 minutes with stirring. After removal of solvent by evaporation, to the resulting residue was added methanol (45 ml), and the solution was refluxed for 40 minutes. After being concentrated, the residue was triturated with diisopropyl ether. The resulting precipitate was collected by filtration and dried under, reduced pressure for 5 hours at 40° C. to give (4R,9aR)-8-acetyl-4-benzhydryloctahydro-2H-pyrazino[1,2-a]pyrazine dihydrochloride (3.1 g) as colorless foam.

NMR (DMSO-d$_6$, δ): 1.90–2.00 (3H, m), 2.20–4.70 (13H, m), 7.10–7.50 (10H, m), 9.65 (2H, br)

MASS (APCI): 350 (M+H)$^+$ (free)

Preparation 73

Under nitrogen atmosphere, to a solution of 5-bromo-2-methoxybenzaldehyde (350 mg) in dimethoxyethane (3.5 ml) were added 3-thiopheneboronic acid (417 mg), tetrakis(triphenylphosphine)palladium (0) (282 mg), and 2M sodium carbonate (4.9 ml) at room temperature. After being heated at 80° C. with stirring for 5 hours, the reaction mixture was poured into mixed solvents of ethyl acetate and water. The organic layer was separated, washed with brine, dried over magnesium sulfate, and concentrated under reduced pressure. The resulting residue was purified by column chromatography on silica gel (6 g) using a mixed solvent of hexane and ethyl acetate (10:1). The fractions containing the objective compound were collected and evaporated under reduced pressure to give 2-methoxy-5-(3-thienyl)benzaldehyde (290 mg) as yellowish oil.

IR (Neat): 3103, 2941, 2854, 1682, 1610, 1495, 1255, 1174 cm$^{-1}$

NMR (CDCl$_3$, δ): 3.96 (3H, s), 7.03 (1H, d, J=8.7 Hz), 7.30–7.50 (3H, m), 7.79 (1H, dd, J=2.5 Hz, J=8.7 Hz), 8.06 (1H, d, J=2.5 Hz), 10.50 (1H, s)

MASS (APCI): 219 (M+H)$^+$

Preparation 74

A solution of 1-fluoro-2-methyl-4-nitrobenzene (10 g) in methanol (200 ml) was hydrogenated over 10% palladium-charcoal (50% wet, 1.0 g) at room temperature under atmospheric pressure for 8 hours. After removal of the catalyst by filtration, the filtrate was evaporated under reduced pressure to give a syrup. The syrup was dissolved into dichloromethane (200 ml) and thereto triethylamine (16.2 ml) and trifluoroacetic anhydride (14.9 g) were added dropwise. The whole mixture was stirred for 5 hours at room temperature and then washed with water and brine successively. The organic layer was separated, dried over magnesium sulfate, and evaporated under reduced pressure to give 2,2,2-trifluoro-N-(4-fluoro-3-methylphenyl)acetamide (14.5 g).

NMR (CDCl$_3$, δ): 2.28 (3H, d, J=2.0 Hz), 6.96–7.05 (1H, m), 7.31–7.46 (1H, m), 8.09 (1H, br s)

MASS (APCI): 244 (M+Na)$^+$

Preparation 75

A mixture of 2,2,2-trifluoro-N-(4-fluoro-3-methylphenyl)acetamide (14.3 g) and triphenylphosphine (19.5 g) in tetrachloromethane (140 ml) was stirred for 17 hours at 100° C. An additional triphenylphosphine (5 g) was added to the mixture and the whole was stirred for 5 hours and finally triphenylphosphine (5 g) was added to the mixture, and the whole was stirred further for 15 hours at 100° C. After being cooled to room temperature hexane was added to the reaction mixture and the whole was stirred for 0.5 hour under ice-cooling. The resulting precipitate was removed by filtration and washed with hexane. The combined filtrate and washing were evaporated under reduced pressure below 20° C. A mixture of the syrup obtained and sodium azide (10.6 g) in acetic acid (100 ml) was stirred at room temperature for 7 hours, followed by at 70° C. for 17 hours. After being cooled to room temperature, the mixture was poured into ice-water, and extracted with dichloromethane. The organic layer was separated, dried over magnesium sulfate, and evaporated under reduced pressure. The syrup was purified by column chromatography on silica gel using a mixed solvent of hexane and ethyl acetate (100:1–5:1). The fractions containing the objective compound were collected to give 1-(4-fluoro-3-methylphenyl)-5-(trifluoromethyl)-1H-tetrazole (15.2 g) as a syrup.

NMR (CDCl$_3$, δ): 2.40 (3H, d, J=2.0 Hz), 7.19–7.63 (3H, m)

MASS: 247 (M+H)$^+$ 219

Preparation 76

2,2'-Azobis(4-methoxy-2,4-dimethylvaleronitrile) (50 mg) was added by three portions to the mixture of 1-(4-fluoro-3-methylphenyl)-5-(trifluoromethyl)-1H-tetrazole and N-bromophtalimide (1.44 g) in dichloromethane (16 ml) at 30° C. and the whole was stirred at reflux for 3 hours. After being cooled to room temperature, the mixture was washed with aqueous sodium hydrogen carbonate and aqueous sodium thiosulfate successively. The organic layer was separated, dried over magnesium sulfate, and evaporated under reduced pressure to give a crude 1-[3-(bromomethyl)-4-fluorophenyl]-5-(trifluoromethyl)-1H-tetrazole (3:7).

NMR (CDCl$_3$, δ): 4.54 (2H, d, J=1.0 Hz), 7.19–7.63 (3H, m)

Preparation 77

To a solution of (2S)-2-ethoxycarbonylpiperazine-1-carboxylic acid 1-tert-butyl ester D-tartarate (9.56 g) in tetrahydrofuran (90 ml) and water (90 ml) was added sodium bicarbonate (7.87 g) under ice-cooling. Benzyl chloroformate (4.01 ml) was added dropwise to the solution over 2 minutes at the same temperature, and stirred at room temperature for 15 minutes. Ethyl acetate (60 ml) and sodium chloride (5 g) was added to the mixture. The organic layer was washed with brine, dried over magnesium sulfate, and evaporated under reduced pressure to give (2S)-2-ethoxycarbonylpiperazine-1,4-dicarboxylic acid 4-benzyl ester 1-tert-butyl ester (10.4 g) as a colorless oil.

NMR (CDCl$_3$, δ): 1.10–1.60 (12H, m), 2.60–4.80 (9H, m), 5.00–5.30 (2H, m), 7.20–7.40 (5H, m)

MASS (API-ES): 415 (M+Na)$^+$

Preparation 78

Under nitrogen atmosphere, to a solution of (2S)-2-ethoxycarbonylpiperazine-1,4-dicarboxylic acid 4-benzyl ester 1-tert-butyl ester (9.35 g) was added portionwise lithium borohydride (1.82 g), and the reaction mixture was stirred for 90 minutes. After methanol (2.32 ml) was added dropwise to the solution under ice-cooling, the mixture was stirred at room temperature for 17 hours. 1N Hydrochloric acid (80 ml) was added dropwise under ice-cooling, and ethyl acetate (100 ml) and sodium chloride (6 g) was added to it. The organic layer was washed with brine, dried over magnesium sulfate, and evaporated under reduced pressure to give colorless oil. The oil was purified by column chromatography on silica gel (90 g) using a mixed solvent of hexane and ethyl acetate (3:2). The fractions containing the objective compound were collected and evaporated under reduced pressure to give (2S)-2-(hydroxymethyl)piperazine-1,4-dicarboxylic acid 4-benzyl ester 1-tert-butyl ester (8.40 g) as a colorless oil.

NMR (CDCl$_3$, δ): 1.46 (9H, s), 2.40–4.30 (10H, m), 5.10–5.30 (2H, m), 7.30–7.50 (5H, m)

MASS (API-ES): 373 (M+Na)$^+$

Preparation 79

Under nitrogen atmosphere, to a solution of oxalyl chloride (1.64 ml) in dichloromethane (34 ml) under –65° C., was added dropwise a solution of dimethyl sulfoxide (2.0 ml) in dichloromethane (15 ml) and stirred for 10 minutes at the same temperature. A solution of (2S)-2-(hydroxymethyl)piperazine-1,4-dicarboxylic acid 4-benzyl ester 1-tert-butyl ester (3.29 g) in dichloromethane (24 ml) was dropped into the above solution over 5 minutes under –65° C. The reaction mixture was stirred at the same temperature for 15 minutes, then stirred at –45° C. for 90 minutes. Triethylamine (7.85 ml) was added to the solution under –40° C., and the mixture was stirred at 0° C. for 20 minutes. The mixture was poured into saturated aqueous ammonium chloride (100 ml). The organic layer was washed with brine, dried over magnesium sulfate, and evaporated to give (2R)-2-formylpiperazine-1,4-dicarboxylic acid 4-benzyl ester 1-tert-butyl ester (3.33 g) as a colorless syrup.

NMR (CDCl$_3$, δ): 1.40–1.70 (9H, m), 2.85–3.30 (3H, m), 3.70–4.80 (4H, m), 5.05–5.30 (2H, m), 7.30–7.40 (5H, m), 9.58 (1H, s)

MASS (API-ES): 371 (M+Na)$^+$

Preparation 80

A solution of 3-bromo-1,1-diphenyl-2-propanone (0.5 g) in tetrahydrofuran (10 ml) was added to a mixture of (2-methoxy-benzyl)amine (1.13 ml) and N,N-diisopropylethylamine (0.602 ml) in tetrahydrofuran (12 ml) over 0.5 hour at room temperature. After being stirred at room temperature for 1.5 hours, the mixture was concentrated under reduced pressure to half volume and the resulting mixture was poured into ice-water (10 ml) and extracted with ethyl acetate (10 ml×2). The extract was washed with brine, dried over magnesium sulfate and evaporated under reduced pressure to give 3-[(2-methoxybenzyl)amino]-1,1-diphenylpropan-2-one (483 mg) as a colourless syrup.

NMR (CDCl$_3$, δ): 3.63 (2H, s), 3.73 (2H, s), 3.79 (3H, s), 5.13 (1H, s), 6.82–7.36 (14H, m)

MASS (APCI): 346 (M+H)$^+$

Preparation 81

Under nitrogen atmosphere, to a solution of (2R)-2-formylpiperazine-1,4-dicarboxylic acid 4-benzyl ester 1-tert-butyl ester (2.64 g) and 3-(2-methoxybenzylamino)-1,1-diphenylpropan-2-one (3.66 g) in dichloromethane (30 ml) was added acetic acid (0.607 ml) and sodium tritacetoxyborohydride (4.82 g) under ice-cooling, and then it was stirred at room temperature for 3 hours. The reaction mixture was poured into aqueous sodium hydrogen carbonate (100 ml) and extracted with dichloromethane. The organic layer was washed with brine, dried over sodium sulfate, and evaporated under reduced pressure. The resulting residue was purified by column chromatography on silica gel (82 g) using a mixed solvent of hexane and ethyl acetate (3:1). The fractions containing the objective compound were collected and evaporated under reduced pressure to give (2S)-2-[[N-(2-methoxybenzyl)-N-(2-oxo-3,3-diphenylpropyl)amino]methyl]piperazine-1,4-dicarboxylic acid 4-benzyl ester 1-tert-butyl ester (3.24 g) as a syrup.

NMR (CDCl$_3$, δ): 1.40–1.65 (9H, m), 2.65–5.40 (19H, m), 6.70–7.40 (19H, m)

MASS (APCI): 678 (M+H)$^+$

Preparation 82

The following compound was obtained according to a similar manner for Preparation 72.

(4R,9aS)-4-Benzhydryl-8-(benzyloxycarbonyl)octahydro-2H-pyrazino-[1,2-a]pyrazine dihydrochloride NMR (DMSO-$d_6$, δ): 2.20–5.00 (13H, m), 5.07 (2H, s), 7.15–7.45 (15H, m), 9.53 (2H, br)

MASS (APCI): 442 (M+H)$^+$ (free)

Preparation 83

The following compound was obtained according to a similar manner to that of Preparation 34.

Benzyl [1-(N-methoxy-N-methylcarbamoyl)cyclopentyl]carbamate

NMR (CDCl$_3$, δ): 1.61–1.74 (4H, m), 1.86–2.00 (2H, m), 2.22–2.40 (2H, m), 3.13 (3H, s), 3.53 (3H,. s), 5.07 (1H, br s), 5.10 (2H, s), 7.29–7.35 (5H, m)

MASS (APCI): 635 (2M+Na), 329 (M+Na)$^+$

Preparation 84

The following compounds were obtained according to a similar manner to that of Preparation 35.

(1) Benzyl (1-formylcyclopentyl)carbamate

NMR (CDCl$_3$, δ): 1.61–2.17 (8H, m), 5.10 (2H, s), 5.26 (1H, br s), 7.29–7.35 (5H, m), 9.53 (1H, s)

MASS (APCI): 204, 248 (M+H)$^+$ (2) Benzyl [1-[(benzylamino)methyl]cyclopentyl]carbamate NMR (CDCl$_3$, δ): 1.50–2.04 (9H, m), 2.76 (2H, s), 3.79 (2H, s), 5.05 (2H, s), 5.18 (1H, br s), 7.20–7.35 (10H, m)

MASS (APCI): 339 (M+H)$^+$, 231

(3) Benzyl [1-[[N-benzyl-N-(2-oxo-3,3-diphenylpropyl)amino]methyl]cyclopentyl]carbamate NMR (CDCl$_3$, δ): 1.50–2.04 (8H, m), 2.92 (2H, s), 3.48 (2H, s), 3.75 (2H, s), 4.90–5.00 (4H, s), 7.20–7.35 (20H, m)

MASS (APCI): 547 (M+H)$^+$, 406

Preparation 85

The following compound was obtained according to a similar manner to that of Preparation 18.

7-Benzhydryl-6,9-diazaspiro[4.5]decane

MASS (APCI): 307 (M+H)$^+$ (free)

Preparation 86

The following compound was obtained according to a similar manner to that of Preparation 35.

Benzyl [2-(benzylamino)-1,1-dimethylethyl]carbamate

NMR (CDCl$_3$, δ): 1.28 (6H, s), 2.63 (1H, s), 3.81 (2H, s), 3.79 (2H, s), 5.04 (2H, s), 5.42 (1H, br s), 7.20–7.35 (10H, m)

MASS (APCI): 313 (M+H)$^+$

Preparation 87

The following compound was obtained according to a similar manner to that of Preparation 17.

Benzyl [2-[N-benzyl-N-(2-oxo-3,3-iphenylpropyl)amino]-1,1-dimethylethyl]carbamate NMR (CDCl$_3$, δ) 1.28 (6H, s), 2.77 (2H, s), 3.53 (2H, s), 3.78 (2H, s), 5.00 (2H, s), 5.44 (1H, br s), 7.20–7.35 (20H, m)

MASS (APCI): 521 (M+H)$^+$, 413

Preparation 88

The following compound was obtained according to a similar manner to that of Preparation 18.

6-Benzhydryl-2,2-dimethylpiperazine

IR (KBr): 3400, 1648, 1504 cm$^{-1}$

NMR (DMSO-$d_6$, δ): 0.96 (3H, s), 1.29 (3H, s), 2.28–2.39 (1H, m), 2.53 (1H, d, J=12.2 Hz), 2.60 (1H, d, J=12.2 Hz), 2.72 (1H, d, J=11.0 Hz), 3.62–3.74 (2H, m), 7.14–7.38 (10H, m)

MASS (APCI): 281 (M+H)$^+$ (free)

Preparation 89

The following compound was obtained according to a similar manner to that of Example 4.

2-[2-Benzhydryl-4-[2-methoxy-5-[5-(trifluoromethyl)-1H-tetrazol-1-yl]benzyl]-1-piperazinyl]acetic acid

MASS (APCI): 567 (M+H)$^+$

Dihydrochloride of the above compound

IR (KBr, FT-IR): 1615, 1440, 1320, 1265, 1235 cm$^{-1}$

NMR (DMSO-$d_6$, δ): 2.70–5.15 (12H, m), 3.84 (3H, s), 7.10–8.10 (13H, m), 10.36 (1H, br s)

MASS (APCI): 567 (M+H)$^+$ (free)

Preparation 90

Sodium triacetoxyborohydride (163 mg) was added to a mixture of bis(acetic acid) salt of (7R,8aS)-4-benzhydryl-7-[(tert-butyldimethylsilyl)oxy]octahydropyrrolo[1,2-a]pyrazine (0.38 g) and 2-methoxy-5-[5-(trifluoromethyl)-1H-tetrazol-1-yl]benzaldehyde (210 mg) in dichloromethane, and the whole was stirred for 3 hours at room temperature. The mixture was washed with aqueous sodium hydrogen carbonate, dried over magnesium sulfate and concentrated under reduced pressure. The syrup was purified by column chromatography on silica gel using a mixed solvent of hexane and ethyl acetate (4:1). The later eluting fractions were collected and evaporated under reduced pressure to give colorless oil of (4R,7R,8aS)-4-benzhydryl-7-[(tert-butyldimethylsilyl)oxy]-2-[2-methoxy-5-[5-(trifluoromethyl)-1H-tetrazol-1-yl]benzyl]-octahydropyrrolo[1,2-a]pyrazine (0.18 g).

NMR (CDCl$_3$, δ): −0.20 (3H, s), −0.11 (3H, m), 0.75 (9H, m), 1.58–1.74 (4H, m), 2.18 (1H, dd, J=4.7 and 9.6 Hz), 2.26 (1H, dd, J=3.3 and 11.3 Hz), 2.31 (1H, d, J =11.3 Hz), 2.69 (1H, dd, J=3.0 and 10.6 Hz), 2.96 (1H, dd, J=6.7 and 9.5 Hz), 3.25 (1H, d, J=14.8 Hz), 3.30–3.50 (1H, m), 3.69 (1H, d, J=10.6 Hz), 3.87 (3H, s), 4.20–4.25 (1H, m), 4.66 (1H, d, J=10.8 Hz), 6.94–7.40 (12H, m), 7.54 (1H, d, J=2.6 Hz)

MASS (APCI-ES): 679 (M+H)$^+$

The earlier eluting fractions were collected and evaporated under reduced pressure to give colorless oil of (4S,7R,8aS)-4-benzhydryl-7-[(tert-butyldimethylsilyl)oxy]-2-[2-methoxy-5-[5-(trifluoromethyl)-1H-tetrazol-1-yl]benzyl]octahydropyrrolo[1,2-a]pyrazine (0.15 g).

NMR (CDCl$_3$, δ): −0.20 (3H, s), −0.11 (3H, m), 0.75 (9H, m), 1.56–1.95 (6H, m), 2.47 (1H, d, J=11.2 Hz), 2.64–2.92 (2H, m), 3.36–3.60 (3H, m), 2.78 (3H, s), 3.92 (1H, d, J=11.1 Hz), 4.07–4.17 (1H, m), 6.92 (1H, d, J=8.8 Hz), 7.05–7.45 (12H, m)

MASS (APCI-ES): 679 (M+H)$^+$ (free)

Preparation 91

The following compound was obtained according to a similar manner to that of Preparation 56 from (4R,8S,8aR)-4-benzhydryl-2-[2-methoxy-5-[5-(trifluoromethyl)-1H-tetrazol-1-yl]benzyl]octahydropyrrolo[1,2-a]pyrazin-8-ol.

(4R,8R,8aR)-8-Azido-4-benzhydryl-2-[2-methoxy-5-[5-(trifluoromethyl)-1H-tetrazol-1-yl]benzyl]octahydropyrrolo[1,2-a]pyrazine

MASS (APCI): 590 (M+1)

Preparation 92

The following compound was obtained according to a similar manner to that of Preparation 64 from (4R,8S,8aR)-4-benzhydryl-2-[2-methoxy-5-[5-(trifluoromethyl)-1H-tetrazol-1-yl]benzyl]octahydropyrrolo[1,2-a]pyrazin-8-ol.

(4R,8R,8aR)-4-Benzhydryl-2-[2-methoxy-5-[5-(trifluoromethyl)-1H-tetrazol-1-yl]benzyl]octahydropyrrolo[1,2-a]pyrazin-8-yl acetate NMR (CDCl$_3$, δ): 1.91–2.23 (5H, m), 2.03 (3H, s), 2.43 (2H, br), 2.63–2.89 (2H, m), 3.24 (1H, br), 3.42–3.64 (2H, d×2, J=15 Hz), 3.78 (3H, s), 4.09 (1H, m), 5.18 (1H, m), 6.90–7.42 (13H, m)

MASS (APCI): 607 (M+1)

Preparation 93

The following compound was obtained according to a similar manner to that of Preparation 56 from (4R,8R,8aR)-4-benzhydryl-2-[2-methoxy-5-[5-(trifluoromethyl)-1H-tetrazol-1-yl]benzyl]octahydropyrrolo[1,2-a]pyrazin-8-ol.

(4R,8S,8aR)-8-Azido-4-benzhydryl-2-[2-methoxy-5-[5-(trifluoromethyl)-1H-tetrazol-1-yl]benzyl]octahydropyrrolo[1,2-a]pyrazine MASS (APCI): 590 (M+1) (free)

Preparation 94

To a mixture of (4R,9aS)-4-benzhydryl-2-[2-methoxy-5-[5-(trifluoromethyl)-1H-tetrazol-1-yl]benzyl]octahydro-2H-pyrazino[1,2-a]pyrazine trihydrochloride (80 mg), cyclopentanecarboxylic acid (16.9 µl), 1-hydroxybenzotriazole hydrate (23 mg), and triethylamine (79 µl) in dichloromethane (1 ml) was added 1-[3-(dimethylamino)propyl]-3-ethylcarbodiimide hydrochloride at room temperature. After stirring at room temperature overnight, the mixture was quenched with aqueous saturated sodium hydrogen carbonate and extracted with dichloromethane. The extract was dried over magnesium sulfate and evaporated under reduced pressure. The residue was purified with preparative TLC (methanol/chloroform=1/9) to give an oil. To a solution of the oil in ethyl acetate (1 ml) was added 4N hydrogen chloride in ethyl acetate (0.2 ml) and hexane (20 ml). After stirring for 30 minutes, the precipitate was collected by filtration and dried under reduced pressure at 50° C. for 5 hours to give (4R,9aR)-4-benzhydryl-8-cyclopentanecarbonyl-2-[2-methoxy-5-[5-(trifluoromethyl)-1H-tetrazol-1-yl]benzyl]octahydro-2H-pyrazino[1,2-a]pyrazine dihydrochloride (63.9 mg) as a powder.

mp: 170–178° C., decomp.

$[\alpha]_D^{27}$: −37.83 (C, 0.115, MeOH)

IR (KBr) 1647 cm$^{-1}$

NMR (DMSO-d$_6$, δ) 1.40–1.80 (8H, m), 2.20–4.50 (16H, m), 3.80 and 3.82 (total 3H, s), 7.15–7.82 (13H, m)

MASS (APCI+): 660.2 (MH+) (free)

EXAMPLE 1

A mixture of 3-benzhydryl-1-(2-methoxybenzyl)piperazine dihydrochloride (44.5 mg), bromoacetamide (20.7 mg) and potassium carbonate (41.5 mg) in N,N-dimethylformamide (5 ml) was stirred at room temperature for 18 hours. The mixture was partitioned between ethyl acetate and 2N sodium hydroxide. The organic layer was separated, washed with brine, dried over sodium sulfate and evaporated under reduced pressure. The resulting residue was purified by column chromatography on silica gel using a mixed solvent of dichloromethane and methanol (70:1). The fractions containing the objective compound were collected, evaporated under reduced pressure and treated with 4N hydrogen chloride in ethyl acetate solution to give 2-benzhydryl-1-carbamoylmethyl-4-(2-methoxybenzyl)piperazine dihydrochloride (21.6 mg) as a colorless powder.

NMR (DMSO-d$_6$, δ): 2.79–4.20 (14H, m), 5.08 (1H, d, J=12.3 Hz), 5.85–5.96 (2H, m), 6.83–7.63 (14H, m), 10.05–10.32 (2H, m)

MASS (APCI): 430 M+H)$^+$ (free)

EXAMPLE 2

Sodium triacetoxyborohydride (127 mg) was added portionwise to a mixture of 2-benzhydrylpiperazine dihydrochloride (97.6 mg), N,N-diisopropylethylamine (0.104 ml) and 2-methoxy-5-[5-(trifluoromethyl)tetrazol-1-yl]benzaldehyde (61.2 mg) in a mixture of dichloromethane (5 ml) and acetic acid (1 drop) at 0° C. and the whole was stirred at 5° C.~room temperature overnight. The mixture was partitioned between ethyl acetate and 2N sodium hydroxide. The organic layer was separated, washed with brine, dried over sodium sulfate and evaporated under reduced pressure. The resulting residue was purified by column chromatography on silica gel using a mixed solvent of dichloromethane and methanol (70:1). The fractions containing the objective compound were collected, evaporated under reduced pressure and treated with 4N hydrogen chloride in ethyl acetate solution to give 3-benzhydryl-1-[2-methoxy-5-[5-(trifluoromethyl)-1H-tetrazol-1-yl]benzyl]piperazine dihydrochloride (74 mg) as a colorless powder.

NMR (DMSO-d$_6$, δ): 2.60–4.81 (14H, m), 7.17–7.50 (11H, m), 7.22–7.75 (2H, m)

MASS (APCI): 509 (M+H)$^+$ (free)

EXAMPLE 3

The following compounds were obtained according to a similar manner to that of Example 2.

(1) 3-Benhydryl-1-(2-methoxybenzyl)piperazine dihydrochloride

NMR (DMSO-d$_6$, δ): 2.60–4.71 (14H, m), 6.92–7.03 (2H, m), 7.29–7.46 (12H, m)

MASS (APCI): 373 (M+H)$^+$ (free)

(2) 3-Benzhydryl-1-[2-methoxy-5-(trifluoromethoxy)benzyl]piperazine dihydrochloride NMR (DMSO-d$_6$, δ): 2.80–4.73 (14H, m), 7.07–7.51 (13H, m)

MASS (APCI): 457 (M+H)$^+$ (free)

(3) 3-Benzhydryl-1-[2-methoxy-5-(trifluoromethyl)benzyl]piperazine dihydrochloride NMR (DMSO-d$_6$, δ): 3.02–4.72 (14H, m), 7.17–7.82 (13H, m)

MASS (APCI): 441 (M+H)$^+$ (free)

(4) 3-Benzhydryl-1-(5-bromo-2-methoxybenzyl)piperazine dihydrochloride

NMR (DMSO-d$_6$, δ): 3.00–4.70 (14H, m), 7.26–7.64 (13H, m)

MASS (APCI): 451 (M+H)$^+$ (free)

(5) 3-Benzhydryl-1-[2-methoxy-5-(1H-tetrazol-1-yl)benzyl]piperazine dihydrochloride NMR (DMSO-d$_6$, δ): 2.95–4.65 (15H, m), 7.18–7.95 (13H, m)

MASS (APCI): 441 (M+H)$^+$ (free)

(6) 2-Benzhydryl-4-[2-methoxy-5-(trifluoromethoxy)benzyl]morpholine hydrochloride NMR (DMSO-d$_6$, δ): 2.90–4.62 (13H, m), 7.04–7.57 (3H, m)

MASS (APCI): 458 (M+H)$^+$ (free)

(7) 2-Benzhydryl-4-[2-methoxy-5-[5-(trifluoromethyl)-1H-tetrazol-1-yl]benzyl]morpholine hydrochloride NMR (DMSO-d$_6$, δ): 2.80–4.55 (13H, m), 7.18–7.34 (11H, m), 8.13 (2H, m)

MASS (APCI): 510 (M+H)$^+$ (free)

(8) 6-Benzhydryl-4-[2-methoxy-5-[5-(trifluoromethyl)-1H-tetrazol-1-yl]benzyl]piperazin-2-one hydrochloride NMR (DMSO-d$_6$, δ): 2.84–4.55 (12H, m), 7.24–7.38 (11H, m), 7.75–7.79 (2H, m)

MASS (APCI): 523 (M+H)$^+$ (free)

(9) 5-Benzhydryl-7-[2-methoxy-5-[5-(trifluoromethyl)-1H-tetrazol-1-yl]benzyl]-5,6,7,8-tetrahydroimidazo[1,2-a]pyrazine dihydrochloride NMR (DMSO-d$_6$, δ): 2.86 (2H, m), 3.57–3.76 (3H, m), 3.83 (3H, s), 4.28 (1H, d, J=16.5 Hz), 4.48 (1H, d, J=11.0 Hz), 5.49 (1H, d, J=10.6 Hz), 6.26 (1H, s), 7.21–7.38 (12H, m), 7.67–7.77 (2H, m)

MASS (APCI): 546 (M+H)$^+$ (free)

(10) 6-Benzhydryl-4-[2-methoxy-5-[5-(trifluoromethyl)-1H-tetrazol-1-yl]benzyl]-3-methylpiperazin-2-one hydrochloride NMR (DMSO-$d_6$, δ): 1.42 (3H, m), 2.72–4.55 (11H, m), 7.11–7.34 (10H, m), 7.59–7.68 (3H, m)

MASS (APCI): 537 (M+H)$^+$ (free)

(11) 6-Benzhydryl-3,3-dimethyl-4-[2-methoxy-5-[5-(trifluoromethyl)-1H-tetrazol-1-yl]benzyl]piperazin-2-one hydrochloride NMR (DMSO-$d_6$, δ): 1.24 (3H, s), 1.35 (3H, s), 3.54–4.40 (4H, m), 3.89 (3H, s), 4.55 (2H, s), 6.37 (1H, br s), 7.05–7.32 (9H, m), 7.59–7.78 (4H, m)

MASS (APCI): 551 (M+H)$^+$ (free)

(12) (3S)-3-Benzhydryl-1-[2-methoxy-5-[5-(trifluoromethyl)-1H-tetrazol-1-yl]benzyl]piperazine dihydrochloride NMR (DMSO-$d_6$, δ): 2.60–4.81 (14H, m), 7.17–7.50 (11H, m), 7.22–7.75 (2H, m)

MASS (APCI): 509 (M+H)$^+$ (free)

(13) (2S)-2-Benzhydryl-4-[2-methoxy-5-[5-(trifluoromethyl)-1H-tetrazol-1-yl]benzyl]-1-methylpiperazine dihydrochloride NMR (DMSO-$d_6$, δ): 2.28–4.73 (16H, m), 7.15–7.40 (9H, m), 7.55 (2H, m), 7.71 (2H, m)

MASS (APCI): 523 (M+H)$^+$ (free)

(14) (8aS)-4-Benzhydryl-2-[2-methoxy-5-[5-(trifluoromethyl)-1H-tetrazol-1-yl]benzyl]octahydropyrrolo[1,2-a]pyrazine dihydrochloride NMR (DMSO-$d_6$, δ): 1.23–3.49 (11H, m), 3.64–3.96 (5H, m), 3.74 (3H, s), 4.23 (1H, d, J=9.5 Hz), 7.16–7.67 (13H, m)

MASS (APCI): 549 (M+H)$^+$ (free)

(15) (2R)-2-Benzhydryl-4-(2-methoxybenzyl)-1-methylpiperazine dihydrochloride

NMR (DMSO-$d_6$, δ): 2.66–4.78 (16H, m), 6.89–6.99 (2H, m), 7.26–7.55 (12H, m)

MASS (APCI): 387 (M+H)$^+$ (free)

(16) (2R)-2-Benzhydryl-4-[2-methoxy-5-[5-(trifluoromethyl)-1H-tetrazol-1-yl]benzyl]-1-methylpiperazine dihydrochloride NMR (DMSO-$d_6$, δ): 2.28–4.73 (16H, m), 7.15–7.40 (9H, m), 7.55 (2H, m), 7.71 (2H, m)

MASS (APCI): 523 (M+H)$^+$ (free)

(17) (3R)-3-Benzhydryl-1-[2-methoxy-5-[5-(trifluoromethyl)-1H-tetrazol-1-yl]benzyl]piperazine dihydrochloride NMR (DMSO-$d_6$, δ): 2.60–4.81 (14H, m), 7.17–7.50 (11H, m), 7.22–7.75 (2H, m)

MASS (APCI): 509 (M+H)$^+$ (free)

(18) (2S)-2-Benzhydryl-4-[2-(trifluoromethyl)benzyl]-1-methylpiperazine dihydrochloride NMR (DMSO-$d_6$, δ): 2.20–5.10 (13H, m), 7.08–8.14 (14H, m)

MASS (APCI): 425 (M+H)$^+$ (free)

(19) (2R)-2-Benzhydryl-4-[2-(trifluoromethyl)benzyl]-1-methylpiperazine dihydrochloride NMR (DMSO-$d_6$, δ): 2.20–5.10 (13H, m), 7.08–8.14 (14H, m)

MASS (APCI): 425 (M+H)$^+$ (free)

(20) (4R,8aS)-4-Benzhydryl-2-(2,6-dimethoxybenzyl)octahydropyrrolo[1,2-a]pyrazine dihydrochloride NMR (DMSO-$d_6$, δ): 1.58–4.51 (23H, m), 6.63 (1H, d, J=8.4 Hz), 7.26–7.51 (12H, m)

MASS (APCI): 443 (M+H)$^+$ (free)

(21) (4R,8aS)-4-Benzhydryl-2-[2-methoxy-5-(trifluoromethoxy)benzyl]octahydropyrrolo[1,2-a]pyrazine dihydrochloride NMR (DMSO-$d_6$, δ): 1.60–2.20 (3H, m), 2.79–4.20 (17H, m), 7.02–7.53 (13H, m)

MASS (APCI): 497 (M+H)$^+$ (free)

(22) (4R,8aS)-4-Benzhydryl-2-(2-ethoxybenzyl)octahydropyrrolo[1,2-a]pyrazine dihydrochloride NMR (DMSO-$d_6$, δ): 1.20–4.30 (22H, m), 6.92–7.50 (14H, m)

MASS (APCI): 427 (M+H)$^+$ (free)

(23) (4R,8aS)-4-Benzhydryl-2-(2,4-dimethoxybenzyl)octahydropyrrolo[1,2-a]pyrazine dihydrochloride NMR (DMSO-$d_6$, δ): 1.50–4.11 (17H, m), 3.78 (6H, s), 6.50 (3H, m), 7.31–7.49 (10H, m)

MASS (APCI): 443 (M+H)$^+$ (free)

(24) (4R,8aS)-4-Benzhydryl-2-[(2,2-difluorobenzo[1,3]dioxol-4-yl)methyl]octahydropyrrolo[1,2-a]pyrazine dihydrochloride NMR (DMSO-$d_6$, δ): 1.50–2.20 (4H, m), 2.75–4.56 (17H, m), 7.17–7.82 (13H, m)

MASS (APCI): 463 (M+H)$^+$ (free)

(25) (4R,8aS)-4-Benzhydryl-2-(2,4,6-trimethoxybenzyl)octahydropyrrolo[1,2-a]pyrazine dihydrochloride NMR (DMSO-$d_6$, δ): 1.50–2.20 (2H, m), 2.80–4.00 (15H, m), 3.80 (9H, s), 6.19 (2H, s), 7.31–7.46 (10H, m)

MASS (APCI): 473 (M+H)$^+$ (free)

(26) (4R,8aS)-4-Benzhydryl-2-(2,4,5-trimethoxybenzyl)octahydropyrrolo[1,2-a]pyrazine dihydrochloride NMR (DMSO-$d_6$, δ): 1.40–2.20 (3H, m), 2.55–4.20 (14H, m), 3.80 (9H, s), 6.61 (1H, s), 7.25–7.49 (11H, m)

MASS (APCI): 473 (M+H)$^+$ (free)

(27) (4R,8aS)-4-Benzhydryl-2-[2-methoxy-5-(trifluoromethyl)benzyl]octahydropyrrolo[1,2-a]pyrazine dihydrochloride NMR (DMSO-$d_6$, δ): 1.50–2.20 (3H, m), 2.88–5.09 (14H, m), 3.73 (3H, s), 7.13–7.79 (13H, m)

MASS (APCI): 481 (M+H)$^+$ (free)

(28) (4R,8aS)-4-Benzhydryl-2-(5-bromo-2,4-dimethoxybenzyl)octahydropyrrolo[1,2-a]pyrazine dihydrochloride NMR (DMSO-$d_6$, δ): 1.60–1.98 (3H, m), 2.94–4.40 (14H, m), 3.89 (6H, s), 6.67 (1H, s), 7.26–7.64 (11H, m)

MASS (APCI): 521 (M+H)$^+$ (free)

(29) (4R,8aS)-4-Benzhydryl-2-(5-bromo-2,4-methoxybenzyl)octahydropyrrolo[1,2-a]pyrazine dihydrochloride NMR (DMSO-$d_6$, δ): 1.64–2.06 (3H, m), 2.50–4.85 (14H, m), 3.62 (3H, s), 6.90–7.60 (13H, m)

MASS (APCI): 493 (M+H)$^+$ (free)

(30) (4R,8aS)-4-Benzhydryl-2-(5-isopropyl-2-methoxybenzyl)octahydropyrrolo[1,2-a]pyrazine dihydrochloride NMR (DMSO-$d_6$, δ): 1.17 (6H, d, J=5.4 Hz), 1.50–2.20 (3H, m), 2.80–4.15 (18H, m), 6.86–7.50 (13H, m)

MASS (APCI): 455 (M+H)$^+$ (free)

(31) (4R,8aS)-4-Benzhydryl-2-(2,4-dimethoxy-5-methylbenzyl)octahydropyrrolo[1,2-a]pyrazine dihydrochloride NMR (DMSO-$d_6$, δ): 1.55–2.10 (3H, m), 2.03 (3H, s), 3.00–4.55 (14H, m), 3.83 (6H, s), 6.53 (1H, s), 7.14–7.49 (11H, m)

MASS (APCI): 457 (M+H)$^+$ (free)

(32) 2-[((4R,8aS)-4-Benzhydrylhexahydropyrrolo[1,2-a]pyrazine-2-yl)methyl]benzonitrile dihydrochloride NMR (DMSO-$d_6$, δ): 1.80–2.20 (3H, m), 2.40–4.58 (14H, m), 7.15–7.79 (14H, m)

MASS (APCI): 408 (M+H)$^+$ (free)

(33) 2-[((4R,8aS)-4-Benzhydrylhexahydropyrrolo[1,2-a]pyrazine-2-yl)methyl]benzoic acid methyl ester dihydrochloride NMR (DMSO-$d_6$, δ): 1.50–2.20 (3H, m), 2.80–4.60 (14H, m), 3.82 (3H, s), 7.17–7.84 (14H, m)

MASS (APCI): 441 (M+H)+ (free)

(34) (4R,8aS)-4-Benzhydryl-2-(2-iodobenzyl)octahydropyrrolo[1,2-a]pyrazine dihydrochloride NMR (DMSO-$d_6$, δ): 1.55–2.20 (3H, m), 2.60–4.51 (14H, m), 7.01–7.82 (14H, m)

MASS (APCI): 509 (M+H)+ (free)

(35) (4R,8aS)-4-Benzhydryl-2-(2-nitrobenzyl)octahydropyrrolo[1,2-a]pyrazine dihydrochloride NMR (DMSO-$d_6$, δ): 1.55–2.20 (3H, m), 2.60–4.40 (14H, m), 7.23–7.88 (14H, m)

MASS (APCI): 428 (M+H)+ (free)

(36) (4R,8aS)-4-Benzhydryl-2-[2-(trifluoromethyl)benzyl]octahydropyrrolo[1,2-a]pyrazine dihydrochloride NMR (DMSO-$d_6$, δ): 1.60–2.20 (3H, m), 2.70–4.67 (14H, m), 7.12–7.77 (14H, m)

MASS (APCI): 451 (M+H)+ (free)

(37) (4R,8aS)-4-Benzhydryl-2-(2,5-dimethoxybenzyl)octahydropyrrolo[1,2-a]pyrazine dihydrochloride NMR (DMSO-$d_6$, δ): 1.50–2.20 (3H, m), 2.80–5.00 (14H, m), 3.72 (6H, s), 6.75–7.54 (13H, m)

MASS (APCI): 443 (M+H)+ (free)

(38) (4R,8aS)-4-Benzhydryl-2-(2,6-diethoxybenzyl)octahydropyrrolo[1,2-a]pyrazine dihydrochloride NMR (DMSO-$d_6$, δ): 1.21 (6H, t, J=6.7 Hz), 1.50–2.20 (3H, m), 2.76–4.46 (18H, m), 6.58 (1H, d, J=8.4 Hz), 7.30–7.46 (12H, m)

MASS (APCI): 471 (M+H)+ (free)

(39) (4R,8aS)-4-Benzhydryl-2-[2-ethoxy-5-[5-(trifluoromethyl)-1H-tetrazol-1-yl]benzyl]octahydropyrrolo[1,2-a]pyrazine dihydrochloride NMR (DMSO-$d_6$, δ): 1.14–1.40 (3H, m), 1.50–2.10 (3H, m), 2.73 (2H, br), 3.40–4.30 (14H, m), 7.17–7.69 (13H, m)

MASS (APCI): 563 (M+H)+ (free)

(40) (4R,8aS)-4-Benzhydryl-2-[2-propoxy-5-[5-(trifluoromethyl)-1H-tetrazol-1-yl]benzyl]octahydropyrrolo[1,2-a]pyrazine dihydrochloride NMR (DMSO-$d_6$, δ): 0.96 (3H, t, J=7.4 Hz), 1.60–2.07 (5H, m), 2.78 (2H, br s), 3.40–4.56 (14H, m), 7.17–7.70 (13H, m)

MASS (APCI): 577 (M+H)+ (free)

(41) (4R,8aS)-4-Benzhydryl-2-[2-isopropoxy-5-[5-(trifluoromethyl)-1H-tetrazol-1-yl]benzyl]octahydropyrrolo[1,2-a]pyrazine dihydrochloride NMR (DMSO-$d_6$, δ): 1.16–1.33 (6H, m), 3.20–3.80 (18H, m), 7.20–7.60 (13H, m)

MASS (APCI): 577 (M+H)+ (free)

(42) (4R,8aS)-4-Benzhydryl-2-[2-(2-methoxyethoxy)-5-[5-(trifluoromethyl)-1H-tetrazol-1-yl]benzyl]octahydropyrrolo[1,2-a]pyrazine dihydrochloride NMR (DMSO-$d_6$, δ): 1.40–2.10 (3H, m), 2.70 (1H, br), 3.31–4.56 (20H, m), 7.15–7.68 (13H, m)

MASS (APCI): 593 (M+H)+ (free)

(43) (4R,8aS)-4-Benzhydryl-2-[2-cyclopentyloxy-5-[5-(trifluoromethyl)-1H-tetrazol-1-yl]benzyl]octahydropyrrolo[1,2-a]pyrazine dihydrochloride NMR (DMSO-$d_6$, δ): 1.61–2.06 (11H, m), 2.70 (1H, br), 3.30–4.84 (14H, m), 7.20–7.66 (13H, m)

MASS (APCI): 603 (M+H)+ (free)

(44) (4R,8aS)-4-Benzhydryl-2-[2-fluoromethoxy-5-[5-(trifluoromethyl)-1H-tetrazol-1-yl]benzyl]octahydropyrrolo[1,2-a]pyrazine dihydrochloride NMR (DMSO-$d_6$, δ): 1.50–2.20 (3H, m), 2.60 (1H, br), 3.20–4.48 (13H, m), 5.74 (1H, br), 6.00 (1H, br), 7.14–7.74 (13H, m)

MASS (APCI): 567 (M+H)+ (free)

(45) (4R,8aS)-4-Benzhydryl-2-(2,4,5-trimethylbenzyl)octahydropyrrolo[1,2-a]pyrazine

MASS (APCI): 425 (M+H)+

(46) (4R,8aS)-4-Benzhydryl-2-[3,5-bis(trifluoromethyl)benzyl]octahydropyrrolo[1,2-a]pyrazine

MASS (APCI): 519 (M+H)+

(47) (4R,8aS)-4-Benzhydryl-2-[2,5-bis(trifluoromethyl)benzyl]octahydropyrrolo[1,2-a]pyrazine

MASS (APCI): 519 (M+H)+

(48) (4R,8aS)-4-Benzhydryl-2-[2-chloro-5-(trifluoromethyl)benzyl]octahydropyrrolo[1,2-a]pyrazine

MASS (APCI): 485 (M+H)+

(49) (4R,8aS)-4-Benzhydryl-2-(3,5-dimethylbenzyl)octahydropyrrolo[1,2-a]pyrazine

MASS (APCI): 411 (M+H)+

(50) (4R,8aS)-4-Benzhydryl-2-[2-fluoro-5-(trifluoromethyl)benzyl]octahydropyrrolo[1,2-a]pyrazine

MASS (APCI): 469 (M+H)+

(51) (4R,8aS)-4-Benzhydryl-2-[2-methoxy-5-(methanesulfonyl)benzyl]octahydropyrrolo[1,2-a]pyrazine dihydrochloride NMR (DMSO-$d_6$, δ): 3.19 (3H, s), 3.72 (3H, s), 1.20–5.10 (17H, m), 7.16–7.40 (9H, m), 7.50–7.55 (2H, m), 7.99 (1H, dd, J=2.5, 8.6 Hz), 8.05 (1H, br s)

MASS (APCI): 491 (M+H)+ (free)

(52) (4R,8aS)-4-Benzhydryl-2-[2-hydroxy-5-[5-(trifluoromethyl)-1H-tetrazol-1-yl]benzyl]octahydropyrrolo[1,2-a]pyrazine dihydrochloride NMR (DMSO-$d_6$, δ): 1.20–4.80 (16H, m), 7.04–7.57 (13H, m)

MASS (APCI): 535 (M+H)+ (free)

(53) (4R,8aS)-4-Benzhydryl-2-[2-methoxy-5-[5-(trifluoromethyl)-1H-tetrazol-1-yl]benzyl]octahydropyrrolo[1,2-a]pyrazine dihydrochloride NMR (DMSO-$d_6$, δ): 1.50–5.00 (15H, m), 3.76 (3H, s), 7.21–7.57 (13H, m)

MASS (APCI): 549 (M+H)+ (free)

(54) [2-((4R,8aS)-4-Benzhydrylhexahydropyrrolo[1,2-a]pyrazin-2-ylmethyl)-4-[5-(trifluoromethyl)-1H-tetrazol-1-yl]phenoxy]acetic acid methyl ester NMR (CDCl$_3$, δ) 1.10–2.10 (7H, m), 2.30–2.46 (2H, m), 2.60–2.70 (1H, m), 2.93 (1H, d, J=10.0 Hz), 3.27–3.43 (1H, m), 3.53 (1H, d, J=15.4 Hz), 3.59 (1H, d, J=15.4 Hz), 3.81 (3H, s), 4.00 (1H, d, J=9.1 Hz), 4.60 (2H, s), 6.79 (1H, d, J=8.8 Hz), 7.00–7.45 (11H, m), 7.51 (1H, d, J=2.6 Hz)

MASS (APCI): 607 (M+H)+

(55) (3RS,4aSR,8aSR)-3-Benzhydryl-1-[2-methoxy-5-(5-(trifluoromethyl)-1H-tetrazol-1-yl)benzyl]decahydroquinoxaline NMR (CDCl$_3$, δ): 1.03–2.14 (12H, m), 2.49 (1H, br s), 2.68 (1H, d, J=10.8 Hz), 3.32 (1H, d, J=16.5 Hz), 3.80 (3H, s), 3.64–3.96 (2H, m), 6.88 (1H, d, J=8.8 Hz), 7.01–7.39 (11H, m), 7.56 (1H, d, J=2.7 Hz)

MASS (APCI): 563 (M+H)+

Dihydrochloride of the above compound

MASS (APCI): 563 (M+H)+ (free)

(56) (3RS,4aSR,8aRS)-3-Benzhydryl-1-[2-methoxy-5-[5-(trifluoromethyl)-1H-tetrazol-1-yl]benzyl]-decahydroquinoxaline NMR (CDCl$_3$, δ): 1.13–2.20 (11H, m), 2.67–2.85 (2H, m), 2.90–3.33 (1H, m), 3.26 (1H, d, J=15.9 Hz), 3.82 (3H, s), 3.87 (2H, br s), 6.89 (1H, d, J=8.8 Hz), 7.00–7.34 (11H, m), 7.59 (1H, d, J=2.7 Hz)

MASS (APCI) 563 (M+H)$^+$

EXAMPLE 4

Sodium triacetoxyborohydride (146 mg) was added portionwise to a mixture of 37% aqueous formaldehyde (30 mg) and 3-benzhydryl-1-[2-methoxy-5-[5-(trifluoromethyl)-1H-tetrazol-1-yl]benzyl]piperazine dihydrochloride in a mixture of dichloromethane (4 ml) and methanol (2 drops) at 0° C. and the whole was stirred at 5° C.~room temperature overnight. The mixture was partitioned between ethyl acetate and 2N sodium hydroxide. The organic layer was separated, washed with brine, dried over sodium sulfate and evaporated under reduced pressure. The resulting residue was purified by column chromatography on silica gel using a mixed solvent of dichloromethane and methanol (60:1). The fractions containing the objective compound were collected and evaporated under reduced pressure and treated with 4N hydrogen chloride in ethyl acetate solution to give 2-benzhydryl-4-[2-methoxy-5-[5-(trifluoromethyl)-1H-tetrazol-1-yl]benzyl]-1-methylpiperazine dihydrochloride (32.9 mg) as a colorless powder.

NMR (DMSO-d$_6$, δ): 2.28–4.73 (16H, m), 7.15–7.40 (9H, m), 7.55 (2H, m), 7.71 (2H, m)

MASS (APCI): 523 (M+H)$^+$ (free)

EXAMPLE 5

The following compounds were obtained according to a similar manner to that of Example 4.

(1) (2S)-2-Benzhydryl-4-(2-methoxybenzyl)-1-methylpiperazine dihydrochloride

NMR (DMSO-d$_6$, δ): 2.66–4.78 (16H, m), 6.89–6.99 (2H, m), 7.26–7.55 (12H, m)

MASS (APCI): 387 (M+H)$^+$ (free)

(2) (2S)-2-Benzhydryl-4-benzyl-1-methylpiperazine dihydrochloride

NMR (DMSO-d$_6$, δ): 2.60–4.91 (14H, m), 7.23–7.56 (15H, m)

MASS (APCI): 357 (M+H)$^+$ (free)

(3) (6R,9aS)-4-Benzhydryl-2-[2-methoxy-5-[5-(trifluoromethyl)-1H-tetrazol-1-yl]benzyl]-8-methyloctahydropyrazino[1,2-a]pyrazine trihydrochloride NMR (DMSO-d$_6$, δ): 1.20–4.58 (21H, m), 7.23–7.32 (11H, m), 7.78 (2H, m)

MASS (APCI): 578 (M+H)$^+$ (free)

(4) (2RS,4aSR,8aSR)-2-Benzhydryl-4-[2-methoxy-5-[5-(trifluoromethyl)-1H-tetrazol-1-yl]benzyl]-1-methyldecahydroquinoxaline NMR (CDCl$_3$, δ): 1.04–2.52 (12H, m), 3.25 (1H, d, J=15.8 Hz), 3.60–4.01 (3H, m), 3.81 (3H, s), 6.85–7.51 (13H, m)

MASS (APCI): 577 (M+H)$^+$

Dihydrochloride of the above compound

MASS (APCI) 577 (M+H)$^+$ (free)

(5) (2RS,4aRS,8aSR)-2-Benzhydryl-4-[2-methoxy-5-[5-(trifluoromethyl)-1H-tetrazol-1-yl]benzyl]-1-methyldecahydroquinoxaline NMR (CDCl$_3$, δ): 1.17–2.50 (11H, m), 2.49 (3H, s), 2.70 (1H, br d, J=11.2 Hz), 2.83 (1H, br s), 3.09 (1H, d, J=15.3 Hz), 3.79 (3H, s), 3.83–3.96 (2H, m), 6.85 (1H, d, J=8.3 Hz), 6.91–7.34 (11H, m), 7.34 (1H, d, J=2.6 Hz)

MASS (APCI): 577 (M+H)$^+$

Dihydrochloride of the above compound

MASS (APCI): 577 (M+H)$^+$ (free)

EXAMPLE 6

The following compounds were obtained according to a similar manner to that of Preparation 13.

(1) 6-Benzhydryl-4-benzylpiperazin-2-one

NMR (DMSO-d$_6$, δ): 2.40 (2H, d, J=3.6 Hz), 2.83 (1H, d, J=16.4 Hz), 3.09 (1H, d, J=16.4 Hz), 3.29 (1H, d, J=13.0 Hz), 3.54 (1H, d, J=13.0 Hz), 4.20 (2H, m), 6.80 (1H, m), 7.08–7.45 (15H, m)

MASS (APCI): 357 (M+H)$^+$ (2) 6-Benzhydryl-4-[2-methoxy-5-(trifluoromethoxy)benzyl]-piperazin-2-one NMR (DMSO-d$_6$, δ): 2.39 (2H, m), 2.94 (1H, d, J=16.3 Hz), 3.12 (1H, d, J=16.3 Hz), 3.40 (1H, d, J=13.8 Hz), 3.49 (1H, d, J=13.8 Hz), 3.72 (3H, s), 4.08 (1H, d, J=10.7 Hz), 4.29 (1H, m), 6.74 (1H, m), 7.00–7.43 (13H, m)

MASS (APCI): 471 (M+H)$^+$

EXAMPLE 7

6-Benzhydryl-4-(2-methoxy-5-trifluoromethoxy)benzylpiperazin-2-one (47 mg) was treated with 4N hydrogen chloride in ethyl ester to give colorless powder of 6-benzhydryl-4-[2-methoxy-5-(trifluoromethoxy)benzyl]-piperazin-2-one hydrochloride (50.7 mg).

NMR (DMSO-d$_6$, δ): 2.87–4.66 (12H, m), 7.05–7.57 (13H, m)

MASS (APCI): 471 (M+H)$^+$ (free)

EXAMPLE 8

Sodium hydride (60% in mineral oil, 5 mg) was added by small portions to an ice-cooled solution of 6-benzhydryl-4-[2-methoxy-5-(trifluoromethoxy)benzyl]piperazin-2-one (30 mg) in N,N-dimethylformamide (2 ml) below 5° C. under nitrogen atmosphere. After the mixture was stirred for 5 minutes, methyl iodide (18.1 mg) was added to the mixture. The whole was stirred at room temperature for 2 hours and thereto water was added. The whole was extracted with ethyl acetate. The extract was dried over magnesium sulfate and evaporated under reduced pressure. The residue was purified by column chromatography on silica gel using a mixed solvent of dichloromethane and methanol (60:1). The fractions containing the objective compound were collected, evaporated under reduced pressure and treated with 4N hydrogen chloride in ethyl acetate solution to give 6-benzhydryl-4-[2-methoxy-5-(trifluoromethoxy)benzyl]-1-methylpiperazin-2-one hydrochloride (21 mg) as a colorless powder.

NMR (DMSO-d$_6$, δ) 2.19–4.80 (12H, m), 6.97–7.79 (13H, m)

MASS (APCI): 485 (M+H)$^+$ (free)

EXAMPLE 9

Aminoacetaldehyde diethyl acetal (72.4 ml) was added portionwise to a mixture of 6-benzhydryl-4-[2-methoxy-5-(trifluoromethoxy)benzyl]piperazin-2-one (78 mg) and titanium tetrachloride (1.0M in toluene, 0.033 ml) in mesitylene (5 ml) at 150° C. and the whole was stirred at 160° C. for 72 hours. The mixture was partitioned between ethyl acetate and 2N sodium hydroxide. The organic layer was separated, washed with brine, dried over sodium sulfate and evaporated under reduced pressure. The resulting residue was purified by column chromatography on silica gel using a mixed solvent of dichloromethane and methanol (90:1). The fractions containing the objective compound were collected, evaporated under reduced pressure and treated with 4N hydrogen chloride in ethyl acetate solution to give 5-benzhydryl-7-[2-methoxy-5-(trifluoromethoxy)benzyl]-5,6,7,8-tetrahydroimidazo[1,2-a]pyrazine dihydrochloride (74 mg) as a colorless powder.

NMR (DMSO-$d_6$, δ): 2.79 (2H, m), 3.25–3.83 (6H, m), 4.39 (2H, m), 5.42 (1H, m), 6.21 (1H, s), 6.99–7.36 (14H, m)

MASS (APCI): 494 (M+H)$^+$ (free)

EXAMPLE 10

The following compound was obtained according to a similar manner to that of Example 9.

5-Benzhydryl-7-benzyl-5,6,7,8-tetrahydroimidazo[1,2-a]pyrazine

MASS (APCI): 380 (M+H)$^+$

EXAMPLE 11

Lithium aluminum hydride (198 mg) was added by small portions to an ice-cooled solution of 1,4-dibenzyl-3-benzhydryl-2,5-piperazinedione (800 mg) in tetrahydrofuran (8 ml) under nitrogen atmosphere, and the mixture was stirred under reflux for 5 hours. After being cooled with ice, 2N sodium hydroxide (1 ml) was added to the mixture under nitrogen atmosphere. The resulting precipitates were filtered off and washed with tetrahydrofuran, and the filtrate and the washings were combined and evaporated under reduced pressure to give a crude oil. The oil was purified by column chromatography on silica gel using a mixed solvent of hexane and ethyl acetate (9:1). The fractions containing the objective compound were collected, evaporated under reduced pressure and treated with 4N hydrogen chloride in ethyl acetate solution to give 1,4-dibenzyl-2-benzhydrylpiperazine dihydrochloride (846 mg) as a colorless powder.

NMR (DMSO-$d_6$, δ): 2.30–6.50 (12H, m), 7.03–7.98 (20H, m)

MASS (APCI): 433 (M+H)$^+$ (free)

EXAMPLE 12

The following compounds were obtained according to a similar manner to that of Example 11.

(1) (3S)-3-Benzhydryl-1-(2-methoxybenzyl)piperazine dihydrochloride

NMR (DMSO-$d_6$, δ): 2.60–4.71 (14H, m), 6.92–7.03 (2H, m), 7.29–7.46 (12H, m)

MASS (APCI): 373 (M+H)$^+$ (free)

(2) (3S)-3-Benzhydryl-1-benzylpiperazine dihydrochloride

NMR (DMSO-$d_6$, δ): 3.00–4.75 (11H, m), 7.26–7.52 (15H, m)

MASS (APCI): 343 (M+H)$^+$ (free)

EXAMPLE 13

A solution of [2-[[(4R,8aS)-4-benzhydrylhexahydropyrrolo[1,2-a]pyrazin-2-yl]methyl]-4-[5-(trifluoromethyl)-1H-tetrazol-1-yl]phenoxy]acetic acid methyl ester in methanol containing 20% ammonia was stored at room temperature for 1 day. The mixture was evaporated under reduced pressure. The residue was purified by column chromatography on silica gel using a mixed solvent of dichloromethane and methanol (100:1). The fractions containing the objective compound were collected and evaporated under reduced pressure. The residue was treated with 4N hydrogen chloride in ethyl acetate to give colorless powders of 2-[2-[[(4R,8aS)-4-benzhydrylhexahydropyrrolo [1,2-a]pyrazin-2-yl]methyl]-4-[5-(trifluoromethyl)-1H-tetrazol-1-yl]phenoxy]acetamide dihydrochloride (70 mg).

IR (KBr): 3400, 1681, 1504 cm$^{-1}$

NMR (DMSO-$d_6$, δ): 1.40–5.10 (17H, m), 4.60 (2H, s), 7.16–7.80 (13H, m)

MASS (APCI): 592 (M+H)$^+$ (free)

EXAMPLE 14

(4R,8aS)-4-Benzhydryl-2-(2-methoxy-5-bromobenzyl) octahydropyrrolo[1,2-a]pyrazine dihydrochloride (29.8 mg) was dissolved in a mixture of 1,2-dimethoxyethane (0.5 ml) and 2M aqueous sodium carbonate (0.16 ml). Then phenylboronic acid (9.01 mg) and tetrakis(triphenylphosphine) palladium (6.1 mg) were added to the solution at room temperature. The whole was stirred for 2 hours at 85° C. The reaction mixture was poured into water, extracted with ethyl acetate. The extract was washed with brine, dried over magnesium sulfate and evaporated under reduced pressure. The resulting residue was purified by preparative TLC (0.5 mm) with a mixture of dichloromethane and methanol (15:1) as an eluent, and treated with 4N hydrogen chloride in ethyl acetate to give (4R,8aS)-4-benzhydryl-2-[(4-methoxy-[1,1'-biphenyl]-3-yl)methyl]octahydropyrrolo[1,2-a]pyrazine dihydrochloride (24.4 mg) as a brownish power.

NMR (DMSO-$d_6$, δ): 1.50–2.20 (3H, m), 2.70–4.50 (17H, m), 6.72–7.80 (18H, m)

MASS (APCI): 489 (M+H)$^+$ (free)

EXAMPLE 15

The following compound was obtained according to a similar manner to that of. Example 14.

(4R,8aS)-4-Benzhydryl-2-[2-methoxy-5-(3-thienyl) benzyl]octahydropyrrolo[1,2-a]pyrazine dihydrochloride NMR (DMSO-$d_6$, δ): 1.60–2.15 (3H, m), 2.70–4.60 (17H, m), 6.99–7.90 (16H, m)

MASS (APCI): 495 (M+H)$^+$ (free)

EXAMPLE 16

(4R,8aS)-4-Benzhydryl-2-(2-methoxy-5-bromobenzyl) octahydropyrrolo[1,2-a]pyrazine dihydrochloride (29.8 mg) was dissolved in N,N-dimethylformamide (2.0 ml). Then potassium carbonate (85.6 mg), N-methylimidazol (43.6 mg), palladium acetate (3.98 mg) and triphenylphosphine (9.29 mg) were added to the solution at room temperature. The whole was stirred for 10 hours at 140° C. The reaction mixture was poured into aqueous sodium hydrogen carbonate. The whole mixture was extracted with ethyl acetate. The extract was washed with brine, dried over magnesium sulfate and evaporated under reduced pressure. The resulting residue was purified by preparative TLC (0.5 mm) with a mixture of dichloromethane and methanol (10:1) as an eluent, and treated with 4N hydrogen chloride in ethyl acetate to give (4R,8aS)-4-benzhydryl-2-[2-methoxy-5-(3-methyl-3H-imidazol-4-yl)benzyl]octahydropyrrolo[1,2-a] pyrazine dihydrochloride (46.1 mg) as a colorless powder.

NMR (DMSO-$d_6$, δ): 1.50–2.10 (3H, m), 1.91 (3H, s), 2.60–4.50 (13H, m), 4.01 (3H, s), 7.11–7.80 (14H, m), 9.21 (1H, s)

MASS (APCI): 493 (M+H)$^+$ (free)

EXAMPLE 17

The following compound was obtained according to a similar manner to that of Preparation 18.

(4R,9aS)-4-Benzhydryl-2-[2-methoxy-5-[5-(trifluoromethyl)-1H-tetrazol-1-yl]benzyl]octahydro-2H-pyrido[1,2-a]pyrazine dihydrochloride NMR (DMSO-$d_6$, δ): 1.23–1.90 (3H, m), 2.65–4.74 (16H, m), 3.73 (3H, s), 7.19–7.73 (13H, m)

MASS (APCI): 563 (M+H)$^+$ (free)

EXAMPLE 18

(2R)-2-Benzyloxycarbonylamino-3-[N-(2-methoxybenzyl)-N-(2-oxo-3,3-diphenylpropyl)amino]propionic acid methyl ester (1.55 g) was dissolved in a mixture of tetrahydrofuran (50 ml) and triethylamine (0.744 ml), and the whole was hydrogenated over 10% palladium-charcoal (50% wet, 0.15 g) at room temperature under atmospheric pressure for 4 hours. After removal of the catalyst by filtration, the filtrate was evaporated under reduced pressure. The residue was purified by column chromatography on silica gel using a mixed solvent of hexane and ethyl acetate (2:1) as an eluent. The fractions containing the objective compound were collected and evaporated under reduced pressure to give (2R)-6-benzhydryl-4-(2-methoxybenzyl)piperazine-2-carboxylic acid methyl ester (663.8 mg) as a yellow oil.

NMR (CDCl$_3$, δ): 1.91 (1H, dd, J=10.9, 11.0 Hz), 2.13 (1H, d, J=10.9 Hz), 2.71 (1H, d, J=10.9 Hz), 3.15 (1H, d, J=10.9 Hz), 3.48–3.86 (6H, m), 3.62 (3H, s), 3.70 (3H, s), 6.78–7.50 (14H, m)

MASS (APCI): 431 (M+H)$^+$

EXAMPLE 19

The following compound was obtained according to a similar manner to that of Preparation 26.

[(2R)-6-Benzhydryl-4-(2-methoxybenzyl)piperazin-2-yl]methanol dihydrochloride

NMR (DMSO-$d_6$, δ): 2.80–4.80 (16H, m), 2.69–7.43 (14H, m)

MASS (APCI): 403 (M+H)$^+$ (free)

EXAMPLE 20

Potassium carbonate (81.3 mg) was added to a mixture of [(2R)-6-benzhydryl-4-(2-methoxybenzyl)piperazin-2-yl]methanol dihydrochloride (48.0 mg) in a mixed solvent of dichloromethane and water. Chloroacetyl chloride was added to the mixture below 5° C. and the whole was stirred for 1 hour. The organic layer was separated, washed with brine, dried over magnesium sulfate, and evaporated under reduced pressure. The resulting residue was dissolved into tert-butanol (4 ml) and potassium tert-butoxide (22.0 mg) was added to the mixture. The reaction mixture was poured into aqueous sodium hydrogen carbonate, and the whole was extracted with ethyl acetate. The extract was dried over magnesium sulfate, and evaporated under reduced pressure. The residue was purified by preparative TLC (15 PLC plate 20×20 cm, silica gel 60 F$_{254}$, 1 mm, Merck) with a mixture of hexane and ethyl acetate as an eluent to give (9aR)-6-benzhydryl-8-(2-methoxybenzyl)hexahydropyrazino[2,1-c][1,4]oxazin-4-one (30 mg) as a colorless oil.

NMR (DMSO-$d_6$, δ): 2.38 (1H, d, J=9.7 Hz), 2.48 (1H, d, J=10.9 Hz), 2.68 (1H, d, J=10.9 Hz), 2.83 (1H, d, J=9.7 Hz), 3.47–4.17 (8H, m), 3.73 (3H, s), .5.37 (1H, d, J=12.3 Hz), 6.78–7.32 (14H, m)

MASS (APCI): 443 (M+H)$^+$ (free)

EXAMPLE 21

Lithium aluminum hydride (3.9 mg) was added to an ice-cooled solution of (9aR)-6-benzhydryl-8-(2-methoxybenzyl)hexahydropyrazino[2,1-c][1,4]oxazin-4-one (22.9 mg) in tetrahydrofuran (1.1 ml) under nitrogen atmosphere. The mixture was stirred for 3 hours below 5° C. The reaction mixture was allowed to room temperature and stirred for 2 hours. After addition of another lithium aluminum hydride (4 mg), the reaction mixture was stirred for 14 hours. The reaction was quenched by a sequential addition of water (0.12 ml), 15% aqueous sodium hydroxide (0.12 ml) and water (0.36 ml), and the whole was stirred at room temperature for 1 hour. The insoluble materials were removed by filtration. The filtrate was dried over sodium sulfate and evaporated under reduced pressure. The resulting residue was purified by preparative TLC (0.5 mm) with a mixture of hexane and ethyl acetate (1:1) as an eluent. The resulting residue was treated with 4N hydrogen chloride in ethyl acetate to give (9aR)-6-benzhydryl-8-(2-methoxybenzyl)hexahydropyrazino-[1,2-c][1,4]oxazine dihydrochloride (9.6 mg) as a brownish powder.

NMR (DMSO-$d_6$, δ): 0.83–1.27 (1H, m), 2.60–4.30 (16H, m), 3.71 (3H, s), 6.92–7.44 (14H, m)

MASS (APCI): 493 (M+H)$^+$ (free)

EXAMPLE 22

(6R,9aR)-6-Benzhydryl-8-(tert-butoxycarbonyl)octahydropyrazino[2,1-c][1,4]oxazine was treated with 4N hydrogen chloride in 1,4-dioxane to give (6R,9aR)-octahydro-6-benzhydrylpyrazino[2,1-c][1,4]oxazine dihydrochloride as a yellowish powder. (6R,9aR)-6-Benzhydryl-8-[2-methoxy-5-[5-(trifluoromethyl)-1H-tetrazol-1-yl]benzyl]octahydropyrazino[2,1-c][1,4]oxazine dihydrochloride was obtained from (6R,9aR)-6-benzhydrylhexahydropyrazino[2,1-c][1,4]oxazine dihydrochloride according to a similar manner to that of Example 2.

NMR (DMSO-$d_6$, δ): 2.07–2.60 (3H, m), 2.75–4.54 (17H, m), 7.18–7.78 (13H, m)

MASS (APCI): 565 (M+H)$^+$ (free)

EXAMPLE 23

4N Hydrogen chloride in ethyl acetate solution (3 ml) was added to a solution of (2R)-2-[[N-(2-methoxybenzyl)-N-(2-oxo-3,3-diphenylpropyl)amino]methyl]piperazine-1,4-dicarboxylic acid 4-benzyl ester 1-tert-butyl ester (160 mg) in ethyl acetate (3 ml) at room temperature. After being stirred for 2 hours, the reaction mixture was concentrated under reduced pressure. The resulting residue was dissolved into dichloromethane (4 ml). Sodium triacetoxyborohydride (150 mg) was added to the stirred mixture and the whole was stirred at room temperature for 18 hours. The mixture was partitioned between ethyl acetate and 2N sodium hydroxide. The organic layer was separated, washed with brine, dried over magnesium sulfate and evaporated under reduced pressure. The resulting residue was purified by column chromatography on silica gel using a mixed solvent of hexane and ethyl acetate (3:4) as an eluent to give (6R,9aR)-6-benzhydryl-8-(2-methoxybenzyl)octahydropyrazino[1,2-a]pyrazine-2-carboxylic acid benzyl ester (108 mg) as a colorless powder.

NMR (CDCl$_3$, δ): 1.83–2.09 (3H, m), 2.43 (2H, m), 2.60–3.05 (4H, m), 3.20–3.56 (3H, m), 3.68 (3H, s), 3.78 (2H, m), 4.18 (1H, d, J=6.9 Hz), 5.08 (2H, s), 6.70–7.32 (19H, m)

MASS (APCI): 562 (M+H)$^+$

EXAMPLE 24

A solution of (6R,9aR)-6-benzhydryl-8-(2-methoxybenzyl)octahydropyrazino[1,2-a]pyrazine-2-carboxylic acid benzyl ester (100 mg) and triethylamine (0.049 ml) in tetrahydrofuran (3 ml) was hydrogenated over 10% palladium-carbon (50% wet, 20 mg) at room temperature under atmospheric pressure for 2 hours. After removal of the catalyst by filtration, the filtrate was evaporated under reduced pressure to give an oil, which was purified by column chromatography on silica gel using a mixed solvent of dichloromethane and methanol (4:1). The fractions containing the objective compound were collected and evaporated under reduced pressure and the resulting residue was treated with 4N hydrogen chloride in ethyl acetate to give (6R,9aS)-4-benzhydryl-2-(2-methoxybenzyl)octahydropyrazino[1,2-a]pyrazine trihydrochloride (58 mg) as a colorless powder.

NMR (DMSO-d$_6$, δ): 2.26–4.45 (19H, m), 6.91–7.46 (14H, m)

MASS (APCI): 428 (M+H)$^+$ (free)

EXAMPLE 25

Acetyl chloride (3 drops) was added to a mixture of (6R,9aS)-4-benzhydryl-2-(2-methoxybenzyl)octahydropyrazino[1,2-a]pyrazine trihydrochloride (20 mg) and N,N-diisopropylethylamine (6 drops) in dichloromethane (1 ml) under ice-cooling. After being stirred at the same temperature for 2 hours, the mixture was poured into ice-water and extracted with ethyl acetate. The extract was washed with brine, dried over sodium sulfate and evaporated under reduced pressure to give a crude oil. The oil was purified by column chromatography on silica gel using a mixed solvent of dichloromethane and methanol (50:1) as an eluent. The fractions containing the objective compound were collected and evaporated under reduced pressure and the resulting residue was treated with 4N hydrogen chloride in ethyl acetate to give 1-[(6R,9aR)-6-benzhydryl-8-(2-methoxybenzyl)octahydropyrazino[1,2-a]pyrazin-2-yl]ethanone dihydrochloride (9.8 mg) as a colorless powder.

NMR (DMSO-d$_6$, δ): 1.90–4.60 (21H, m), 6.95–7.39 (14H, m)

MASS (APCI): 470 (M+H)$^+$ (free)

EXAMPLE 26

1-Chloroethyl chloroformate (0.055 ml) was added to a stirred solution of (6R,9aR)-6-benzhydryl-8-(2-methoxybenzyl)octahydropyrazino[1,2-a]pyrazine-2-carboxylic acid benzyl ester (140 mg) in 1,2-dichloroethane (3 ml) under nitrogen atmosphere. After being stirred for 2.5 hours at 50° C., the whole mixture was concentrated under reduced pressure. The resulting residue was dissolved into methanol (5 ml) and the reaction mixture was stirred for 1.5 hours under reflux. The mixture was concentrated under reduced pressure to give an oily residue. Sodium triacetoxyborohydride (424 mg) and N,N-diisopropylethylamine (0.087 ml) were added to a mixture of the residue obtained in the above procedure and 2-methoxy-5-[5-(trifluoromethyl)-1H-tetrazol-1-yl]benzaldehyde (75 mg) in dichloromethane (6 ml), and the whole was stirred at room temperature for 18 hours. The resulting mixture was partitioned between ethyl acetate and 2N sodium hydroxide. The organic layer was separated, washed with brine, dried over magnesium sulfate and evaporated under reduced pressure. The resulting residue was purified by column chromatography on silica gel using a mixed solvent of dichloromethane and methanol (50:1) as an eluent to give (6R,9aR)-6-benzhydryl-8-[2-methoxy-5-[5-(trifluoromethyl)-1H-tetrazol-1-yl]benzyl]octahydropyrazino[1,2-a]pyrazine-2-carboxylic acid benzyl ester (155 mg) as a colorless powder.

NMR (CDCl$_3$, δ): 1.83–2.11 (3H, m), 2.44 (2H, m), 2.62–3.05 (4H, m), 3.21–3.90 (8H, m), 4.18 (1H, d, J=7.0 Hz), 5.08 (2H, s), 6.90–7.78 (18H, m)

MASS (APCI): 698 (M+H)$^+$

EXAMPLE 27

The following compound was obtained according to a similar manner to that of Example 24.

(6R,9aS)-4-Benzhydryl-2-[2-methoxy-5-[5-(trifluoromethyl)-1H-tetrazol-1-yl]benzyl]octahydropyrazino[1,2-a]pyrazine trihydrochloride NMR (DMSO-d$_6$, δ): 2.10–4.47 (19H, m), 7.24–7.34 (11H, m), 7.79–7.85 (2H, m)

MASS (APCI): 564 (M+H)$^+$ (free)

EXAMPLE 28

Methyl chloroformate (3 drops) was added to a mixture of (6R,9aS)-4-benzhydryl-2-[2-methoxy-5-[5-(trifluoromethyl)-1H-tetrazol-1-yl]benzyl]octahydropyrazino[1,2-a]pyrazine trihydrochloride (12 mg) and N,N-diisopropylethylamine (6 dorps) in dichloromethane (1 ml) under ice-cooling. After being stirred at the same temperature for 2 hours, the mixture was poured into ice-water and extracted with ethyl acetate. The extract was washed with brine, dried over sodium sulfate, and evaporated under reduced pressure. The resulting oil was purified by column chromatography on silica gel using a mixed solvent of dichloromethane and methanol (50:1) as an eluent. The fractions containing the objective compound were collected and evaporated under reduced pressure and the resulting residue was treated with 4N hydrogen chloride in ethyl acetate to give (6R,9aR)-6-benzhydryl-8-[2-methoxy-5-[5-(trifluoromethyl)-1H-tetrazol-1-yl]benzyl]octahydropyrazino[1,2-a]pyrazine-2-carboxylic acid methyl ester dihydrochloride (7.0 mg) as a colorless powder.

NMR (DMSO-d$_6$, δ): 2.10–4.45 (21H, m), 7.18–7.78 (13H, m)

MASS (APCI): 622 (M+H)$^+$ (free)

EXAMPLE 29

The following compound was obtained according to a similar manner to that of Example 25.

1-[(6R,9aR)-6-Benzhydryl-8-[2-methoxy-5-[5-(trifluoromethyl)-1H-tetrazol-1-yl]benzyl]octahydropyrazino[1,2-a]pyrazin-2-yl]ethanone dihydrochloride NMR (DMSO-d$_6$, δ): 1.90–4.40 (21H, m), 7.21–7.37 (11H, m), 7.78 (2H, m)

MASS (APCI): 606 (M+H)$^+$ (free)

EXAMPLE 30

A 1M solution of sodium triacetoxyborohydride in N,N-dimethylformamide (75 μl) was added portionwise to a mixture of 2-methoxybenzaldehyde (7.5 mg) and a solution of 2-benzhydryl-1-methylpiperazine dihydrochloride (17.0 mg) in N,N-dimethylformamide (50 µl) at 0° C. and the whole was stirred at 0° C. to 5° C. for 1 hour and further at 5° C. to room temperature for 1 hour. The mixture was extracted with aqueous 0.25N sulfuric acid solution and washed with ethyl acetate. The combined solution was applied on solid phase extraction column cartridge (C18, 200 mg) and eluted with water and acetonitrile successively. The eluate was concentrated in vacuo to give 2-benzhydryl-4-(2-methoxybenzyl)-1-methylpiperazine (14.3 mg).

MASS (APCI): 387 (M+H)+

EXAMPLE 31

The following compounds were obtained according to a similar manner to that of Example 30.

(1) 2-Benzhydryl-4-(2,6-dimethoxybenzyl)-1-methylpiperazine
MASS (APCI): 417 (M+H)+

(2) 2-Benzhydryl-4-(2,4-dimethoxybenzyl)-1-methylpiperazine
MASS (APCI): 417 (M+H)+

(3) 2-Benzhydryl-4-[[2,2-difluorobenzo[1,3]dioxol-4-yl]methyl]-1-methylpiperazine
MASS (APCI): 437 (M+H)+

(4) 2-Benzhydryl-4-(2,4,6-trimethoxybenzyl)-1-methylpiperazine
MASS (APCI): 447 (M+H)+

(5) 2-Benzhydryl-4-(2,4,5-trimethoxybenzyl)-1-methylpiperazine
MASS (APCI): 447 (M+H)+

(6) 2-Benzhydryl-4-[2-methoxy-5-(1H-tetrazol-1-yl)benzyl]-1-methylpiperazine
MASS (APCI): 455 (M+H)+

(7) 2-Benzhydryl-4-[2-methoxy-5-(trifluoromethyl)benzyl]-1-methylpiperazine
MASS (APCI): 455 (M+H)+

(8) 2-Benzhydryl-4-[2-methoxy-5-(trifluoromethoxy)benzyl]-1-methylpiperazine
MASS (APCI): 471 (M+H)+

(9) 2-Benzhydryl-4-(5-bromo-2,4-dimethoxybenzyl)-1-methylpiperazine
MASS (APCI): 497 (M+H)+

(10) 2-Benzhydryl-4-(5-bromo-2-methoxybenzyl)-1-methylpiperazine ditrifluoroacetate
MASS (APCI): 467 (M+H)+

(11) 2-Benzhydryl-4-[5-(1-methylethyl)-2-methoxybenzyl]-1-methylpiperazine
MASS (APCI): 429 (M+H)+

(12) 2-Benzhydryl-4-(2,4-dimethoxy-5-methylbenzyl)-1-methylpiperazine
MASS (APCI): 431 (M+H)+

(13) 2-Benzhydryl-4-(2-ethoxybenzyl)-1-methylpiperazine
MASS (APCI): 401 (M+H)+

(14) 2-Benzhydryl-4-[2-(benzyloxy)benzyl]-1-methylpiperazine
MASS (APCI): 463 (M+H)+

(15) 2-Benzhydryl-4-[2-(allyloxy)benzyl]-1-methylpiperazine
MASS (APCI): 413 (M+H)+

(16) 2-Benzhydryl-4-(2-cyanobenzyl)-1-methylpiperazine
MASS (APCI): 382 (M+H)+

(17) 2-Benzhydryl-4-(2-methoxycarbonylbenzyl)-1-methylpiperazine
MASS (APCI): 415 (M+H)+

(18) 2-Benzhydryl-4-(2-iodobenzyl)-1-methylpiperazine
MASS (APCI): 483 (M+H)+

(19) 2-Benzhydryl-4-(2-nitrobenzyl)-1-methylpiperazine
MASS (APCI): 402 (M+H)+

(20) 2-Benzhydryl-4-(2-bromobenzyl)-1-methylpiperazine
MASS (APCI): 437 (M+H)+

(21) 2-Benzhydryl-4-[2-(trifluoromethyl)benzyl]-1-methylpiperazine
MASS (APCI): 425 (M+H)+

(22) 2-Benzhydryl-4-(2,5-dimethylbenzyl)-1-methylpiperazine
MASS (APCI): 416 (M+H)+

(23) 2-Benzhydryl-4-(4-dimethylamino-2-methoxybenzyl)-1-methylpiperazine
MASS (APCI): 429 (M+H)+

(24) 2-Benzhydryl-4-[(2-methoxynaphthalen-1-yl)methyl]-1-methylpiperazine
MASS (APCI): 436 (M+H)+

(25) 2-Benzhydryl-4-[(4-methoxypyridin-3-yl)methyl]-1-methylpiperazine
MASS (APCI): 387 (M+H)+

(26) 2-Benzhydryl-4-[2-(difluoromethoxy)benzyl]-1-methylpiperazine
MASS (APCI): 422 (M+H)+

(27) 2-Benzhydryl-4-[2-(trifluoromethoxy)benzyl]-1-methylpiperazine
MASS (APCI): 441 (M+H)+

(28) 2-Benzhydryl-4-[2-(chlorobenzyl]-1-methylpiperazine
MASS (APCI): 390 (M+H)+

EXAMPLE 32

A 1M solution of sodium triacetoxyborohydride in N,N-dimethylformamide (75 µl) was added portionwise to a mixture of 2-chloro-6-methoxybenzaldehyde (9.4 mg) and a solution of (4R,8aS)-4-benzhydryloctahydropyrrolo[1,2-a]pyrazine dihydrochloride (18.3 mg) in N,N-dimethylformamide (50 µl) at 25° C. and the whole was stirred at room temperature for 2 hours. The mixture was purified by high pressure liquid chromatography eluting with aqueous 0.1% trifluoroacetic acid solution-acetonitrile (90:10→10:90). The solution was concentrated in vacuo. To the residue was added ethyl acetate and aqueous 5% potassium carbonate solution. The mixture was applied on liquid/liquid extraction cartridge (CE1000M, VARIAN) and eluted with ethyl acetate. The eluate was concentrated in vacuo to give (4R,8aS)-4-benzhydryl-2-(2-chloro-6-methoxybenzyl)octahydropyrrolo[1,2-a]pyrazine (11.0 mg)

MASS (APCI): 447 (M+H)+

EXAMPLE 33

The following compounds were obtained according to a similar manner to that of Example 32.

(1) (4R,8aS)-4-Benzhydryl-2-[2-methoxy-6-(trifluoromethyl)benzyl]octahydropyrrolo[1,2-a]pyrazine
MASS (APCI): 481 (M+H)+

(2) (4R,8aS)-4-Benzhydryl-2-[2,4-dimethoxy-6-(methoxycarbonyl)benzyl]octahydropyrrolo[1,2-a]pyrazine
MASS (APCI): 501 (M+H)+

(3) (4R,8aS)-4-Benzhydryl-2-(2,4,6-trimethylbenzyl)octahydropyrrolo[1,2-a]pyrazine
MASS (APCI): 425 (M+H)+

(4) (4R,8aS)-4-Benzhydryl-2-(2,3,6-trifluorobenzyl)octahydropyrrolo[1,2-a]pyrazine
MASS (APCI): 414 (M+H)+

(5) (4R,8aS)-4-Benzhydryl-2-[(3-methoxypyridin-2-yl)methyl]octahydropyrrolo[1,2-a]pyrazine
MASS (APCI): 414 (M+H)+

(6) (4R,8aS)-4-Benzhydryl-2-(2,5-dimethoxybenzyl)octahydropyrrolo[1,2-a]pyrazine
MASS (APCI): 443 (M+H)+

(7) (4R,8aS)-4-Benzhydryl-2-(4-dimethylamino-2-methoxybenzyl)octahydropyrrolo[1,2-a]pyrazine

MASS (APCI): 180 (M+H)+

(8) (4R,8aS)-4-Benzhydryl-2-(2-methoxynaphthalen-1-ylmethyl)octahydropyrrolo[1,2-a]pyrazine

MASS (APCI): 463 (M+H)+

(9) (4R,8aS)-4-Benzhydryl-2-[2-(difluoromethoxy)benzyl]octahydropyrrolo[1,2-a]pyrazine

MASS (APCI): 449 (M+H)+

(10) (4R,8aS)-4-Benzhydryl-2-[2-(trifluoromethoxy)benzyl]octahydropyrrolo[1,2-a]pyrazine

MASS (APCI): 467 (M+H)+

(11) (4R,8aS)-4-Benzhydryl-2-(3,5-dimethoxybenzyl)octahydropyrrolo[1,2-a]pyrazine

MASS (APCI): 443 (M+H)+

(12) (4R,8aS)-4-Benzhydryl-2-[2,3-(methylenedioxy)benzyl]octahydropyrrolo[1,2-a]pyrazine

MASS (APCI): 427 (M+H)+

(13) (4R,8aS)-4-Benzhydryl-2-[(4-(methoxypyridin-3-yl)methyl]octahydropyrrolo[1,2-a]pyrazine

MASS (APCI): 414 (M+H)+

(14) (4R,8aS)-4-Benzhydryl-2-(2-methoxybenzyl)octahydropyrrolo[1,2-a]pyrazine

MASS (APCI): 413 (M+H)+

(15) (4R,8aS)-4-Benzhydryl-2-[2-(methylthio)benzyl]octahydropyrrolo[1,2-a]pyrazine

MASS (APCI): 429 (M+H)+

(16) (4R,8aS)-4-Benzhydryl-2-(2-ethoxy-6-methoxybenzyl)octahydropyrrolo[1,2-a]pyrazine

MASS (APCI): 457 (M+H)+

(17) (4R,8aS)-4-Benzhydryl-2-(2-isopropoxy-6-methoxybenzyl)octahydropyrrolo[1,2-a]pyrazine

MASS (APCI): 471 (M+H)+

(18) (4R,8aS)-4-Benzhydryl-2-(2-methoxy-6-propoxybenzyl)octahydropyrrolo[1,2-a]pyrazine

MASS (APCI): 471 (M+H)+

(19) (4R,8aS)-4-Benzhydryl-2-[2-methoxy-6-(2-methoxyethoxy)benzyl]octahydropyrrolo[1,2-a]pyrazine

MASS (APCI): 487 (M+H)+

(20) (4R,8aS)-4-Benzhydryl-2-[2-methoxy-6-(2,2,2-trifluoroethoxy)benzyl]octahydropyrrolo[1,2-a]pyrazine

MASS (APCI): 511 (M+H)+

(21) (4R,8aS)-4-Benzhydryl-2-(2-chloro-5-nitrobenzyl)octahydropyrrolo[1,2-a]pyrazine

MASS (APCI): 462 (M+H)+

(22) (4R,8aS)-4-Benzhydryl-2-(2,4-dichlorobenzyl)octahydropyrrolo[1,2-a]pyrazine

MASS (APCI): 541 (M+H)+

(23) (4R,8aS)-4-Benzhydryl-2-(2-fluoro-6-methoxybenzyl)octahydropyrrolo[1,2-a]pyrazine

MASS (APCI): 431 (M+H)+

(24) (4R,8aS)-4-Benzhydryl-2-[2-(cyanomethoxy)-6-methoxybenzyl]octahydropyrrolo[1,2-a]pyrazine

MASS (APCI): 468 (M+H)+

EXAMPLE 34

The following compounds were obtained according to a similar manner to that of Example 4.

(1) 2-Benzhydryl-1-ethyl-4-[2-methoxy-5-[5-(trifluoromethyl)-1H-tetrazol-1-yl]benzyl]piperazine dihydrochloride IR (KBr, FT-IR): 1454, 1320, 1270, 1230 cm$^{-1}$ NMR (DMSO-$d_6$, δ): 2.57–5.29 (15H, m), 3.81 (3H, s), 7.00–7.86 (13H, m)

MASS (APCI): 537 (M+H)+ (free)

(2) 2-Benzhydryl-4-[2-methoxy-5-[5-(trifluoromethyl)-1H-tetrazol-1-yl]benzyl]-1-propylpiperazine dihydrochloride IR (KBr, FT-IR): 1505, 1455, 1320, 1270, 1200 cm$^{-1}$ NMR (DMSO-$d_6$, δ): 0.47–5.20 (17H, m), 3.80 (3H, s), 7.10–7.88 (13H, m)

MASS (APCI): 551 (M+H)+ (free)

EXAMPLE 35

To a suspension of 2-[2-benzhydryl-4-[2-methoxy-5-[5-(trifluoromethyl)-1H-tetrazol-1-yl]benzyl]-1-piperazinyl]acetic acid (70 mg) and triethylamine (20 mg) in dichloromethane (5 ml) was added 2-chloro-1-methylpyridinium iodide (70 mg) at room temperature. After being stirred for 30 minutes, 28% aqueous ammonia (1 drop) was added to the solution. After being stirred for 1.5 hours, the mixture was washed with water. The organic layer was separated, dried over magnesium sulfate, and evaporated under reduced pressure. The syrup was purified by column chromatography on silica gel using a mixed solvent of dichloromethane and methanol (20:1). The fractions containing the objective compound were collected and evaporated under reduced pressure to give a syrup. The syrup was treated with 4N hydrogen chloride in ethyl acetate (1 ml) to give 2-[2-benzhydryl-4-[2-methoxy-5-[5-(trifluoromethyl)-1H-tetrazol-1-yl]benzyl]-1-piperazinyl]acetamide dihydrochloride (81 mg).

IR (KBr, FT-IR): 1665, 1610, 1440, 1320, 1265, 1235 cm$^{-1}$

NMR (DMSO-$d_6$, δ): 2.70–5.95 (14H, m), 3.66 (3H, s), 7.10–8.10 (13H, m)

MASS (APCI): 566 (M+H)+ (free)

EXAMPLE 36

The following compounds were obtained according to a similar manner to that of Example 2 from 2-benzhydryl-1-methylpiperazine dihydrochloride.

(1) 2-Benzhydryl-4-(2-ethoxy-6-methoxybenzyl)-1-methylpiperazine dihydrochloride NMR (CDCl$_3$, δ): 1.50–2.10 (4H, m), 2.48 (3H, s), 3.14–4.60 (12H, m), 4.69–4.74 (1H, m), 5.65–5.69 (1H, m), 6.45–6.49 (2H, d), 7.21–7.52 (13H, m)

MASS (APCI): 431 (M+1) (free)

(2) 2-Benzhydryl-4-[2-ethoxy-5-[5-(trifluoromethyl)-1H-tetrazol-1-yl]benzyl]-1-methylpiperazine dihydrochloride NMR (CDCl$_3$, δ): 1.12–5.35 (20H, m), 6.74–7.74 (13H, m)

MASS (APCI): 537 (M+1) free (3) 2-Benzhydryl-4-(2-isopropoxy-6-methoxybenzyl)-1-methylpiperazine dihydrochloride NMR (DMSO-$d_6$, δ): 1.10–1.30 (6H, m), 2.30–5.00 (17H, m), 6.55–6.71 (2H, m), 7.22–7.51 (11H, m)

MASS (APCI): 445 (M+H)+ (free)

EXAMPLE 37

The following compounds were obtained according to a similar manner to that of Example 2 from (6R,9aR)-6-benzhydryloctahydropyrazino[2,1-c][1,4]oxazine dihydrochloride.

(1) (6R,9aR)-6-Benzhydryl-8-(2-ethoxy-6-methoxybenzyl)octahydropyrazino[2,1-c][1,4]oxazine dihydrochloride NMR (CDCl$_3$, δ): 2.50 (1H, br), 3.07–3.34 (3H, m), 3.65–4.27 (14H, m), 4.67–4.83 (2H, m), 5.73 (1H, m), 6.47 (2H, d, J=8.5 Hz), 7.17–7.78 (13H, m), 12.86 (1H, m), 14.18 (1H, m)

MASS (APCI): 473 (M+1) (free)

(2) (6R,9aR)-6-Benzhydryl-8-[2-ethoxy-5-[5-(trifluoromethyl)-1H-tetrazol-1-yl]benzyl]octahydropyrazino[2,1-c][1,4]oxazine dihydrochloride NMR (DMSO-$d_6$, δ): 1.27–4.55 (22H, m), 7.17–7.79 (13H, m)

MASS (APCI): 579 (M+1) (free)

(3) (6R,9aR)-6-Benzhydryl-8-(2-isopropoxy-6-methoxybenzyl)octahydropyrazino[2,1-c][1,4]oxazine dihydrochloride NMR (DMSO-$d_6$, δ): 1.10–1.30 (6H, m), 3.64 (3H, s) 2.30–4.8 (16H, m), 6.55–6.71 (2H, m), 7.22–7.51 (11H, m), 10.50–11.50 (2H, m)

MASS (APCI): 487 (M+H)$^+$ (free)

EXAMPLE 38

A mixture of (4R,8aS)-4-benzhydryl-2-(5-bromo-2-methoxybenzyl)octahydropyrrolo[1,2-a]pyrazine dihydrochloride (100 mg), diethyl-3-pyridylboran (39.1 mg), tetrakis(triphenylphosphine)palladium (20.5 mg), powdered potassium hydroxide (29.8 mg) and tetrabutylammonium bromide (17.1 mg) in tetrahydrofuran (2 ml) were stirred for 8 hours at 70° C. After being cooled to room temperature, the reaction mixture was poured into aqueous saturated sodium hydrogen carbonate, and extracted with ethyl acetate. The extract was washed with brine, dried over magnesium sulfate and evaporated under reduced pressure. The resulting residue was purified by preparative TLC (0.5 mm) with a mixture of dichloromethane and methanol (10:1) as an eluent. The resulting residue was treated with 4N hydrogen chloride in ethyl acetate to give (4R,8aS)-4-benzhydryl-2-[2-methoxy-5-(3-pyridyl)benzyl]octahydropyrrolo[1,2-a]pyrazine trihydrochloride (25.9 mg).

NMR (DMSO-$d_6$, δ): 3.23–4.00 (20H, m), 7.12–9.14 (17H, m)

MASS (APCI): 490 (M+1) (free)

EXAMPLE 39

The following compounds were obtained according to a similar manner to that of Example 2 from (4R,8aS)-4-benzhydryloctahydropyrrolo[1,2-a]pyrazine dihydrochloride.

(1) (4R,8aS)-4-Benzhydryl-2-[2-methoxy-5-(2-thienyl)benzyl]octahydropyrrolo[1,2-a]pyrazine dihydrochloride NMR (DMSO-$d_6$, δ): 1.5–2.2 (5H, m), 2.55–4.99 (25H, m), 6.99–7.82 (16H, m)

MASS (APCI): 495 (M+1) (free)

(2) (4R,8aS)-4-Benzhydryl-2-[5-(3-furyl)-2-methoxybenzyl]octahydropyrrolo[1,2-a]pyrazine dihydrochloride NMR (DMSO-$d_6$, δ): 1.40–4.49 (20H, m), 6.92–8.08 (16H, m)

MASS (APCI): 479 (M+1) (free)

(3) (4R,8aS)-4-Benzhydryl-2-[2-methoxy-5-(4-pyridyl)benzyl]octahydropyrrolo[1,2-a]pyrazine trihydrochloride NMR (DMSO-$d_6$, δ) 1.64–5.14 (21H, m), 6.96–8.97 (17H, m)

MASS (APCI): 490 (M+1) (free)

(4) (4R,8aS)-4-Benzhydryl-2-[2-methoxy-5-[5-(methylthio)-1H-tetrazol-1-yl]benzyl]octahydropyrrolo[1,2-a]pyrazine dihydrochloride NMR (DMSO-$d_6$, δ) 1.30–4.55 (23H, m), 7.15–7.65 (13H, m)

MASS (APCI): 527 (M+1) (free)

(5) (4R,8aS)-4-Benzhydryl-2-[2-methoxy-5-[5-(methylsulfonyl)-1H-tetrazol-1-yl]benzyl]octahydropyrrolo[1,2-a]pyrazine dihydrochloride NMR (DMSO-$d_6$, δ): 1.70–4.55 (23H, m), 7.17–7.76 (13H, m)

MASS (APCI): 559 (M+1) (free)

(6) (4R,8aS)-4-Benzhydryl-2-(2-isopropoxy-6-methoxybenzyl)octahydropyrrolo[1,2-a]pyrazine dihydrochloride NMR (DMSO-$d_6$, δ): 1.10–1.30(6H, m)), 3.57(3H, s), 2.30–4.8(16H, m), 6.55–6.68(2H, m), 7.22–7.51(11H, m)

MASS (APCI): 471 (M+H)$^+$ (free)

(7) (4R,8aS)-4-Benzhydryl-2-[2-isopropoxy-5-(trifluoromethoxy)benzyl]octahydropyrrolo[1,2-a]pyrazine dihydrochloride NMR (DMSO-$d_6$, δ): 1.10–1.30 (6H, m), 2.30–4.8 (16H, m), 7.18–7.71 (13H, m)

MASS (APCI): 525 (M+H)$^+$ (free)

(8) (4R,8aS)-4-Benzhydryl-2-[2-ethoxy-5-(trifluoromethoxy)benzyl]octahydropyrrolo[1,2-a]pyrazine dihydrochloride NMR (DMSO-$d_6$, δ): 1.10–1.30 (3H, m), 2.30–4.8 (17H, m), 7.18–7.71 (13H, m)

MASS (APCI): 511 (M+H)$^+$ (free)

(9) (4R,8aS)-4-Benzhydryl-2-(2-ethoxy-4,6-dimethoxybenzyl)octahydropyrrolo[1,2-a]pyrazine dihydrochloride NMR (DMSO-$d_6$, δ): 1.10–1.30 (3H, m), 3.60 (3H, s), 3.79 (3H, s), 2.30–4.8 (17H, m), 6.15–6.24 (2H, m), 7.25–7.51 (10H, m)

MASS (APCI): 487 (M+H)$^+$ (free)

(10) (4R,8aS)-4-Benzhydryl-2-(2-isopropoxy-4,6-dimethoxybenzyl)octahydropyrrolo[1,2-a]pyrazine dihydrochloride NMR (DMSO-$d_6$, δ): 1.10–1.30 (6H, m), 3.55 (3H, s), 3.79 (3H, s), 2.30–4.8 (16H, m), 6.18–6.20 (2H, m), 7.25–7.51 (10H, m)

MASS (APCI): 501 (M+H)$^+$ (free)

(11) (4R,8aS)-4-Benzhydryl-2-[5-(1H-imidazol-1-yl)-2-methoxybenzyl]octahydropyrrolo[1,2-a]pyrazine trihydrochloride NMR (DMSO-$d_6$, δ): 1.50–5.20 (18H, m), 7.10–8.00 (13H, m), 7.97 (1H, s), 8.24 (1H, s), 9.71 (1H, s)

MASS (APCI): 479 (M+H)$^+$ (free)

(12) (4R,8aS)-4-[Bis(4-fluorophenyl)methyl]-2-[2-methoxy-5-[5-(trifluoromethyl)-1H-tetrazol-1-yl]benzyl]octahydropyrrolo[1,2-a]pyrazine dihydrochloride IR (KBr, FT-IR): 1605, 1505, 1320, 1265, 1230 cm$^{-1}$ NMR (DMSO-$d_6$, δ): 1.40–4.80 (15H, m), 3.80 (3H, s), 7.06–7.95 (11H, m)

MASS (APCI): 585 (M+H)$^+$ (free)

(13) (1R or 1S,4R,8aS)-4-Benzhydryl-2-[2-methoxy-5-[5-(trifluoromethyl)-1H-tetrazol-1-yl]benzyl]-1-methyloctahydropyrrolo[1,2-a]pyrazine dihydrochloride NMR (HCl free) (CDCl$_3$, δ): 0.97–1.01 (3H, d, J=6.5 Hz), 1.36–1.70 (7H, m), 2.12 (1H, dd, J=3.4, 12.0 Hz), 2.31 (1H, dd, J=10.4, 12.0 Hz), 2.49 (1H, m), 2.73 (1H, m), 2.93 (1H, ddd, J=3.1, 6.5 Hz), 3.12 (1H, ddd, J=3.4, 7.5, 10.3 Hz), 3.48 (1H, d, J=16.0 Hz)

MASS (APCI): 563 (M+H)$^+$ (free)

(14) (1S or 1R,4R,8aS)-4-Benzhydryl-2-[2-methoxy-5-[5-(trifluoromethyl)-1H-tetrazol-1-yl]benzyl]-1-methyloctahydropyrrolo[1,2-a]pyrazine dihydrochloride NMR (DMSO-$d_6$, δ): 0.85–4.55 (22H, m), 7.08–7.63 (13H, m)

MASS (APCI): 563 (M+H)$^+$ (free)

(15) (4R,7R,8aS)-4-Benzhydryl-7-methoxy-2-[2-methoxy-5-[5-(trifluoromethyl)-1H-tetrazol-1-yl]benzyl]octahydropyrrolo[1,2-a]pyrazine dihydrochloride NMR (DMSO-$d_6$, δ): 1.90–5.00 (14H, m), 3.05 (3H, s), 3.76 (3H, s), 6.90–7.80 (13H, m)

MASS (APCI): 579 (M+H)$^+$ (free)

(16) N-[(4R,7S,8aS)-4-Benzhydryl-2-[2-methoxy-5-[5-(trifluoromethyl)-1H-tetrazol-1-yl]benzyl]octahydropyrrolo[1,2-a]pyrazin-7-yl]-N,N-dimethylamine trihydrochloride IR (KBr): 3400, 2900–2500, 1617, 1504, 1454 cm$^{-1}$ NMR (DMSO-$d_6$, δ): 1.90–5.00 (20H, m), 3.80 (3H, s), 7.19–7.37 (11H, m), 7.80–7.90 (2H, m), 10.00–11.80 (3H, m)

MASS (APCI): 592 (M+H)$^+$ (free)

(17) (4R,7S,8aS)-4-Benzhydryl-2-[2-methoxy-5-[5-(trifluoromethyl)-1H-tetrazol-1-yl]benzyl]octahydropyrrolo[1,2-a]pyrazin-7-amine trihydrochloride IR (KBr): 3400, 2900–2500, 1617, 1504, 1454 cm$^{-1}$ NMR (DMSO-$d_6$, δ): 2.00–4.50 (15H, m), 3.76 (3H, s), 7.21–7.81 (13H, m), 8.16 (3H, br s)

MASS (APCI): 564 (M+H)$^+$ (free)

(18) (4R,7S,8aS)-4-Benzhydryl-7-fluoro-2-[2-methoxy-5-[5-(trifluoromethyl)-1H-tetrazol-1-yl]benzyl]octahydropyrrolo[1,2-a]pyrazine dihydrochloride NMR (DMSO-$d_6$, δ): 1.90–5.00 (14H, m), 3.82 (3H, s), 6.90–7.80 (13H, m)

MASS (APCI): 567 (M+H)$^+$ (free)

(19) (4S,7R,8aS)-4-Benzhydryl-7-methoxy-2-[2-methoxy-5-[5-(trifluoromethyl)-1H-tetrazol-1-yl]benzyl]octahydropyrrolo[1,2-a]pyrazine dihydrochloride IR (KBr): 3400, 2900–2500, 1617, 1504, 1454 cm$^{-1}$ NMR (DMSO-$d_6$, δ): 1.90–5.00 (14H, m), 3.03 (3H, s), 3.82 (3H, s), 6.90–7.80 (13H, m)

MASS (APCI): 579 (M+H)$^+$ (free)

(20) (4R,8S,8aR)-4-Benzhydryl-2-[2-methoxy-5-[5-(trifluoromethyl)-1H-tetrazol-1-yl]benzyl]octahydropyrrolo[1,2-a]pyrazin-8-ol dihydrochloride NMR (DMSO-$d_6$, δ): 2.84–4.55 (20H, m), 7.22–7.68 (13H, m)

MASS (APCI) 565 (M+1) (free)

(21) (4R,8S,8aR)-4-Benzhydryl-2-[2-methoxy-5-[5-(trifluoromethyl)-1H-tetrazol-1-yl]benzyl]octahydropyrrolo[1,2-a]pyrazin-8-ol NMR (CDCl$_3$, δ): 1.25–1.59 (2H, m), 1.84–2.17 (4H, m), 2.38–2.67 (3H, m), 2.95–3.00 (1H, m), 3.42–3.63 (3H, m), 3.80 (3H, s), 3.90–3.97 (2H, m), 6.90–7.45 (13H, m)

MASS (APCI): 565 (M+1)

EXAMPLE 40

(4R,7R,8aS)-4-Benzhydryl-7-[(tert-butyldimethylsilyl)oxy]-2-[2-methoxy-5-[5-(trifluoromethyl)-1H-tetrazol-1-yl]benzyl]octahydropyrrolo[1,2-a]pyrazine (0.17 g) was dissolved in 1M tetrabutylammonium fluoride in tetrahydrofuran solution (1 ml) and the whole was stirred at room temperature for 4 hours. The mixture was poured into water and extracted with ethyl acetate. The extract was dried over magnesium sulfate and concentrated under reduced pressure. The syrup was purified by column chromatography on silica gel using a mixed solvent of dichloromethane and methanol (100:1). The fractions containing the objective compound were collected and treated with 4N hydrogen chloride in ethyl acetate to give the following compounds.

(1) (4R,7R,8aS)-4-Benzhydryl-2-[2-methoxy-5-[5-(trifluoromethyl)-1H-tetrazol-1-yl]benzyl]octahydropyrrolo[1,2-a]pyrazin-7-ol dihydrochloride IR (KBr): 3400, 2700–2500, 1508 cm$^{-1}$ NMR (DMSO-$d_6$, δ): 2.00–5.00 (14H, m), 3.75 (3H, s), 7.16–7.80 (13H, m)

MASS (APCI): 565 (M+H)$^{30}$ (free)

(2) (4S,7R,8aS)-4-Benzhydryl-2-[2-methoxy-5-[5-(trifluoromethyl)-1H-tetrazol-1-yl]benzyl]octahydropyrrolo[1,2-a]pyrazin-7-ol dihydrochloride IR (KBr): 3400, 1504 cm$^{-1}$ NMR (DMSO-$d_6$, δ) 1.95–2.00 (2H, m), 2.90–5.00 (12H, m), 3.84 (3H, s), 7.00–8.00 (13H, m)

MASS (APCI): 565 (M+H)$^+$ (free)

EXAMPLE 41

The following compounds were obtained according to a similar manner to that of Example 22.

(1) (4R,7S,8aS)-4-Benzhydryl-2-[2-methoxy-5-[5-(trifluoromethyl)-1H-tetrazol-1-yl]benzyl]octahydropyrrolo[1,2-a]pyrazin-7-ol dihydrochloride NMR (DMSO-$d_6$, δ): 1.37 (1H, m), 2.69–2.80 (2H, m), 3.20–4.30 (17H, m), 7.16–7.72 (13H, m)

MASS (APCI): 565 (M+H)$^+$ (free)

(2) (4R,7S,8aS)-4-Benzhydryl-7-methoxy-2-[2-methoxy-5-[5-(trifluoromethyl)-1H-tetrazol-1-yl]benzyl]octahydropyrrolo[1,2-a]pyrazine dihydrochloride NMR (DMSO-$d_6$, δ) 2.25–4.60 (22H, m), 7.17–7.77 (13H, m)

MASS (APCI): 579 (M+H)$^+$ (free)

(3) (4R,7R,8aS)-4-Benzhydryl-7-fluoro-2-[2-methoxy-5-[5-(trifluoromethyl)-1H-tetrazol-1-yl]benzyl]octahydropyrrolo[1,2-a]pyrazine dihydrochloride NMR (DMSO-$d_6$, δ): 2.16–4.30 (19H, m), 7.20–8.04 (13H, m)

MASS (APCI): 567 (M+H)$^+$ (free)

EXAMPLE 42

To a solution of (2S)-2-[[N-(2-methoxybenzyl)-N-(2-oxo-3,3-diphenylpropyl)amino]methyl]piperazine-1,4-dicarboxylic acid 4-N-benzyl ester 1-N-tert-butyl ester (3.15 g) in ethyl acetate (15 ml) was added a solution of 4N hydrogen chloride in ethyl acetate (29.6 ml) under ice-cooling. After stirring at the same temperature for 3 hours, the reaction mixture was evaporated under reduced pressure. To the solution of the residue in dichloromethane (30 ml) was added portionwise sodium triacetoxyborohydride (2.95 g) under ice-cooling, and then it was stirred at the same temperature for 20 hours. The mixture was poured into aqueous sodium hydrogen carbonate and extracted with dichloromethane. The organic layer was washed with brine, dried over sodium sulfate, evaporated under reduced pressure. The resulting residue was purified by column chromatography on silica gel (5.2 g) using a mixed solvent of hexane and ethyl acetate (2:1). The fractions containing the objective compound were collected and evaporated under reduced pressure to give (4S,9aS)-8-(benzyloxycarbonyl)-4-benzhydryl-2-(2-methoxybenzyl)octahydro-2H-pyrazino[1,2-a]pyrazine (2.0 g) as a syrup.

NMR (CDCl$_3$, δ): 3.68 (3H, s), 1.75–4.25 (15H, m), 5.08 (2H, s), 6.70–6.90 (2H, m), 7.10–7.40 (17H, m)

MASS (APCI): 562 (M+H)$^+$

EXAMPLE 43

The following compound was obtained according to a similar manner for Example 42 from tert-butyl (2R,3S)-3- hydroxy-2-[[N-(2-methoxybenzyl)-N-(2-oxo-3,3-diphenylpropyl)amino]methyl]-1-pyrrolidinecarboxylate.

(4R,8S,8aR)-4-Benzhydryl-2-(2-methoxybenzyl)octahydropyrolo[1,2-a]pyrazin-8-ol

NMR (DMSO-d$_6$, δ): 1.91–4.29 (19H, m), 7.18–7.80 (13H, m)

MASS (APCI): 429 (M+1)

EXAMPLE 44

The following compound was obtained according to a similar manner to that of Preparation 57 from (4R,8R,8aR)-8-azido-4-benzhydryl-2-[2-methoxy-5-[5-(trifluoromethyl)-1H-tetrazol-1-yl]benzyl]octahydropyrrolo[1,2-a]pyrazine.

(4R,8R,8aR)-4-Benzhydryl-2-[2-methoxy-5-[5-(trifluoromethyl)-1H-tetrazol-1-yl]benzyl]octahydropyrrolo-[1,2-a]pyrazin-8-amine NMR (CDCl$_3$, δ): 1.22–2.21 (12H, m), 3.24–3.62 (4H, m), 3.81 (3H, s), 6.74–7.78 (13H, m)

MASS (APCI): 564 (M+1)

EXAMPLE 45

The following compound was obtained according to a similar manner to that of Preparation 65 from (4R,8R,8aR)-4-benzhydryl-2-[2-methoxy-5-[5-(trifluoromethyl)-1H-tetrazol-1-yl]benzyl]octahydropyrrolo[1,2-a]pyrazin-8-yl acetate.

(4R,8R,8aR)-4-Benzhydryl-2-[2-methoxy-5-[5-(trifluoromethyl)-1H-tetrazol-1-yl]benzyl]octahydropyrrolo[1,2-a]pyrazin-8-ol NMR (CDCl$_3$, δ): 1.29–2.05 (6H, m), 2.18–2.23 (2H, m), 2.48–2.54 (1H, br), 2.74 (1H, m), 2.92 (1H, m), 3.26 (1H, m), 3.42–3.61 (2H, d×2, J=15.2 Hz), 3.81 (3H, s), 4.06–4.18 (1H, m), 6.91–7.48 (13H, m)

MASS (APCI): 565 (M+1)

Dihydrochloride of the above compound

NMR (DMSO-d$_6$, δ): 1.23–4.30 (20H, m), 7.21–7.56 (13H, m)

MASS (APCI): 565 (M+1) (free)

EXAMPLE 46

The following compound was obtained according to a similar manner to that of Preparation 57 from (4R,8S,8aR)-8-azido-4-benzhydryl-2-[2-methoxy-5-[5-(trifluoromethyl)-1H-tetrazol-1-yl]benzyl]octahydropyrrolo[1,2-a]pyrazine.

(4R,8S,8aR)-4-Benzhydryl-2-[2-methoxy-5-[5-(trifluoromethyl)-1H-tetrazol-1-yl]benzyl]octahydropyrrolo[1,2-a]pyrazin-8-amine NMR (CDCl$_3$, δ): 1.50–3.04 (12H, m), 3.34–3.65 (3H, m), 3.79 (3H, s), 4.03 (1H, m), 6.74–7.45 (13H, m)

MASS (APCI): 564 (M+1)

EXAMPLE 47

The following compounds were obtained according to a similar manner to that of Example 25.

(1) (4R,9aR)-4-Benzhydryl-2-[2-methoxy-5-[5-(trifluoromethyl)-1H-tetrazol-1-yl]benzyl]-8-propionyloctahydro-2H-pyrazino[1,2-a]pyrazine dihydrochloride mp: 171–175° C.

$[\alpha]_D^{29.9}$: −40.38° (C=0.26, MeOH)

IR (KBr): 3435, 1649, 1504, 1458, 1433, 1267, 1201, 1163, 1032 cm$^{-1}$

NMR (DMSO-d$_6$, δ): 0.95 (3H, t, J=7.5 Hz), 2.10–4.50 (17H, m) 3.83 (3H, s), 7.10–7.50 (11H, m), 7.70–7.90 (2H, m)

MASS (API-ES): 620 (M+H)$^+$ (free)

(2) (4R,9aR)-4-Benzhydryl-2-[2-methoxy-5-[5-(trifluoromethyl)-1H-tetrazol-1-yl]benzyl]-8-(2-methylpropionyl)octahydro-2H-pyrazino[1,2-a]pyrazine dihydrochloride mp: 172–175° C.

$[\alpha]_D^{29.9}$: −42.27° (C=0.33, MeOH)

IR (KBr): 3435, 1649, 1506, 1448, 1265, 1199, 1163 cm$^{-1}$

NMR (DMSO-d$_6$, δ): 0.93 (6H, d, J=6.6 Hz), 2.10–4.50 (16H, m), 3.82 (3H, s), 7.10–7.50 (11H, m), 7.70–7.90 (2H, m)

MASS (APCI): 634 (M+H)$^+$ (free)

(3) (4R,9aR)-4-Benzhydryl-8-butyryl-2-[2-methoxy-5-[5-(trifluoromethyl)-1H-tetrazol-1-yl]benzyl]octahydro-2H-pyrazino[1,2-a]pyrazine dihydrochloride mp: 162–166° C.

$[\alpha]_D^{30.0}$: −40.14° (C=0.36, MeOH)

IR (KBr): 3435, 1649, 1504, 1458, 1267, 1201, 1163, 1028 cm$^{-1}$

MASS (API-ES): 634 (M+H)$^+$ (free)

NMR (DMSO-d$_6$, δ): 0.85 (3H, t, J=7.5 Hz), 1.40–1.60 (2H, m), 2.10–4.50 (17H, m), 3.79 (3H, s), 7.10–7.50 (11H, m), 7.70–7.90 (2H, m)

(4) (4R,9aR)-4-Benzhydryl-8-ethoxycarbonyl-2-[2-methoxy-5-[5-(trifluoromethyl)-1H-tetrazol-1-yl]benzyl]octahydro-2H-pyrazino[1,2-a]pyrazine dihydrochloride mp: 153–156° C.

$[\alpha]_D^{29.9}$: −43.09° (C=0.34, MeOH)

IR (KBr): 3444, 2983, 1701, 1504, 1442, 1267, 1199, 1163 cm$^{-1}$

NMR (DMSO-d$_6$, δ): 1.14 (3H, t, J=7.0 Hz), 2.10–4.50 (15H, m), 3.82 (3H, s), 4.01 (2H, q, J=7.0 Hz), 7.10–7.50 (11H, m), 7.70–7.90 (2H, m)

MASS (API-ES): 636 (M+H)$^+$ (free)

(5) (4R,9aR)-4-Benzhydryl-8-isopropoxycarbonyl-2-[2-methoxy-5-[5-(trifluoromethyl)-1H-tetrazol-1-yl]benzyl]octahydro-2H-pyrazino[1,2-a]pyrazine dihydrochloride mp: 147–150° C.

$[\alpha]_D^{29.9}$: −43.23° (C=0.325, MeOH)

IR (KBr): 3442, 2985, 1701, 1506, 1462, 1429, 1269, 1199, 1161 cm$^{-1}$

NMR (DMSO-d$_6$, δ): 1.16 (6H, d, J=6.8 Hz), 2.20–4.80 (15H, m), 3.81 (3H, s), 4.73 (1H, m), 7.10–7.50 (11H, m), 7.70–7.90 (2H, m)

MASS (APCI): 650 (M+H)$^+$ (free)

EXAMPLE 48

The following compound was obtained according to a similar manner to that of Preparation 94.

(4R,9aR)-4-Benzhydryl-2-[2-methoxy-5-[5-(trifluoromethyl)-1H-tetrazol-1-yl]benzyl]-8-(3-methylbutyryl)octahydro-2H-pyrazino[1,2-a]pyrazine dihydrochloride mp: 138–150° C., decomp.

$[\alpha]_D^{27}$: −43.70 (C, 0.09, MeOH)

IR (KBr): 1649 cm$^{-1}$

NMR (DMSO-d$_6$, δ): 0.66 (6H, d, J=1.7 Hz), 1.71–4.30 (18H, m), 3.59 (3H, s), 7.07–7.58 (13H, m)

MASS (APCI+): 648.2 (MH+) (free)

EXAMPLE 49

Formic acid (28 μl) was added to a mixture of (4R,9aS)-4-benzhydryl-2-[2-methoxy-5-[5-(trifluoromethyl)-1H- tetrazol-1-yl]benzyl]octahydro-2H-pyrazino[1,2-a]pyrazine trihydrochloride (100 mg), N,N-diisopropylethylamine (129 μl), 1-hydroxybenzotriazole (30.1 mg) and 1-[3-(dimethylamino)propyl]-3-ethylcarbodiimide hydrochloride (34.2 mg) in dichloromethane (2.0 ml). After being stirred for 18 hours at room temperature, the resulting mixture was poured into water, and the whole was extracted with ethyl acetate, dried over sodium sulphate and evaporated under reduced pressure. The residue was purified by silica gel column chromatography using a mixed solvent of dichloromethane and methanol (20:1). The fractions containing the objective compound was collected and evaporated under reduced pressure and resulting residue was treated with 4N hydrogen chloride in ethyl acetate to give (6R,9aR)-6-benzhydryl-8-[2-methoxy-5-[5-(trifluoromethyl)-1H-tetrazol-1-yl]benzyl]octahydro-2H-pyrazino[1,2-a]pyrazine-2-carbaldehyde dihydrochloride (100.1 mg) as colourless powder.

NMR (DMSO-$d_6$, δ): 2.30–4.30 (21H, m), 7.18–8.00 (13H, m)

MASS (APCI): 592 (M+H)$^+$ (free)

EXAMPLE 50

The following compound was obtained according to a similar manner to that of Example 4.

(4R,9aR)-4-Benzhydryl-8-isopropyl-2-[2-methoxy-5-[5-(trifluoromethyl)-1H-tetrazol-1-yl]benzyl]octahydro-2H-pyrazino[1,2-a]pyrazine trihydrochloride NMR (DMSO-$d_6$, δ): 1.22–1.26 (6H, m), 2.20–4.56 (22H, m), 7.22–7.86 (13H, m)

MASS (APCI): 606 (M+H)$^+$ (free)

EXAMPLE 51

Methanesulfonyl chloride (22.1 mg) was added to a mixture of (4R,9aS)-4-benzhydryl-2-[2-methoxy-5-[5-(trifluoromethyl)-1H-tetrazol-1-yl]benzyl]octahydro-2H-pyrazino[1,2-a]pyrazine trihydrochloride (100 mg) and N,N-diisopropylethylamine (116 μl) in dichloromethane under ice-cooling. After being stirred at the same temperature for 2 hours the mixture was poured into ice-water and extracted with ethyl acetate. The extract was washed with brine, dried over magnesium sulphate, and evaporated under reduced pressure. The resulting oil was purified by column chromatography on silica gel using a mixed solvent of dichloromethane and methanol. The fractions containing the objective compound was collected and evaporated under reduced pressure and the resulting residue was treated with 4N hydrogen chloride in ethyl acetate to give (4R,9aR)-4-benzhydryl-2-[2-methoxy-5-[5-(trifluoromethyl)-1H-tetrazol-1-yl]benzyl]-8-(methylsulfonyl)octahydro-2H-pyrazino[1,2-a]pyrazine dihydrochloride (52.8 mg) as colourless powder.

NMR (DMSO-$d_6$, δ): 2.49–4.31 (23H, m), 7.17–7.80 (13H, m)

MASS: (APCI): 642 (M+H)$^+$ (free)

EXAMPLE 52

The following compounds were obtained according to a similar manner to that of Example 51.
(1) (4R,9aR)-4-Benzhydryl-8-ethylsulfonyl-2-[2-methoxy-5-[5-(trifluoromethyl)-1H-tetrazol-1-yl]benzyl]octahydro-2H-pyrazino[1,2-a]pyrazine dihydrochloride
mp: 143–146° C.
$[α]_D^{30.0}$: −43.33° (C=0.36, MeOH)
IR (KBr): 3435, 1506, 1458, 1329, 1267, 1199, 1159 cm$^{-1}$
NMR (DMSO-$d_6$, δ): 1.15 (3H, t, J=7.3 Hz), 2.20–4.50 (17H, m), 3.84 (3H, s), 7.10–7.50 (11H, m), 7.70–7.90 (2H, m)
MASS (API-ES): 656 (M+H)$^+$ (free)
(2) (4R,9aR)-4-Benzhydryl-2-[2-methoxy-5-[5-(trifluoromethyl)-1H-tetrazol-1-yl]benzyl]-8-propylsulfonyloctahydro-2H-pyrazino[1,2-a]pyrazine dihydrochloride
mp: 146–165° C.
$[α]_D^{28}$: −40.40 (C=0.125, MeOH)
IR (KBr): 1508 cm$^{-1}$
NMR (DMSO-$d_6$, δ): 0.93 (3H, t, J=7.25 Hz), 1.50–1.75 (2H, m), 2.30–4.40 (17H, m), 3.83 (3H, s), 7.16–7.82 (13H, m)
MASS (APCI+): 670.0 (MH+) (free)
(3) (4R,9aR)-4-Benzhydryl-8-isopropylsulfonyl-2-[2-methoxy-5-[5-(trifluoromethyl)-1H-tetrazol-1-yl]benzyl]octahydro-2H-pyrazino[1,2-a]pyrazine dihydrochloride
mp: 150–155° C.
$[α]_D^{30.3}$: −43.09° (C=0.55, MeOH)
IR (KBr): 3435, 1504, 1458, 1323, 1267, 1201, 1163 cm$^{-1}$
NMR (DMSO-$d_6$, δ): 1.16 (6H, d, J=6.8 Hz), 2.20–4.50 (16H, m), 3.84 (3H, s), 7.10–7.50 (11H, m), 7.70–7.90 (2H, m)
MASS (APCI): 670 (M+H)$^+$ (free)
(4) (4R,9aR)-4-Benzhydryl-2-[2-methoxy-5-[5-(trifluoromethyl)-1H-tetrazol-1-yl]benzyl]-8-(2,2,2-trifluoroethylsulfonyl)octahydro-2H-pyrazino[1,2-a]pyrazine dihydrochloride
IR (KBr): 1510 cm$^{-1}$
NMR (DMSO-$d_6$, δ): 2.20–4.56 (17H, m), 3.84 (3H, s), 7.17–7.83 (13H, m)
MASS (APCI+): 710.1 (MH+) (free)

EXAMPLE 53

The following compound was obtained according to a similar manner to that of Example 24.

(4R,9aS)-4-Benzhydryl-2-(2-methoxybenzyl)octahydro-2H-pyrazino[1,2-a]pyrazine

NMR (CDCl$_3$, δ): 3.67 (3H, s), 1.50–4.30 (16H, m), 6.70–6.90 (2H, m), 7.10–7.35 (12H, m)

MASS (APCI): 428 (M+H)$^+$

EXAMPLE 54

The following compound was obtained according to a similar manner to that of Example 25.

(4R,9aR)-8-Acetyl-4-benzhydryl-2-(2-methoxybenzyl)octahydro-2H-pyrazino[1,2-a]pyrazine NMR (CDCl$_3$, δ): 3.60–3.70 (3H, m), 1.70–4.00 (16H, m), 4.05–4.30 (2H, m), 6.70–6.95 (2H, m), 7.09–7.35 (12H, m)

MASS (APCI): 470 (M+H)$^+$

EXAMPLE 55

The following compounds were obtained according to a similar manner to that of Example 2.
(1) (4R,9aR)-8-Acetyl-4-benzhydryl-2-[2-methoxy-5-(trifluoromethyl)benzyl]octahydro-2H-pyrazino[1,2-a]pyrazine dihydrochloride
mp: 143–145° C.
$[α]_D^{30.0}$: −54.35° (C=0.85, MeOH)
IR (KBr): 3435, 1647, 1502, 1431, 1255, 1159 cm$^{-1}$
NMR (DMSO-$d_6$, δ): 1.98 (3H, m), 2.20–5.10 (18H, m), 7.00–7.60 (13H, m)
MASS (APCI): 554 (M+H)$^+$ (free)

(2) (4R,9aR)-8-Acetyl-4-benzhydryl-2-[2-methoxy-5-(4-pyridyl)benzyl]octahydro-2H-pyrazino[1,2-a]pyrazine trihydrochloride mp: 210–215° C.

$[\alpha]_D^{30.1}$: −47.25° (C=0.60, MeOH)

IR (KBr): 3435, 1639, 1606, 1495, 1448, 1277, 1147 cm$^{-1}$

NMR (DMSO-d$_6$, δ): 1.99 (3H, s), 2.20–4.80 (18H, m), 7.05–7.45 (11H, m), 8.13 (1H, d, J=8.9 Hz), 8.40–8.50 (3H, m), 8.98 (2H, d, J=6.7 Hz)

MASS (APCI): 547 (M+H)$^+$ (free)

(3) (4R,9aR)-8-Acetyl-4-benzhydryl-2-[2-ethoxy-5-[5-(trifluoromethyl)-1H-tetrazol-1-yl]benzyl]octahydro-2H-pyrazino[1,2-a]pyrazine dihydrochloride mp: 162–165° C.

$[\alpha]_D^{30.3}$: −47.00° (C=0.80, MeOH)

IR (KBr): 3435, 1647, 1504, 1444, 1431, 1265, 1201, 1163, 1036 cm$^{-1}$

NMR (DMSO-d$_6$, δ): 1.24–1.32 (3H, m), 1.94–1.99 (3H, m), 2.20–4.60 (17H, m), 7.10–7.50 (11H, m), 7.70–7.90 (2H, m)

MASS (API-ES): 620 (M+H)$^+$ (free)

(4) (4R,9aR)-8-Acetyl-4-benzhydryl-2-[2-methoxy-5-(1H-imidazol-1-yl)benzyl]octahydro-2H-pyrazino[1,2-a]pyrazine trihydrochloride NMR (DMSO-d$_6$, δ): 1.90–1.99 (3H, m), 2.20–4.60 (18H, m), 7.10–7.50 (11H, m), 7.83 (1H, d, J=8.9 Hz), 7.97 (1H, s), 8.13 (1H, s), 8.29 (1H, s), 9.71 (1H, s)

MASS (APCI): 536 (M+H)$^+$ (free)

(5) (4R,9aR)-8-Acetyl-4-benzhydryl-2-[2-methoxy-5-(trifluoromethyl)benzyl]octahydro-2H-pyrazino[1,2-a]pyrazine dihydrochloride mp: 147–150° C.

$[\alpha]_D^{30.3}$: −53.46° (C=0.26, MeOH)

IR (KBr): 3435, 1626, 1448, 1333, 1269, 1165, 1122 cm$^{-1}$

NMR (DMSO-d$_6$, δ): 1.91–1.99 (3H, m), 2.20–4.40 (18H, m), 7.10–7.50 (11H, m), 7.75 (1H, d, J=8.8 Hz), 7.87 (1H, s)

MASS (APCI): 538 (M+H)$^+$ (free)

(6) (4R,9aR)-8-Acetyl-4-benzhydryl-2-[2-methoxy-5-(furan-3-yl)benzyl]octahydro-2H-pyrazino[1,2-a]pyrazine dihydrochloride mp: 173–177° C.

$[\alpha]_D^{30.3}$: −57.27° (C=0.75, MeOH)

IR (KBr): 3435, 1645, 1512, 1448, 1431, 1259, 1151, 1022 cm$^{-1}$

MASS (APCI): 536 (M+H)$^+$ (free)

NMR (DMSO-d$_6$, δ) 1.91–1.99 (3H, m), 2.20–4.50 (18H, m), 6.92 (1H, s), 6.98–7.45 (11H, m), 7.61 (1H, d, J=8.9 Hz), 7.75 (1H, s), 7.84 (1H, d, J=5.5 Hz), 8.06 (1H, s)

(7) (4R,9aR)-8-Acetyl-4-benzhydryl-2-[(4-methoxypyridin-3-yl)methyl]octahydro-2H-pyrazino[1,2-a]pyrazine trihydrochloride mp: 205–210° C.

$[\alpha]_D^{30.2}$: −62.83° (C=0.60, MeOH)

IR (KBr): 3435, 1641, 1502, 1448, 1431, 1267, 1238 cm$^{-1}$

NMR (DMSO-d$_6$, δ): 1.91–1.99 (3H, m), 2.20–4.60 (18H, m), 7.10–7.70 (11H, m), 8.84 (2H, m)

MASS (APCI): 471 (M+H)$^+$ (free)

(8) (4R,9aR)-8-Acetyl-4-benzhydryl-2-[2-isopropoxy-5-[5-(trifluoromethyl)-1H-tetrazol-1-yl]benzyl]octahydro-2H-pyrazino[1,2-a]pyrazine dihydrochloride mp: 167–171° C.

$[\alpha]_D^{30.2}$: −37.44° (C=0.45, MeOH)

IR (KBr): 3435, 2981, 1649, 1502, 1431, 1265, 1201, 1165 cm$^{-1}$

NMR (DMSO-d$_6$, δ): 1.17–1.30 (6H, m), 1.90–1.99 (3H. m), 2.20–4.90 (16H, m), 7.10–7.50 (11H, m), 7.70–7.90 (2H, m)

MASS (API-ES): 634 (M+H)$^+$ (free)

(9) (4R,9aR)-8-Acetyl-4-benzhydryl-2-(2,4,6-trimethoxybenzyl)octahydro-2H-pyrazino[1,2-a]pyrazine dihydrochloride mp: 170–173° C.

$[\alpha]_D^{30.0}$: −67.35° (C=0.66, MeOH)

IR (KBr): 3435, 1647, 1610, 1462, 1427, 1234, 1147, 1041 cm$^{-1}$

NMR (DMSO-d$_6$, δ): 1.96 (3H, s), 2.10–4.50 (15H, m), 3.66 (3H, s), 3.68 (3H, s), 3.80 (3H, s), 6.21 (1H, s), 6.23 (1H, s), 7.10–7.50 (10H, m)

MASS (API-ES): 530 M+H)$^+$ (free)

(10) (4R,9aR)-8-Acetyl-4-benzhydryl-2-(2-ethoxy-6-methoxybenzyl)octahydro-2H-pyrazino[1,2-a]pyrazine dihydrochloride IR (KBr): 3435, 1647, 1599, 1468, 1255, 1122 cm$^{-1}$ NMR (DMSO-d$_6$, δ): 1.15–1.30 (3H, m), 1.90–2.00 (3H, m), 2.20–4.50 (20H, m), 6.60–6.70 (2H, m), 7.10–7.50 (11H, m)

MASS (APCI): 514 (M+H)$^+$ (free)

(11) (4R,9aR)-8-Acetyl-4-benzhydryl-2-(2-isopropoxy-6-methoxybenzyl)octahydro-2H-pyrazino[1,2-a]pyrazine dihydrochloride IR (KBr): 3435, 2976, 1651, 1595, 1469, 1431, 1255, 1117 cm$^{-1}$ NMR (DMSO-d$_6$, δ): 1.10–1.25 (6H, m), 1.95–2.00 (3H, m), 2.20–4.65 (19H, m), 6.59–6.70 (2H, m), 7.10–7.50 (11H, m)

MASS (APCI): 528 (M+H)$^+$ (free)

(12) (4R,9aR)-8-Acetyl-4-benzhydryl-2-(2-ethoxy-4,6-dimethoxybenzyl)octahydro-2H-pyrazino[1,2-a]pyrazine dihydrochloride IR (KBr): 3435, 2975, 1647, 1606, 1460, 1429, 1232, 1146 cm$^{-1}$ NMR (DMSO-d$_6$, δ): 1.05–1.25 (3H, m), 1.96–2.00 (3H, m), 3.79 (3H, s), 2.20–4.70 (20H, m), 6.18–6.22 (2H, m), 7.10–7.50 (10H, m)

MASS (APCI): 543 (M)$^+$ (free)

(13) (4R,9aR)-8-Acetyl-4-benzhydryl-2-[2-methoxy-5-(3-thienyl)benzyl]octahydro-2H-pyrazino[1,2-a]pyrazine dihydrochloride mp: 177–181° C.

$[\alpha]_D^{29.9}$: −55.69° (C=0.29, MeOH)

IR (KBr): 3425, 1647, 1498, 1444, 1429, 1259, 1142, 1022 cm$^{-1}$

NMR (DMSO-d$_6$, δ): 1.99 (3H, s), 2.10–5.30 (18H, m), 7.00–8.05 (16H, m)

MASS (APCI): 552 (M+H)$^+$ (free)

(14) (4R,9aR)-8-Acetyl-4-benzhydryl-2-(2-isopropoxy-4,6-dimethoxybenzyl)octahydro-2H-pyrazino[1,2-a]pyrazine dihydrochloride IR (KBr): 3400, 1645, 1610, 1454, 1427, 1203, 1151, 1132 cm$^{-1}$ NMR (DMSO-d$_6$, δ): 1.10–1.24 (6H, m), 1.91–2.00 (3H, m), 3.79 (3H, s), 2.20–4.80 (19H, m), 6.19–6.22 (2H, s), 7.10–7.45 (10H, m)

MASS (API-ES): 558 (M+H)$^+$ (free)

EXAMPLE 56

Diisopropylethylamine (0.236 ml) was added to an ice-cooled solution of 1-[3-(bromomethyl)-4-fluorophenyl]-5-(trifluoromethyl)-1H-tetrazole and in N,N-dimethylformamide (2 ml) and the mixture was stirred for 3 hours at room temperature. The mixture was washed with aqueous sodium hydrogen carbonate. The organic layer was separated, dried over magnesium sulfate, and evaporated under reduced pressure. The syrup was purified by column chromatography on silica gel using a mixed solvent of dichloromethane and methanol (100:1–40:1). The fractions containing the objective compound were collected to give a syrup. The syrup was treated with 4N hydrogen chloride in ethyl acetate solution to give (4R,8aS)-4-benzhydryl-2-[2-fluoro-5-[5-(trifluoromethyl)-1H-tetrazol-1-yl]benzyl]octahydropyrrolo[1,2-a]pyrazine dihydrochloride (0.22 g).

IR (KBr): 3400, 2800–2500, 1533 cm$^{-1}$

NMR (DMSO-d$_6$, δ): 1.50–5.00 (13H, m), 7.15–8.00 (13H, m), 11.50–12.00 (2H, m)

MASS (APCI): 537 (M+H)$^+$ (free)

EXAMPLE 57

The following compound was obtained according to a similar manner to that of Example 56.
(4R,9aR)-8-Acetyl-4-benzhydryl-2-[2-fluoro-5-[5-(trifluoromethyl)-1H-tetrazol-1-yl]benzyl]octahydro-2H-pyrazino[1,2-a]pyrazine dihydrochloride IR (KBr): 3400, 2800–2500, 1533 cm$^{-1}$ NMR (DMSO-d$_6$, δ): 1.95–2.00 (3H, m), 2.20–5.20 (15H, m), 7.13–8.00 (13H, m)

MASS (APCI): 594 (M+H)$^+$ (free)

EXAMPLE 58

To a solution of 2-methoxy-5-[5-(trifluoromethyl)-1H-tetrazol-1-yl]benzaldehyde (582 mg) and (4S,9aS)-4-benzhydryl-8-(benzyloxycarbonyl)octahydro-2H-pyrazino[1,2-a]pyrazine dihydrochloride (1.0 g) in dichloromethane (10 ml) was added portionwise sodium tritacetoxyborohydride (824 mg) under ice-cooling, and then it was stirred at room temperature for 90 minutes. The mixture was poured into aqueous sodium hydrogen carbonate and extracted with dichloromethane. The organic layer was washed with brine, dried over sodium sulfate, and evaporated under reduced pressure. The resulting residue was purified by column chromatography on silica gel (23 g) using a mixed solvent of hexane and ethyl acetate (2:1). The fractions containing the objective compound were collected and evaporated under reduced pressure to give (4S,9aS)-4-benzhydryl-8-benzyloxycarbonyl-2-[2-methoxy-5-[5-(trifluoromethyl)-1H-tetrazol-1-yl]benzyl]octahydro-2H-pyrazino[1,2-a]pyrazine (0.98 g) as a colorless foam.

NMR (CDCl$_3$, δ): 3.81 (3H, s), 1.80–4.25 (15H, m), 5.08 (2H, s), 6.92 (1H, d, J=8.7 Hz), 7.05–7.40 (17H, m)

MASS (APCI): 698 (M+H)$^+$

EXAMPLE 59

(4S,9aS)-4-Benzhydryl-8-benzyloxycarbonyl-2-[2-methoxy-5-[5-(trifluoromethyl)-1H-tetrazol-1-yl]benzyl]octahydro-2H-pyrazino[1,2-a]pyrazine (187 mg) was dissolved in tetrahydrofuran (2 ml), and triethylamine (0.0747 ml) was added to it at room temperature. The solution was hydrogenated over 10% palladium-charcoal (50% wet, 40 mg) at room temperature under atmospheric pressure for 2 hours. After removal of the catalyst by filtration, the filtrate was evaporated under reduced pressure to give colorless syrup. The resulting residue was purified by column chromatography on silica gel (7 g) using a mixed solvent of dichloromethane and methanol (10:1). The fractions containing the objective compound were collected and evaporated under reduced pressure to give a syrup. To a solution of the syrup in dichloromethane (2 ml) was added a solution of 4N hydrogen chloride in ethyl acetate (0.050 ml), and triturated with diisopropyl ether. The precipitate was collected by filtration and dried under reduced pressure for 5 hours at 40° C. to give (4S,9aR)-4-benzhydryl-2-[2-methoxy-5-[5-(trifluoromethyl)-1H-tetrazol-1-yl]benzyl]octahydro-2H-pyrazino[1,2-a]pyrazine trihydrochloride (154 mg) as a colorless powder.

NMR (DMSO-d$_6$, δ): 3.82 (3H, s), 2.15–4.70 (15H, m), 7.15–7.40 (11H, m), 7.75–7.90 (2H, m), 9.43 (2H, br)

MASS (APCI): 564 (M+H)$^+$ (free)

EXAMPLE 60

(4S,9aS)-4-Benzhydryl-8-benzyloxycarbonyl-2-[2-methoxy-5-[5-(trifluoromethyl)-1H-tetrazol-1-yl]benzyl]octahydro-2H-pyrazino[1,2-a]pyrazine (740 mg) was dissolved in tetrahydrofuran (8 ml), and triethylamine (0.296 ml) was added to it at room temperature. The solution was hydrogenated over 10% palladium-charcoal (50% wet, 150 mg) at room temperature under atmospheric pressure for 2 hours. After removal of the catalyst by filtration, the filtrate was evaporated under reduced pressure to give a colorless syrup. To a solution of the syrup in dichloromethane (10 ml) was added N,N-diisopropylethylamine (0.374 ml) and acetyl chloride (0.114 ml) under ice-cooling. After stirred at the same temperature for 2 hours, the mixture was poured into aqueous sodium hydrogen carbonate and extracted with dichloromethane. The organic layer was washed with brine, dried over sodium sulfate, and evaporated under reduced pressure. The resulting residue was purified by column chromatography on silica gel (10 g) using a mixed solvent of dichloromethane and methanol (20:1). The fractions containing the objective compound were collected and evaporated under reduced pressure to give a syrup. To a solution of the syrup in ethyl acetate (3 ml) was added a solution of 4N hydrogen chloride in ethyl acetate (0.70 ml), and triturated with diisopropyl ether. The precipitate was collected by filtration and dried under reduced pressure for 5 hours at 40° C. to give (4S,9aS)-8-acetyl-4-benzhydryl-2-[2-methoxy-5-[5-(trifluoromethyl)-1H-tetrazol-1-yl]benzyl]octahydro-2H-pyrazino[1,2-a]pyrazine dihydrochloride (580 mg) as a colorless powder.

NMR (DMSO-d$_6$, δ): 1.90–2.00 (3H, m), 2.15–4.70 (18H, m), 7.10–7.45 (11H, m), 7.70–7.90 (2H, m)

MASS (API-ES): 606 (M+H)$^+$ (free)

EXAMPLE 61

The following compounds were obtained according to a similar manner to that of Example 2.
(1) 7-Benzhydryl-9-[2-methoxy-5-[5-(trifluoromethyl)-1H-tetrazol-1-yl]benzyl]-6,9-diazaspiro[4.5]decane dihydrochloride IR (KBr): 3400–3200, 2900–2500, 1504 cm$^{-1}$ NMR (DMSO-d$_6$, δ): 1.50–4.9 (19H, m), 7.09–8.20 (13H, m), 8.90–9.10 (1H, m), 9.70–10.00 (2H, m)

MASS (APCI): 563 (M+H)$^+$ (free)
(2) 6-Benzhydryl-4-[2-methoxy-5-[5-(trifluoromethyl)-1H-tetrazol-1-yl]benzyl]-2,2-dimethylpiperazine dihydrochloride IR (KBr): 3400–3100, 2900–2500, 1504, 1454 cm$^{-1}$ NMR (DMSO-d$_6$, δ): 1.35 (3H, s), 1.50 (3H, s), 2.20–5.00 (11H, m), 7.14–7.71 (14H, m), 9.80–10.20 (3H, m)

MASS (APCI): 537 (M+H)$^+$ (free)

EXAMPLE 62

The following compounds were obtained according to a similar manner to that of Example 4.
(1) 7-Benzhydryl-9-[2-methoxy-5-[5-(trifluoromethyl)-1H-tetrazol-1-yl]benzyl]-6-methyl-6,9-diazaspiro[4.5]decane dihydrochloride IR (KBr): 3400–3200, 2900–2500, 1504 cm$^{-1}$ NMR (DMSO-d$_6$, δ) 1.50–4.9 (19H, m), 3.80 (3H, s), 7.09–8.20 (13H, m), 8.50–8.60 (2H, m)

MASS (APCI): 577 (M+H)$^+$ (free)

(2) 6-Benzhydryl-4-[2-methoxy-5-[5-(trifluoromethyl)-1H-tetrazol-1-yl]benzyl]-1,2,2-trimethylpiperzine dihydrochloride IR (KBr): 3400–3100, 2900–2500, 1504, 1454 cm$^{-1}$
NMR (DMSO-$d_6$, δ): 1.35–1.50 (6H, m), 2.20–5.00 (14H, m), 7.14–7.71 (13H, m)
MASS (APCI): 551 (M+H)$^+$ (free)

What is claimed is:

1. A compound of the formula (I):

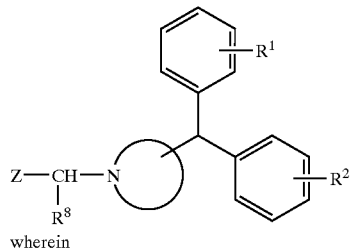

wherein

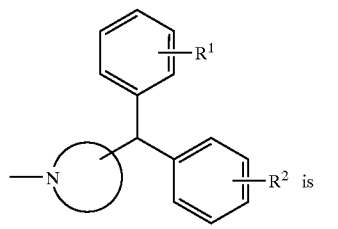 is

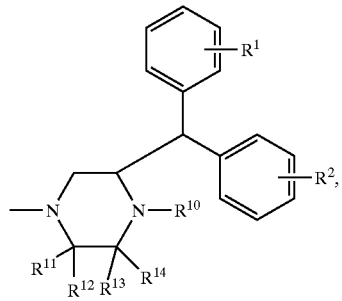

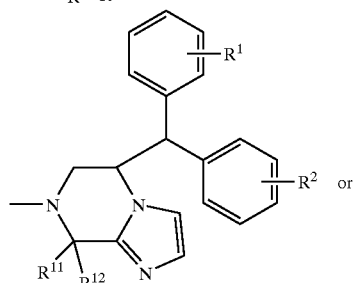 or

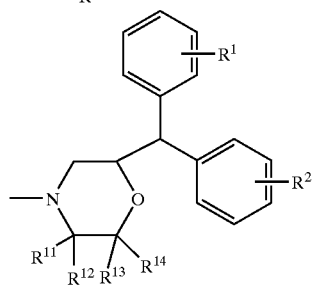

in which $R^1$ and $R^2$ are independently hydrogen, halogen, lower alkoxy, lower alkyl or mono(or di or tri)halo(lower)alkyl, $R^{10}$ is hydrogen or lower alkyl optionally substituted with lower alkoxy, carbamoyl or phenyl, $R^{11}$, $R^{12}$, $R^{13}$ and $R^{14}$ are independently hydrogen, lower alkoxycarbonyl or lower alkyl optionally substituted with hydroxy or lower alkoxy, and $R^{10}$ and $R^{14}$ optionally forming —(CH$_2$)$_i$—CHR$^{15}$—(CH$_2$)$_j$—, —(CH$_2$)$_i$—NR$^{16}$—(CH$_2$)$_j$—, —(CH$_2$)$_i$—O—CH$_2$—CO— or —(CH$_2$)$_i$—O—(CH$_2$)$_j$—, wherein i and j are independently 1 or 2, $R^{15}$ is hydrogen, halogen, lower alkyl, hydroxy, lower alkoxy, amino, lower alkylamino or di(lower)alkylamino and $R^{16}$ is hydrogen, lower alkyl, lower alkanoyl, lower alkoxycarbonyl, benzyloxycarbonyl, lower alkylsulfonyl or mono(or di or tri)halo(lower)alkylsulfonyl, or $R^{12}$ and $R^{13}$ optionally forming —(CH$_2$)$_i$—CHR$^{15}$—(CH$_2$)$_j$—, wherein i, j and $R^{15}$ are defined as above, or $R^{13}$ and $R^{14}$ optionally forming oxo or two to five methylenes, Z is

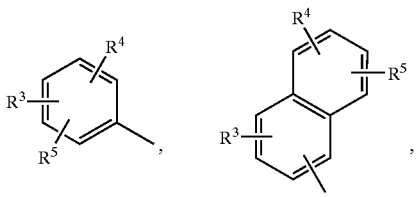

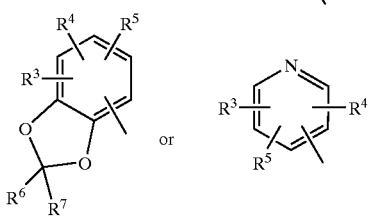

in which $R^3$, $R^4$ and $R^5$ are independently hydrogen; halogen; lower alkyl, mono(or di or tri)halo(lower)alkyl; cyano; lower alkoxycarbonyl; lower alkylthio; lower alkylsulfonyl; hydroxy; lower alkoxy optionally substituted with lower alkoxy, lower alkoxycarbonyl, carbamoyl, cyano, phenyl or one, two or three halogen(s); lower alkenyloxy; cyclo(lower)alkyloxy; nitro; lower alkylamino; di(lower)alkylamino; or imidazolyl, pyrazolyl, thienyl, thiazolyl, furyl, tetrazolyl, pyridyl or phenyl, each of which may have a substituent selected from a group which consists of lower alkyl, mono(or di or tri)halo(lower)alkyl, lower alkylsulfonyl, lower alkylsulfinyl, lower alkylthio, lower alkylamino and di(lower)alkylamino, and $R^6$ and $R^7$ are independently hydrogen or halogen, and $R^8$ is hydrogen or lower alkyl, and a salt thereof.

2. The compound of claim 1, in which

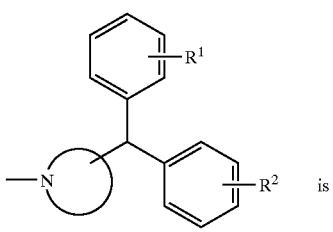 is

-continued
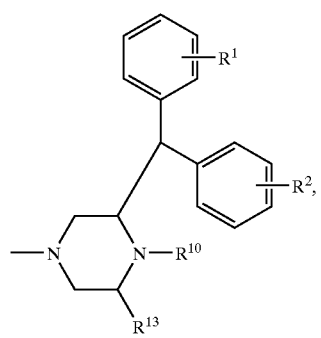
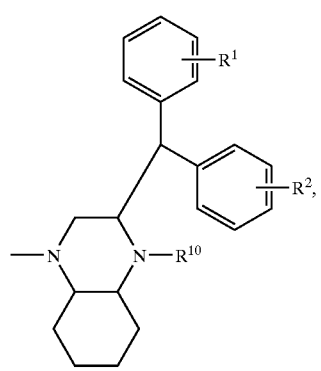
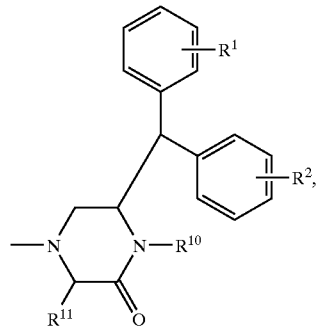
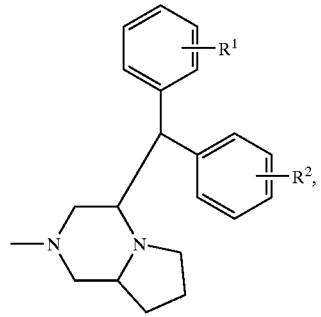
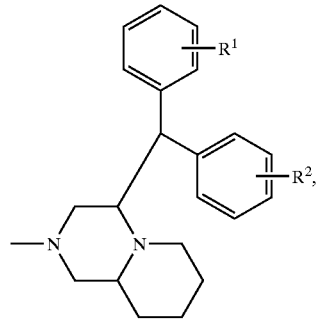
-continued
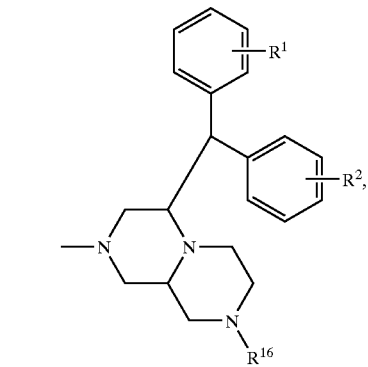
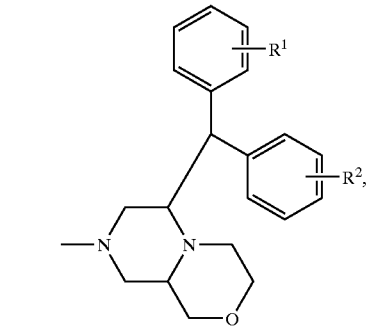
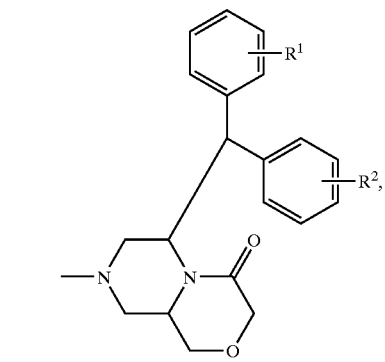
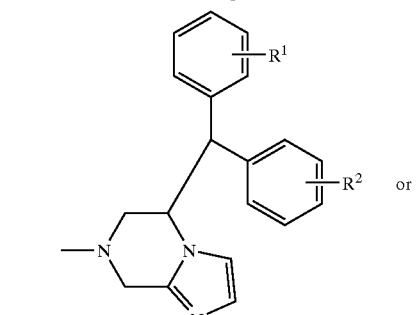 or
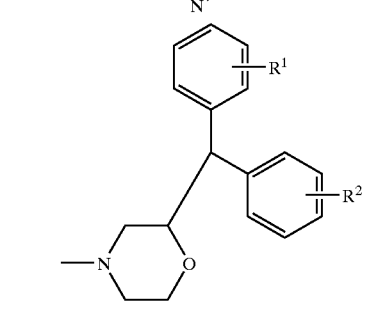

in which $R^1$ and $R^2$ are independently hydrogen, $C_1$–$C_4$ alkoxy, $C_1$–$C_4$ alkyl or mono(or di or tri)halo($C_1$–$C_4$)alkyl, $R^{10}$ is hydrogen or $C_1$–$C_4$ alkyl optionally substituted with $C_1$–$C_4$ alkoxy, carbamoyl or phenyl, $R^{11}$ and $R^{13}$ are independently hydrogen, $C_1$–$C_4$ alkoxycarbonyl or $C_1$–$C_4$ alkyl optionally substituted with hydroxy or $C_1$–$C_4$ alkoxy, $R^{16}$ is hydrogen, $C_1$–$C_4$ alkyl, $C_1$–$C_4$ alkanoyl, $C_1$–$C_4$ alkoxycarbonyl, benzyloxycarbonyl, $C_1$–$C_4$ alkylsulfonyl or mono(or di or tri)halo($C_1$–$C_4$)alkylsulfonyl, Z is

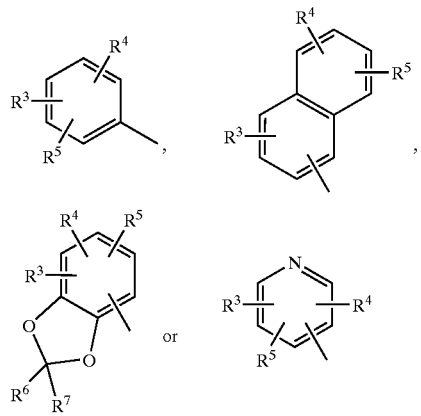

in which $R^3$, $R^4$ and $R^5$ are independently hydrogen; halogen; $C_1$–$C_4$ alkyl; mono(or di or tri)halo($C_1$–$C_4$)alkyl; cyano; $C_1$–$C_4$ alkoxycarbonyl; $C_1$–$C_4$ alkylthio; $C_1$–$C_4$ alkylsulfonyl; hydroxy; $C_1$–$C_4$ alkoxy optionally substituted with $C_1$–$C_4$ alkoxy, $C_1$–$C_4$ alkoxycarbonyl, carbamoyl, cyano, phenyl or one, two or three halogen(s); $C_2$–$C_4$ alkenyloxy; cyclo($C_3$–$C_6$)alkyloxy; nitro; $C_1$–$C_4$ alkylamino; di($C_1$–$C_4$)alkylamino; or imidazolyl, pyrazolyl, thienyl, thiazolyl, furyl, tetrazolyl, pyridyl or phenyl, each of which may have a substituent selected from a group which consists of $C_1$–$C_4$ alkyl, mono(or di or tri)halo($C_1$–$C_4$)alkyl, $C_1$–$C_4$ alkylsulfonyl, $C_1$–$C_4$ alkylsulfinyl, $C_1$–$C_4$ alkylthio, $C_1$–$C_4$ alkylamino and di($C_1$–$C_4$)alkylamino, and $R^6$ and $R^7$ are independently hydrogen or halogen, and $R^8$ is hydrogen or $C_1$–$C_4$ alkyl.

3. The compound of claim 2, in which

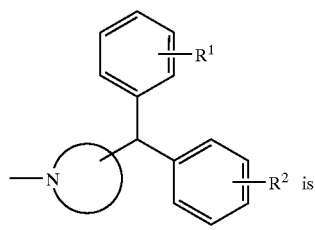

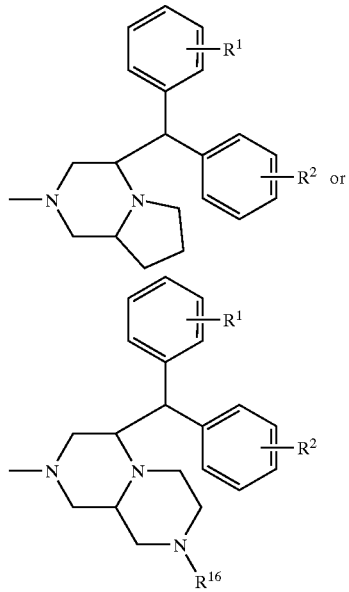

in which $R^1$ and $R^2$ are independently hydrogen, $C_1$–$C_4$ alkoxy, $C_1$–$C_4$ alkyl or mono(or di or tri)halo($C_1$–$C_4$)alkyl, and $R^{16}$ is hydrogen, $C_1$–$C_4$ alkyl, $C_1$–$C_4$ alkanoyl, $C_1$–$C_4$ alkoxycarbonyl, benzyloxycarbonyl, $C_1$–$C_4$ alkylsulfonyl or mono(or di or tri)halo($C_1$–$C_4$)alkylsulfonyl, Z is 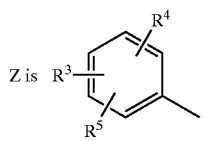

in which $R^3$ is hydrogen, $R^4$ is $C_1$–$C_4$ alkoxy, and $R^5$ is imidazolyl, pyrazolyl, thienyl, thiazolyl, furyl, tetrazolyl, pyridyl or phenyl, each of which may have a substituent selected from a group which consists of $C_1$–$C_4$ alkyl, mono(or di or tri)halo($C_1$–$C_4$)alkyl, $C_1$–$C_4$ alkylsulfonyl, $C_1$–$C_4$ alkylsulfinyl, $C_1$–$C_4$ alkylthio, $C_1$–$C_4$ alkylamino and di($C_1$–$C_4$)alkylamino, and $R^8$ is hydrogen or $C_1$–$C_4$ alkyl.

4. A compound of claim 3, which is selected from a group which consists of (1) (4R, 8aS)-4-Benzhydryl-2-[2-methoxy-5-[5-(trifluoromethyl)-1H-tetrazol-1-yl]benzyl]octahydropyrrolo[1,2-a]pyrazine, and (2) 1-[(6R,9aR)-6-Benzhydryl-8-[2-methoxy-5-[5-(trifluoromethyl)-1H-tetrazol-1-yl]benzyl]octahydropyrazino[1,2-a]pyrazin-2-yl]ethanone, or a pharmaceutically acceptable salt thereof.

5. A process for the preparation of the compound of claim 1 or a salt thereof, which comprises, (1) reacting a compound of the formula (II):

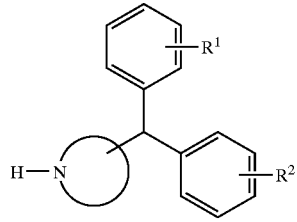
(II)

wherein

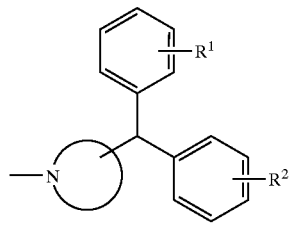

is defined in claim 1, or its reactive derivative at the imino group or a salt thereof, with a compound of the formula (III):

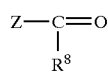
(III)

wherein Z and $R^8$ are each as defined in claim 1, or a salt thereof to give a compound of the formula (I):

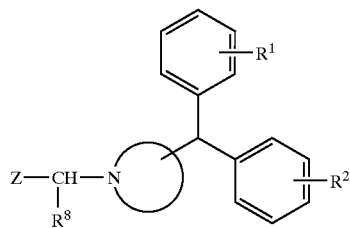
(I)

wherein

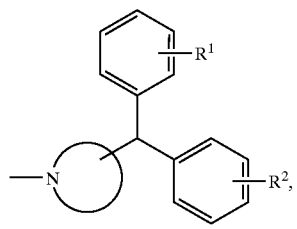

Z and $R^8$ are each as defined in claim 1, or a salt thereof, or (2) reacting a compound of the formula (Ia):

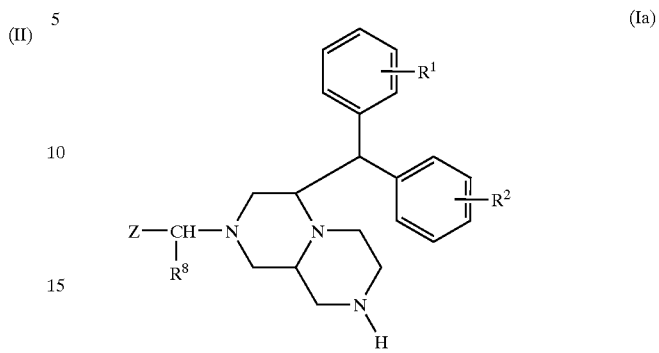
(Ia)

wherein Z, $R^1$, $R^2$ and $R^8$ are each as defined in claim 1, or a salt thereof, with a compound of the formula (IV):

(IV)

wherein $R^{16}$ is as defined in claim 1, and $W_1$ is a leaving group, or a salt thereof to give a compound of the formula (Ib):

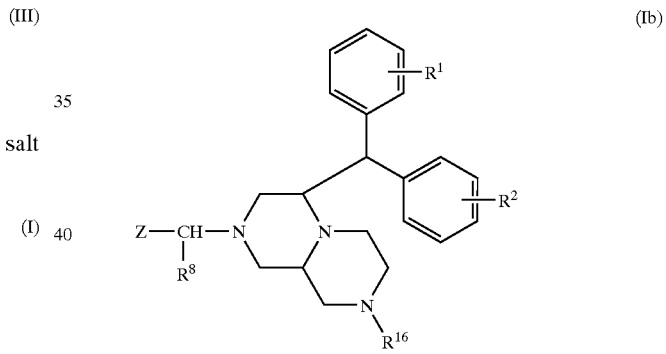
(Ib)

wherein Z, $R^1$, $R^2$, $R^8$ and $R^{16}$ are each as defined in claim 1, or a salt thereof.

6. A pharmaceutical composition which comprises, as an active ingredient, a compound of claim 1 or a pharmaceutically acceptable salt thereof in admixture with pharmaceutically acceptable carriers.

7. A method for treating Tachykinin-mediated diseases which comprises administering an effective amount of a compound of claim 1 or a pharmaceutically acceptable salt thereof to human beings or animals.

* * * * *

UNITED STATES PATENT AND TRADEMARK OFFICE
CERTIFICATE OF CORRECTION

PATENT NO. : 6,787,543 B2
DATED : September 7, 2004
INVENTOR(S) : Take et al.

It is certified that error appears in the above-identified patent and that said Letters Patent is hereby corrected as shown below:

Title page,
Item [30], Foreign Application Priority Data, should read:
-- [30]         Foreign Application Priority Data
     Jun. 29, 2000     (AU) ..................... PQ8454
     Jan. 2, 2001     (AU) ..................... PR2373 --

Signed and Sealed this

Thirtieth Day of November, 2004

JON W. DUDAS
*Director of the United States Patent and Trademark Office*